US010034934B2

(12) United States Patent
Marthaler et al.

(10) Patent No.: US 10,034,934 B2
(45) Date of Patent: Jul. 31, 2018

(54) PORCINE EPIDEMIC DIARRHEA VIRUS VACCINES AND METHODS OF USE THEREOF

(71) Applicant: REGENTS OF THE UNIVERSITY OF MINNESOTA, Minneapolis, MN (US)

(72) Inventors: Douglas Marthaler, Minneapolis, MN (US); Kurt Rossow, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 15/125,526

(22) PCT Filed: Mar. 10, 2015

(86) PCT No.: PCT/US2015/019713
§ 371 (c)(1),
(2) Date: Sep. 12, 2016

(87) PCT Pub. No.: WO2015/138455
PCT Pub. Date: Sep. 17, 2015

(65) Prior Publication Data
US 2017/0080083 A1    Mar. 23, 2017

Related U.S. Application Data

(60) Provisional application No. 61/951,439, filed on Mar. 11, 2014.

(51) Int. Cl.
*A61K 39/215*    (2006.01)
*C12N 7/00*    (2006.01)
*C07K 14/165*    (2006.01)
*A61K 39/00*    (2006.01)

(52) U.S. Cl.
CPC .......... *A61K 39/215* (2013.01); *C07K 14/165* (2013.01); *C12N 7/00* (2013.01); *A61K 2039/525* (2013.01); *A61K 2039/53* (2013.01); *A61K 2039/54* (2013.01); *A61K 2039/552* (2013.01); *A61K 2039/55516* (2013.01); *A61K 2039/55583* (2013.01); *C12N 2770/00021* (2013.01); *C12N 2770/00022* (2013.01); *C12N 2770/20034* (2013.01)

(58) Field of Classification Search
None
See application file for complete search history.

(56) References Cited

U.S. PATENT DOCUMENTS

| | | | |
|---|---|---|---|
| 5,057,540 A | 10/1991 | Kensil et al. | |
| 5,078,996 A | 1/1992 | Conlon et al. | |
| 5,254,339 A | 10/1993 | Morein | |
| 6,113,918 A | 9/2000 | Johnson et al. | |
| 6,149,919 A | 11/2000 | Domenighini et al. | |
| 6,207,646 B1 | 3/2001 | Krieg et al. | |
| 6,299,884 B1 | 10/2001 | Van Nest et al. | |
| 7,115,730 B1 | 10/2006 | Pizza et al. | |
| 7,285,281 B2 | 10/2007 | Green et al. | |
| 7,291,588 B2 | 11/2007 | Pizza et al. | |
| 7,332,174 B2 | 2/2008 | Green et al. | |
| 7,361,355 B2 | 4/2008 | Green et al. | |
| 7,384,640 B1 | 6/2008 | Holmes et al. | |
| 7,501,129 B2 | 3/2009 | Williams et al. | |
| 2017/0080083 A1* | 3/2017 | Marthaler | A61K 39/215 |

FOREIGN PATENT DOCUMENTS

| | | |
|---|---|---|
| CN | 102399806 A | 4/2012 |
| CN | 103992989 A | 8/2014 |
| CN | 104248762 A | 12/2014 |
| WO | 2015153425 A1 | 10/2015 |
| WO | 2016007576 A2 | 1/2016 |
| WO | 2016130569 A1 | 8/2016 |
| WO | 2016138421 A1 | 9/2016 |

OTHER PUBLICATIONS

Sequence alignment of instant SEQ ID No. 1 with GenEmbl database access noLC063846 by Suzuki et al in Infect Genet Evol in 2015.*
Sequence alignment of SEQ ID No. 1 with GenEmbl database access No. KJ645635 by Vlasova et al in Emerging Infectious Diseases in 2014.*
SEQ ID No. 2 sequence alignment with GenEmbl database access No. KJ645649 by Vlasova et al in Emerging Infectious Diseases on Mar. 28, 2014.*
SEQ ID No. 1 sequence alignment with GenEmbl database access No. JQ023161 by Park et al in Journal of Virology 2012.*
SEQ ID No. 2 sequence alignment with GenEmbl database access No. JQ023161 by Park et al in Journal of Virology 2012.*
Lin et al. (Veterinary Microbiology. 2017; 201: 62-71).*
Jarvis et al. (Preventative Veterinary Medicine. 2016; 123: 175-184).*
Carillo, et al., "The Multiple Sequence Alignment Problem in Biology Read More: http://epubs.siam.org/doi/abs/10.1137/0148063", SIAM J. Applied Math, vol. 48, 1073 (1988).
Chen, et al., "Isolation and Characterization of Porcine Epidemic Diarrhea Viruses Associated with the 2013 Disease Outbreak among Swine in the United States", Journal of Clinical Microbiology 52(1), 234-243 (2014).
Lin, et al., "Evolution, antigenicity and pathogenicity of global porcine epidemic diarrhea virus strains", Virus Research 226, 20-39 (2016).
Lin, et al., "Experimental infection of a US spike-insertion deletion porcine epidemic diarrhea virus in conventional nursing piglets and cross-protection to the original US PEDV infection", Veterinary Research 46, 134 (2015).
McGhee, et al., "New Perspectives in Mucosal Immunity with Emphasis on Vaccine Development", Seminars in Hematology, vol. 30 (4), Suppl 4, 3-15 (1993).
Meng, et al., "Evaluation on the Efficacy and Immunogenicity of Recombinant DNA Plasmids Expressing Spike Genes from Porcine Transmissible Gastroenteritis Virus and Porcine Epidemic Diarrhea Virus", PLOS One 8(3), e57468, 14 pages (2013).

(Continued)

*Primary Examiner* — Shanon A. Foley
(74) *Attorney, Agent, or Firm* — Viksnins Harris Padys Malen LLP

(57) ABSTRACT

The present disclosure provides an isolated or purified Porcine Epidemic Diarrhea Virus (PEDV) or Porcine Epidemic Diarrhea Virus (PEDV) S1 protein, and methods of use thereof.

3 Claims, 26 Drawing Sheets

(56) References Cited

OTHER PUBLICATIONS

Needleman, et al., "A general method applicable to the search for similarities in teh amino acid sequence of two proteins", J. Mol. Biol. 48, 443-453 (1970).
Oka, et al., "Cell culture isolation and sequence analysis of genetically diverse US porcine epidemic diarrhea virus strains including a novel strain with a large deletion in the spike gene", Veterinary Microbiology 173(3-4), 258-269.
Park, et al., "Complete genome sequences of a Korean virulent porcine epidemic diarrhea virus and its attenuated counterpart", Journal of Virology 86(10), 5964 (2012).
Patent Cooperation Treaty, International Searching Authority, Search Report and Written Opinion for PCT/US2015/019713, 14 pages, Jun. 22, 2015.
Song, et al., "Oral efficacy of Vero cell attenuated porcine epidemic diarrhea virus DR13 strain", Research in Veterinary Science 82, 134-140 (2007).
Song, et al., "Porcine epidemic diarrhoea virus: a comprehensive review of molecular epidemiology, diagnosis, and vaccines.", Virus Genes. 44(2) p. 167-175 (2012).
Stevenson, et al., "Emergence of Porcine epidemic diarrhea virus in the United States: clinical signs, lesions, and viral genomic sequences", J Vet Diagn Invest. 25(5), 649-654 (2013).
Vlasova, et al., "Distinct Characteristics and Complex Evolution of PEDV Strains, North America, May 2013-Feb. 2014", Emerging Infectious Diseases 20(10), 1620-1628 (2014).

\* cited by examiner

Fig. 1A

USA/Indiana12.83/2013 (SEQ ID NO:1):

CTTTTTCTAGACTCTTGTCTACTCAATTCAACTAAACGAAATTTTGTCCTTCCGGCCGCATGTCCATGCTGCTGGAAGC
TGACGTGGAATTTCATTAGGTTTGCTTAAGTAGCCATCGCAAGTGCTGTGCTGTCCTCTAGTTCCTGGTTGGCGTTCCG
TCGCCTTCTACATACTAGACAAACAGCCTTCCTCCGGTTCCGTCTGGGGGTTGTGTGGATAACTAGTTCCGTCTAGTTT
GAAACCAGTAACTGTCGGCTATGGCTAGCAACCATGTTACATTGGCTTTTGCCAATGATGCAGAAATTTCAGCTTTTGG
CTTTTGCACTGCTAGTGAAGCCGTCTCATACTATTCTGAGGCCGCCGCTAGTGGATTTATGCAATGCCGTTTCGTGTCC
TTCGATCTCGCTGACACTGTTGAGGGATTGCTTCCCGAAGACTATGTCATGGTGGTGGTCGGCACTACCAAGCTTAGTG
CGTATGTGGACACTTTTGGTAGCCGCCCCAAAAACATTTGTGGTTGGCTGTTATTTTCTAACTGTAATTACTTCCTCGA
AGAGTTAGAGCTTACTTTTGGTCGTCGTGGTGGTAACATCGTGCCAGTTGACCAATACATGTGTGGCGCTGACGGTAAA
CCTGTTCTTCAGGAATCCGAATGGGAGTATACAGATTTCTTTGCTGACTCCGAAGACGGTCAACTCAACATTGCTGGTA
TCACTTATGTGAAGGCCTGGATTGTAGAGCGATCGGATGTCTCTTATGCGAGTCAGAATTTAACATCTATTAAGTCTAT
TACTTACTGTTCAACCTATGAGCATACTTTTCCTGATGGTACTGCCATGAAGGTTGCACGTACTCCAAAGATTAAGAAG
ACTGTTGTCTTGTCTGAGCCACTTGCTACTATCTACAGGGAAATTGGTTCTCCTTTTGTGGATAATGGGAGCGATGCTC
GTTCTATCATTAAGAGACCAGTGTTCCTCCACGCTTTTGTTAAGTGTAAGTGTGGTAGTTATCATTGGACTGTTGGTGA
TTGGACTTCCTATGTCTCCACTTGCTGTGGCTTTAAGTGTAAGCCAGTCCTTGTGGCTTCATGCTCTGCTACGCCTGGT
TCTGTTGTGGTTACGCGCGCTGGTGCTGGCACTGGTGTTAAGTATTACAACAACATGTTCCTGCGCCATGTGGCAGACA
TTGATGGGTTGGCATTCTGGCGAATTCTCAAGGTGCAGTCCAAAGACGACCTCGCTTGCTCTGGTAAATTCCTTGAACA
CCATGAGGAAGGTTTCACAGATCCTTGCTACTTTTTGAATGACTCGAGCATTGCTACTAAGCTCAAGTTTGACATCCTT
AGTGGCAAGTTTTCTGATGAAGTCAAACAAGCTATCTTTGCTGGTCATGTTGTTGTTGGCAGCGCGCTCGTTGACATTG
TTGACGATGCACTGGGACAGCCTTGGTTTATACGTAAGCTTGGTGACCTTGCAAGTGCAGCTTGGGAGCAGCTTAAGGC
TGTCGTTAGAGGCCTTAACCTCCTGTCTGATGAGGTCGTGCTCTTTGGCAAAAGACTTAGCTGTGCCACTCTTAGTATC
GTTAACGGTGTTTTTGAGTTCATCGCCGAAGTGCCTGAGAAGTTGGCTGCGGCTGTTACAGTTTTTGTCAACTTCTTGA
ATGAGCTTTTTGAGTCTGCCTGTGACTGCTTAAAGGTCGGAGGTAAAACCTTTAACAAGGTTGGCTCTTATGTTCTTTT
TGACAACGCATTGGTTAAGCTTGTCAAGGCAAAAGTTCGCGGCCCACGACAGGCAGGTGTTTGTGAAGTTCGTTACACA
AGCCTTGTTATTGGGAGTACTACCAAGGTGGTTTCCAAGCGCGTTGAAAATGCCAATGTGAATCTCGTCGTCGTTGACG
AGGATGTGACCCTCAACACCACTGGTCGTACAGTTGTTGTTGACGGACTTGCATTCTTCGAGAGTGACGGGTTTTACAG
ACATCTTGCTGATGCTGACGTTGTCATTGAACATCCTGTTTATAAGTCTGCTTGTGAGCTCAAGCCAGTTTTTGAGTGT
GACCCAATACCTGATTTTCCTATGCCTGTGGCCGCTAGTGTTGCAGAGCTTTGTGTGCAAACTGATCTGTTGCTTAAAA
ATTACAACACTCCTTATAAAACTTACAGCTGCGTTGTGAGAGGTGATAAGTGTTGTATCACTTGCACCTTACATTTCAC

ATGAGTGCAACCCTGAAGGTTTGATGTCATTAGGTGCTGCTGATAAGCTGGTGTTGTTACAATTCCAATTGATTTTG
TAGCGTTGGTAAGTGCTTAACAATGACCGGCGGCGTTGAGCCATTGCTTGAAGCCATAAATGTATTAAAAGAGTAACAA
ACAGTGCCTGCTGGCAACTGTGTTACTTTTGAGTGTGCAGACATGATTTCTATTACTATGGTAGTATTGCCATCTGATG
GTGATGCTAATTATGACAAAATTATGCACGGCGCGTCAAGGTATCTAAGCTTAAAGGCAAGTATTGCTTGCTGT
TGGTGATGCCACGTTGTATTCCAAGTTGTCCCATCTCAGCTGCGTCAGTTCGTATCCAGCGTGGTAGGTTCGTGTAGTGGAGCGT
TTCTACGCAAATAAGAGTGTGGTTATTAAAGTCACTGAGGATACACGTGTTAAGGCTGTTAAGTAGAATCCACTG
TTACTTATGGACAACAAATTGGACCTGTTGTCTTGTTAATGGGATTCACATTATGGTTTTGATAGGCTGGTGAGTTCCACATGCTAGAC
TGTAGCTAAGGTTGTACCAAGTGCTAATTGGGATTCAACGGTAATTTAACGGTGTTAACCACCAGATAATAACTGTTGGGTTA
CATACTGGGTTGTCTTTCCTAGTGAAGTTGCTAGATTTAGGTTCAAGTCAGCAGCAGGTCTACAGGCTATGTGGGAGTCCTATTG
ATGTTACATGTTACAATTACAGTTGCTATGTTTGCATTGGTGTGACTGGCTTACTGGCTTGACAAAGGTCAGCTAGTGATTCAGAA
TACTGGTGATGTTTGCATTGGTGTGACTGGCTTACTGGCTTCGTGACAAAGGTCAGCTAGTGATTCAGAA
AATGCACTTAACATGTGTCAAGTACATTGTTCTGCTGGTTCTGTCACTATGAACGTGTCACGATGACGGCTGTT
GTTGTAGTAAGCGTGTGTCACTGCACCAGTTGTGAATGCTAGCGTATTGAAGCTTGGCGTCGAGGATGGTCTTTGTCC
ACATGGTCTTAACTACACCTCTTTCTTAAGGGTGTTTCTACACAACATTCCTAGATAATGTTACAATTGTTGTCAATGTTGGAAAACCTGTAGTG
GCACCATCACACCTCTTTCTTAAGGGTGTTTCTACACAACATTCCTAGATAATGTAACGGTGTTGTCGGCCATTATA
CTGTTTTGATCATGACACTGGTATGGTGCATGATGGAGATGCTTTTGTACCGGGTGATCTCAATGTATCTCCTGTTAC
AATGTGTCGTCAGAGCAGACGGCTGTTGTGATTAAAGACCCTGTGAAGAAAGTAGAGTTAGACGCTACAAGCTG
TTAGACACTATGCATTAGCATTTGGGTCTCTGTTTAGGGCCTTCGTAAGAGGGATGTTAAGTTCTAGCTCGTGTACCCCA
TGTACATCCTTAGCATTTGGGTCTCTGTTTAGGGCCTTCGTAAGAGGGATGTTAAGTTCTAGCTCGTGTACCCCA
ACGTACTGGTATTATGCGTAAAAGTGCGTATGCGCTATTATGCATTGTATGCATTACTATTCATGACAAATAACGCTTACAC
TGGTTCAAAGTTCTTGGTAAGTTTAGTTGGGTATTTAGTTGCATTGATGCATTTAGTTTGACAAGAATGAGTATTGCAACAG
CTATAGGTGGCCCGTGTTGTGATGATGTGTTGGTACCAGGAACTTCAGGAACTTCAGGTACACACACCTT
TGTTATTGTAAGGTCGTCCTATGGGTACCAGGAACTTTCAGAGACTTCAGGAACAACACACCTT
AGAGACCCATTAATTGTGATGTAATGTCCAGTGATGCCTTTCTTATTTGGCATTTCTCTGCAATTTGGGGGTGTTATGTAAGG
CTATTACTCTCTATTTATTTCCAGTAGTCTTAAAACATTCTGGTGTGTCTTGTGTTTCATGGCCTACACACAGTCCATTGGTTTT
GCAGCTTGCTGCCTTTGATGTCTTGGTGCTGCGATAAGGCATCGTCTTGGTGACGAGATCGTCGTCTTTCATCGTTACACGGCTATGATTCCGATGTTCCTAAG
CATGTTTTCCTTTGGCTGCGATAAGGCATCGTCTTGGTGACGAGATCGTCGTCTTCCATCGTTACACGGCGTATTGATGTTCCTAAG
CTATTTTCAGGGTACTGCAAATCCTTCTACGTACATGCCAATGTGGTGTTCTAGTTCTGTAAGAAGCACAATTTCTT
TTGTTAAATTGAATCTCTATGGTCCAGGCTGCACTTTATTAATGACGTCATCATGCAACTGAAGTTGGTAATGTTGTC
AACTTAATGTGCTACCGACAGTCCTGCCATCTATTCTTATGACATAACAGATAGCAAATACACTTGCAAAGAATCAACTTAAAATTG
ATAGTGGTGACACATTTGGAAGTACAACTTGGTATACAACAGATAGCAAATACACTTGCAAAGAATCAACTTAAAATTG
TAGCATAATCACAGAACTTTATTGTTTTAACAATAATGGTTCCAATGTAAATGTAAATCAGGTTAAGAATGCATGTGTTTATTTT

Fig. 1D

TCACAGATGCTTTGTAAACCTTGTAAGTTAGTGGACTCAGGCGTTGTTGTGCCAGTTGTCTGTTGATTTGGTGCAAGCT
TACATAGTGCTTTTGTTAGTGTGTTGTCGAATAGTTTGGCAAAGATCGTCAAGTTGTAATGACATGCAGGATTGCAA
GAGCACATTGGGTTTGATGATGTACCATTGACCTTTAATGCTGCTGTTGCTGAGGCTCATCGTACGATGTCCTC
TTGACTGACATGTCGTTCAACACATTTTACCACCAGTTATGCAAAACCAGAGAGAAATTCCCGTCATTGACATTGCCA
CGTGTATGCCGTGTAGGTGCCAGATGTTAATCATAACGTTCTTGTCAAGGATAGTATACCTGTGGTGGCTTGTACG
TGATTTCATTGCCCTTTCGGAAGAAGACTAGGAAGTACATTATTCGTACGACTAAAGTTAAGGGTATAACCTTCATGTTG
ACCTTTAATGATGTCGTATGCACACTACCATACTGTTTGCATTGCAAATAAGAAGGGTGCAGGTCTTCCTAGTT
TTTCAAAGGTTAAGAAATTCTTCTGGTTTTTGTCTGTCGTTTCATGGTTGCTGTTTCTTTGCACTAAGCTTTCTTGATTT
TAGTACTCAGGTTAGCAGTGATAGCAGTTATGACTTCAAGTATATTGAGAGTGGCCAGTTGAAGACTTTTGACAATCCA
CTTAGTTGTGTCATAATGCTTTAGTACTTCGACCAGTGGCATGACCCAGGTTGTTTCACCCCCGTCAACATC
CTAGTTGTCCTATAGTCCGTTGGTATCAGAGACGAAGCTGCACATCTGTTCCAGGTATYCCAGGTGTTTATTAGCTGG
TAAACACTGTTTTTGCTATTAACACCATTTTGGTACATCTGGTTTGTGCTTTGATGCTAGTGGCGTTGCTGATAAG
GGCGCTTGCATTTTAATTCGGCTTGCACCACATTATCTGGTTGGGTGGAACTGCTGTCTACTGTTATAAGAATGGTC
TAGTTGAAGGTGCTAAACTTTATAGTGAGTTGGCACCTCATAGCTACTATAAAAATGGTAGATGGTAATGCTGTGTCTTT
ACCTGAAATTATTTCACGCGGCTTTTGTTTGTTGGCGCCATAGATTCTTTGTCTATAATGCTAGAATCTCGGTTCGACTTTGTTT
GTGCAATCTGCAGAGGCTCTTTACATTGTGAATCGTTATTAGTGTTTTTTTCCAAGACACAGTACCAGTAACTGTGTCTGG
GTGGCACAGGGCTCTTTACATTGCATTATTGCTTTGCTACTGTCGGTTTGCTGTTGCCACTGTTCTATTGAACAATGTTCTTACATTGTAACAGAACA
TCAAATACTTTTTAATTGCATTATTGCTTTCACTGTCGGTTTGCTACTGTCGGTGCCATGTCCGGTTCAATAGCCATGTC
GGTGATATGTCGTGTGGCGTTTCACTGTCGGTGCTATGCAACTTTGTACTTCTGTGACTAAAGGTGTTAAAGGTGTTAGATATATGCCTTTGAGTTTAGTATCCGGCCATTTTGAGTTTATG
CACTTGGCATGTTGGGCTATGCAACTTTGTACTTCTGTGACTATGCCACATGGTGGGTTTGATGGTCCATTTTGAGTTTATG
ATTTTTGATCTCATATATAAGCTTAAGGTTCAACACAACTTGCAACACAACTTTTGGAGGGTGACAGTTCGTGACAGTTCGTGCAG
CCTAACCTTGTACATTGTGCTTGATATGCATGCAGTCATGATCCTATGAGAGACTTGCCAACTTCAGCGTCGAATGCAATGC
CAGGTACATTGTCGCTTGATATGCATGGCATCCATATTGATCAGGCTATACAGGCTTGTTTGCCATTTG
TAGTACTTACAATAAGTACAAGTATTATTCAGGCAGTGCTTCAGAGGCTGATTACAGGCTTGCTGTTTTGCCATTTG
GCCAAGGCTAGATGGATTATGCTTCTAATCACAATGACAGATTATACACCACACTGTGAGTTACAATTCAACTC
TACAGGCTGCTTGCGTAAGATGCCACATGCACCATCTGGTTGTTGAGAGAAGAGCATAGTCGTCGTGTTGCTATGGTAATAT
GGCTCTTAATGGCCTATGGCTATGGTTGATACTGTTATGTGCCCACGCCATGTTATAGCGTCATATATAGCACACTATA
GATTATGACTAGTGGCCCTTTGTGTTTTCTGTTTACGCCTCCACAACTTCTCCATTCATCTGTAAATGTTTCCTAGGTGTGTGG
GTGTAACCATGCGAGGTCGTTTGCAGATAAAGGTTAATCAAACAATGTCCACACGCCTAAGTACACCTATCGCAC
AGTTAGAACCAGGTGAATCTTTAATATCTTGGCGTGCTATGATGGTCTGCAGCTGGTGTTATGGCGTTAACATGCGC
TCTAATTACACTGTTATTAGAGGCTCGTTCATTAATGCGCTTGGGTTCACCTGGTTATAATATTAACAATGGTACCGTTG
AGTTTGCTATTTACATCAGCTGAACTTGGTTCATGTTCGTCAGGCGTCATGTTCAGGTTCAGGTAGCGACTTAGATGGTGTTATGTATGGTGG

Fig. 1E

TTATGAGGACCAACTACTTTGCAAGTTGAAGGGCTAGTAGTCTGTTACAGAGAATGTGTTGGCATTCTTTATGCA
GCACTCATTAATGGTTCTACCTGGTGCCTAGTTCTTCTAGAATGCTGTAGACAGTTAATGAGTGGCTGTTCATA
ATGGTATGACAACAGTAGTAATACTGATTGCTTTCTATTCTTGCTGCTAAGACTGGTGTTGATGTACAACGTTGT
GGCCTCAATCCAGTCTCTGCATAAGAATTTTGGTGGAAAGCAAATTCTTGGCTATACCTGTTGACAGATGAGTTACT
ACAGGTGAAGTTATACGTCAAATGTATGGGGTTAATCTTCAGAGTGGTTATGTTCACGCGCCTGCAGAAATGTCTTGC
TGGTTGGTTCTTTTCTGACTTCTTTTGGTCAGAATTAGTTCCTACACTAAGTTCTTTGGTAAATCCTGGTTATGT
CACACCTATGTTGCGTGTTGCTCATTGCTGCTGTCCTACACTTTGATGTTCACACTCAAGCATAAGACATTGTCTTCCAG
GTCTTTCTAATACCTGCTCTGATTGTTACATCTTGCATTAATTGGCATTTGAAGTTGTGAAGTTCTACAACTATTTGGCAG
AGCATTTTGATTACCATGTTCTCATGGGTTTTAATGCACAAGGTCTGTTAACATCTTTGTCTGCTTTGTTGTGTTAC
CATTTTACACGGCACATAACATATTTTTAACACACATGTCTGTCGTCATTGAGTTGCTTTGCACTGTGATGACT
GCGGCATATAACTATTTTTACGCTAGTGACATTCTTAGTGCAATTGCCCTATGACACTATTGCTAGTGTGACTGCAACTGGT
TCGTTGGTGCTGTTTGTTATAAAGCTGCTGTTATTGGGTTATTTACCGTGTATTCTACAACCGATTAGCTAGT
TTTTAAGTTAGTGTGTCTGTAGGTCATGACTATACTGTTAGGTGCGTGAGTTAAGTATATGGTTGCTAACGGCTAC
GTGCACCAACTGGAACACTTGATTCACTACTCTGTCTGCCAAATTGATTGGTATTGGTGCGGAATATTAAGAT
TCTTCCGTTCAGTCTAAACTGACTGATATAAAGTGTAGTAACGTTGTCTTTAGGCTGTCTCTTAGCATGAATGTC
TCAGCAAATTCAACAGAATGGGCCTATTGTTGACTTGCATAACAAGATCAACTTGTATGACCAGAAAAGCGC
AGGAAATGCTACTTGCTTGTTGGTGGCATTTGTTGCTTAGTAGAAAATAGTGCTTTTGGTTTGATGACTTATTGGAATCCTA
TTTTAATGACAATAGTAGTGTTGCAGAGTATGCTGTTAATAATGGTTCTCCACCTCAGTTGGTTAAGCAATTGCCGCCATGCCATGAATGCA
CGCCAACAGTAGTATGAAGATGCTGTTAATAATGGTTCTCCACCTCAGTTGGTTAAGCAATTGCGCCATGCCATGAATGCTAG
CAAAGAGCGAATTTGACCGTCAGCGTTCTACTCAGCGTAAGCTTGATAGAATGGCGGAACAGGCTGCAGCACAGATGTA
CAAGAGCAAGAGCAGTTAATAGGAAGTCCAAAGTTGTAAGTGCTATGCATTCACTGCTTTTTGGTATGTTGAGACGT
TTGGACATGTCTCTGTAGACACCATTCAACTTGGCAAAGGATGGGGTGTACCTCTGTCGTCATACCGGCAGTCA
GTGCTACTAAGTTACAACATTGTTACTTCTGATATCGATTCTTATAATCGTATCAACCAGCGTGAGGATGTGTCATTACGC
TGGTACCATTTGGAATATATAATTGATATCAAGGACAATGATGGCAAGGTGGTACACGTTAAGGAGGTAACGCACAGAAT
GCTGAGTGCCTGTCATGCCCCCTGGTCCTTGGGCGTGTTCTTGGCTACATAGGTGCCACTAGGTGCCACTACGCTTGCAGGCTACATACAGAAT
AGCTGAAGCAGCGCTCCATTAAGGCAGAAGGAGAATGGCCATAGTTGGAGAAGGTAAGGCACTTTACAATAATGAGGGTGG
ACGTACTTTTATGTATGCTTCATCTCGGACAAACCGACCTGCGGTGTAGTTAAGTGGGAGTTCGATGTGGTTGTAAC
ACTATTGTAGCTAGAACAACCACCACGTAAGTTCTTGGGATTCTCCTATGGTGCACATAGGTGCCACTAGCCTTGCAGGCTGTAAACAAAC
GTAACCTTAACACGTTAACGTAGGGGTGCTGTTCTTGGCTACATAGGTGCCACTAGCCTTGCAGGCTGTAAACAAAC
AGAACAGGCTATTAACTCTTCATTGTGACACTTGCGCTTTGCGCTAAGACCTACATCGATGCTGTC
AAAAGTGGTCACAAACCAGTAGTAACTGCCGTTAAGATGTTGGCCAATGTTCTGTAATGGACAAGCAAGCTGTACTAATG

Fig. 1F

```
GTGTGGAGGCTAGTACTAACCAGGATTCATACCGGTGGTGCTTCCCTGTGTCTATATTGTAGAGCACATGTTGAGCATCC
ATCTATGGATGGTTTTTGCAGACTGAAAGGCAAGTACGTAGCAAGTGCCACTAGTTACAGTGGATCCTATACGTTTGTA
CTTGAGAATGACGTTTGCAAGGTCTGTGGTTGGCTGGCTGTGCACTTGTGACAGATGCCATTATGCAAGCA
CTGATATGGCTTATTTAAACGAGTACGGGGCTCTAGTGCAGTCAGATAGAGCCCGTAACGGTACTGATACACAACAT
GTGTATCGTGCTTTGACATCTACAACAAGGATGTGCTTGTCTGTCAAAGATGTCAAGGTGAACTGTGTTCGCCTGA
AGAATTGGATAAGCATGATGCATTCTATGTTGTCAAACACGATTCTTCACTGGAAGGATGGTCGTCAATCTATGTAAC
TAGCAGACTTGAAAAGTGTGGAGCCGTAGCTGAACTGAACACGATTCTTCTTACTGGAAGGATGGTCGTCAATCTATGTAAC
GTTTGTAGAAAGGATCTTACCGAGTATACTATGATGGCGCTTGTGAGGATTTGTGTACGCTTACGTAACTTTGATGAAAACAATTGCG
ATGTTCTTAAGAGCATTTTAATTAAGGTAGGCGCTTGTGAGGAGTCCTACTTCAATAATAAAGTCTGGTTGACCTGT
TGAAAATGAAGACATTCATCGTGTTTATGCATTGTTAGGTACCATTGTTCACGTGCTATGCTAAATGCGTTAAGTTC
TGTGATGCAATGGTTACTGTTAGCATCAAGGGAATGGGTATAGTTGGGTGTCACATTAGATAATCAGGATCTTAATGGTGATTTTAATGATT
TTGGGTGATTTACTGTTAGCATCAAGGGAATGGGTATACCCATTGCACATCATATTACTCTTATAGATGCTGTTAT
GGGTATGACTAATGCCTTGCTAGTGAGTGTTTGTTAGAGTGATATATTGGTGAGGATTTCAAGTCATATGACCTG
CTGGAATATGATTTCACGGAGCATAAGACAGCATAGTTCACTGTCCAACAAGTATTTCAAGTATTGGGGACTGCAATACCACCCTA
ACTGTGTGGACTGCAGTGATGAGCAGTGCATAGTTGGATTGGATGGTCATACGTGTTTCCACTACTGGTTATCATTTAAA
TACGGCATTTGGACCTTTGTGTGCAAGTGTTGCAACATGACCTCAACTCAGGCTCTCTATTAAACGAACTACTCAGTTTGTA
CAGTTAGGTATAGTTTGGAACAATGACTTCTATAGCATCATCACCAGCCCTTGTGATCAGCGGTACTGTTGTTTCAGTTGCAGCGCTAGG
GTGATCCTGCATTGCTTATAGCACTGTTAAACCTGGCCATTCTAAACCTGGCCATTTCAATAAGGAGTTTTATGACTTCTTACTGAGCAAGGTTC
TACAGGTATGACTAACCAGCTGAGCTGCTTACTTAAAGCACTTCTGTTCTGGACATTTGCCAAGTCGGGTCGTGATGCAGCTGTTAAGGATTTGACT
TTTCTGAGGGCTCTGAGCTGCTTACTTAAAGCACTTCTGTTCTGGACATTTGCCAAGTCGGGTCGTGATGCAGCTGTTAAGGATTTGACT
ACTATAGGTATAATAGACCTACTGTTCTGAACTACTGTTGTATCACTGTTAAAGAAGTGGTGTTACAAACTTAACAAAGAGCGCAGGTTATCCTTGAAC
TATTTACGAAGGTGGTTGTATCACTGCTAAAGAAGTGGTGTTACAAACTTAACAAAGAGCGCAGGTTATCCTTGAAC
AAGTTGGTAAAGCTGGTCTTTACTATGAAGCTCTTTATGAGTCTTTATCCTATGAGGAACAGGATGAACTTTATGCTTATACTAAGCGTA
ACATCCTGCCCACTATGACACAGTCAACTTACTATGAAGCTCTTTATGAGTCTTTATCCTATGAGGAACAGGATGAACTTTATGCTTATACTAAGCGTA
TTCGCTTTGTCAACATGCAGTACTACTAAGTTTATGGTGGTTGGGACAGTATCACCAGAACACCCTTAAGAACCTTATTGATGGTGCGAAATCCGT
GTCTTATGGGTTGGGATTACCCAAGTGCGACAGAGCACTGCCGCCAATATGCTTAAGAACCTTATTGATGGTGCGAAATCCGT
CTCTAAGCACACCACATGCTGCAGTTCCACTGACCGCTTTTCAGGTTGTGCAATGATACGCATGTTCAGCCATGATTCTTACTGAG
GTTGTTATTCAATATCTTCAAGCAGGTTTATTTGAAGCCAGGTGGTACTACCTCTGGTGATGCCAACCACCGCATATGCAAACT
CAGTTTTCAATATCTTCAAGCAGGTAAGTGCCAATGTTAACAAACTTCTTAGTGTTGACAGCAATGTCTGTCATAATTT
AGAAGTTAAGCAATTGCAGCGTAAGCATTTTATGAGTGCGTGTATAGATCAACTACCGTCGATGACCAGTTCGTCGTTGAG
TATTATGGTTACTTGCGTAAACATTTTCAATGATGATTCTTTCGATGATGGCGTTGTTGTTACAACAATGACTATG
```

Fig. 1G

```
CATCACTTGGTTATGTCGCTGATCTTAACGCATTCAAGGCTGTTTGTATTACCAGAACAATGTCTTCATGAGCCCTC
TAAATGTTGGATCGAGCCTGACATTAATAAAGGTCCTCATGAATTTGCTCGCAGCATACTATGCAGATTGTCGATAAA
GATGGTACTTACTACCTTACCCTGATCTTCAAGAATCCTCTGCAGGTGTGTTGTTGACGACGTTGTTAAA
CTGATGCAAGTTGATTGCTTGAACGTTATGTGTCATTGGCTATAGATGCTACCGGTATCTAAGCATGAAACCTGA
ATATAAGAAGGTGTTTATGTGCTTTGGATTGGGTTAAGCACCTGTATAAACTTTGAATGCTGGTGTGTTAGAGTCT
TTTTCTGTCACACTTTTGGAAGATTCTACTGCTAAATTCTGGGATGAGAGCTTTTATGCCAACATGTATGAGAAATCTG
CAGTTTGCAATCGCAGGGCTTTGTGTGTTTGTGGCTCTCAAACTGTTTACGTGTGTGATTGTCTACGGCGTCC
TATGCTTTGTACTAAGTGTGCTTATGATCATGTCATTGGAACAACTCACAAGTTCATTTTGGCTATCACTCCATGTG
TGTTGTGCTTCAGATTGTGGTGTCAATGATGTAACTAAGCTCTACTTAGGTGGTCTTAGTTATTGGTGTCATGAACACA
AGCCACGTCTGCATTCCCGTTGTTCTGCTGGTAATGTGTTTTGGTTTGTACAAAAATTCTGTACCGGCTCACCGA
TGTTGAGGACTTTAATCGCATTGCTACATCCGATTGGACTGAGTGTTCTGACTACAGGTTGGCAAATGATGTCAAAGAC
TCATTGCGTCTATTTGCAGCGGAAACTATCAAGGCCAAGGAGGAGAGCGTTAAGTCATCCTACGCTTGTGCAACTAC
ATGAGGTTGTAGGACCTAAAGAGTTGCTCAAATGGGAAGTCGGCAGACCCAAACCACCTCTTAATAGAAATTCGGT
TTTCACTTGTTATCATATAACGAAGAACACCAAATTCAAATCGGTGAGTTGTGTTGAGAAGGCAGAATATGATAAT
GATGCTGTAACATATAAAACTACCGCCACAACAAAACTGTTCCTGCATGGTTTTGTGCTTACCTCACATAATGTTC
AGCCATTGCGCGCACCGACCATTGCTAATCAAGAACGTTATTCCACTATCACTAAGTTGCACCCTGCTTTTACATACC
TGAAGCTTATTCTAGCTTAGTGCCTATTACCAACTGATTGGTAAGCAGAGATTACAACTATCCAGGGACCTCCAGGT
AGTGGTAAATCTCACTGTGTTATAGGGCTAGTTGTACTATCCAGGTGCACGTATAGTGTTACAGCTTGTCTCATG
CAGCGGTCGATTCACTTGTGTGAAGCCTCACTGCTATAATACTAGTGCTATGACAATGTTCACGCATCATACCACGCGTGC
TCGTGTGAGTGTTATGACGGACATTGTTGTGGGACCCTCTATGTGCACTAATTATGACTTGTCTCATAAATCAGCGCA
GAGTGCAATGGGACATTGTTGGTGATGAGGTTTCTATGTGCACTAAGCTGCCTGCACCAGTGTTATGATTTCACGTGGTACTTT
TCAGTCTATAGGCATGTAGTCTAACAACGTTGTCACTCAACGCATGTGTGCCCTTAAGCCATGTGATGTTTCTTGCACAAGTGTATGC
GGAACCAAAGGACTACAACGTTGTCACTGTGTCTGTGTCTGAGATGTCTATGAAACCAATTCATTCCTGCACCAGATAGCAAGC
AGTGTTTAAAATCTTTGCAAGGGTAATGTTCAGGTTGACAATGGTTCAAGCATCAATCGCAGGCAATTGGATGTTGT
GCGTATGTTTTGGCTAAAAACCCTAGGTGGTCAAAGGCTGTTTTATTCTCTTATAACAGCCAGAATTATGTGCC
AGCCGCATGCTAGGTTTACAAATTCAGACAGTTGACTCATCCAGGTAGTGAGTATGACTATGTCATTTATACACAA
CTTCAGATACTGCCGTGTAATGTTCGTTAACAGGTTAACAGGTTAAATTTTTGAGCTTAAATTGTCTGATTGCAGGCTAATGTGTAT
AATGTGCGATAGGTCCTTTTGATGTGCTTAATTTTTTGAGCTTAACAGTTTGCCACCATCTCACGCTAACACTTCATGTCTTTAGCGGACA
GGTCTTTTTAAAGACTGTAGCAGAGGTGATGATCTTGTTGCCACCATCTCACGCTAACACTTCATGTCTTTAGCGGACA
ATTTTAAGACTGATCAAGATCTTGCTGTTCAATAGGTGTTAATGACCCATTAAATATGACCATGTTATCTCGTTTAT
GGGCTTCCGTTTGATATCAACATACCAACCATCACACTCTCTTTGCACACGGACTTTGCACGCGACTTTGCCATGCAATGTTAGA
```

Fig. 1H

GGTTGGTTGGTTTGACGTTGAAGGAGCACATGTTGTTGGCTCTAACGTCGTACAAATGTCCATTGCAATTAGGGT
TTTCTAACGGTGTGATTTGTGTCAGACCTGAAGGTTGCGTTGTAACGAGTCGTTGTGACTGTACATTAAACCGTCAG
AGTCGTGCTCCACCAGGGGAACAATTTGCACACCTTTGCCTCTACTTAAACGCGCCAACCATGGATGTGGTTCGT
AAGCGTATAGTGCAAATGTAGTGCGTTACTTGTCAAGATTGGACCAAGCAGAGTTGTGATTGTGGTAAGGTTGCTACTTGTTA
TGGAGTTGACAACTATGCGTTACTTGTCAAGATTGGACCAAGCAGAGTTGTGATTGTGGTAAGGTTGCTACTTGTTA
CAATAGTGCGTGCATACGTACGTGTTCAAACATGCCTTGGTGTGATTACCTGTACAATCCATACTGTATTGAT
ATACAGCAGTGGGGATACAAGGGATCACTTAGCCTTAACCACCATGAGCATTGTAAATGTACATAGAAACGAGCATGTGG
CTTCTGGTGATGCATAATGACTCGCTGCTGCTAGCCATACATGATTGCTTTGTCAAGAACGTTGACTGTCCATCACATA
CCCATTTATTGGTAATGAGCGTGTTATTAATAAGAGCGGCCAACCCTAAGGGCATTAGATGTGCCGTAACGGATGCTAAGTGGTTCT
TTATACAATCCAAAGCCATATATGATATTGGCAACCCTAAGGGCATTAGATGTGCCGTAACGGATGCTAAGTGGTTCT
GCTTGACAAGAATCCTACTAATTCTAATGTCAAGACATTGGAGTATGACTATATAACACGGCCAATTTGATGGGT
GTGCTTGTTTGGAATTGCAATGTGGACATGTATCCAGAATTCTCTGTGGTCTGTGGGTTTGACACTCGCTGTAGGTCA
CCACTCAACTTGCCAAGTTGAATGGIGGTTCACTGTATGTTAATAATCATGCATTCCATACACCGGCTTTGACAAGC
GTGCTTTGCCAAGTTGAAGCAATGCCATTTTCTTCTATGATGTAATGTTGGTGGAGCTGTCTGTAGTAAGCATTGTGTATG
CTACGTTCCTCTTAGGCTAGTAATTGCATTACACCTTTACGTGCGGGGCTTTACGATTTGGGTGCCACTCGTTGACACCT
TACCATAGCTATGTTAATGCTTACAACACCTTTAGTAACAACTTGCTTCAATGTCGTAAAGAAAGGATCTTT
ACAATCTGTGGCAGACATTTAGTAACAACTGCAAGGTCTTGAGAACATTGCTTCAATGTCGTAAAGAAAGGATCTTT
TGTTGGGTGCTGAAGGTGAGCTTCCTGTAGCTGTGGTTAATGACAAAGTGCTCGTTAGAGATGGTACTGTGATACTCTT
GTTTCACAAAGACATCCTACGTAACTTGGGTGTTGTTGCACATCTAAGTGTGTCATTGGACTATGAAGCCGAACGTCCACT
CCATTACGATCCTACGTAACTTGGTGTTGTTGCACATCTAAGTGTGTCATTGGACTATGAAGCCGAACGTCCACT
TACTACTTTACAAGGATGTCTGTAAATATACCGACTTTGAGGGTGACGTTTGCACACTCTTGATAACAGCATTGT
AGTTCATTAGAGCGATTCTCTATGACCCAAATGCTGTATGTCACTTACAGCTGTTAAAAGTTACTGGCATAA
AGTTAACTTATGGTTATCTTAATGGTGTCCCAGTTAACACACATGAACACATGAAGATAAACCTTTACTTGGTACATTTACACTAG
GAAGAACGGCAAGTTCGAGGACTATCCTGATGGCTATTTACCCAAGGTAGAACAACCGCTGATTTAGCCCTCGTAGT
GACATGGAAAGGACTTCCTAAGTATGGATATGGGTCTGTTATTAACAAGTACGGACTCGAAGATTACGGCTTTGAGC
ACGTTGTGTATGGTGATGTTTCTAAAACCACCCTTGGTGGTTACATCTACTAATTTCCAGGTGCGTCGGCCTGTAT
GGGTGTGCTTAAATAGACGAGTTGTGTCAGTTGGTCTAGTAATGATAGCACGTTAAGTCTGTTACATATGCTGATAAC
CCTAGTAGTAAGATGGTTTGCACGTATATGGATCTCCTTCTTGACGATTTGTCAGCATTCTTAATCGTTGGATTGA
GTGTTGTATCTAAAGTTCATGAAGTTATGTGAAGTTATGGTCGAGGTGGATGTGTGGGTGTAAGGATCATAAACT
CCAGACATTATCGCAACTTCAGGCCAGTGAATGGAAAGTTGGTTATTCCATGCCTTCTATTACAAGATACAACGT
ATGTTTAGAACCTGCAATCTCTATAACTTAACTATGGTGCTGGTATTAAGTTACCTGATGGCATTATGTTAACGTAGTTA
AATATACACAGCTTTGTCAATATCTTAATAGCACCACAATGTGTACCCCATCACACATGGCCGGTGCTACATCTTGGTGC

Fig. 1H

```
TGGCTCCGACAAGGGTGTTGCACCTGGCACGGCTGTCTTACGACGTTGGTTGCCACTGGATGCCATTATAGTTGACAAT
GATAGTGTGGATTACGTTAGCGATGCTGATTATAGTGTTACGGGAGATTGCTCTACCTTATACCTGTCAGATAAGTTG
ACTTAGTTATATCTGATATGTATGATGGTAAGATTAAAAGTTGTGATGGGAGAACGTGTCTAAAGAAGGCTTCTTTCC
CTATATTAAATGGTGTCATCACTGAAAAGTTGGCACTTGGTGTAGTAGTTAAGGTGACGGAGTTAGTTGGAAT
AGAAGTTGTATGAACTCATTCAGAAGTTGAGTGATTTGCAAGTGGCGCTGTGATTGACGGCAACACTAGTCATGCCAATTA
CATTTTAATTGGTGTTCACTATTTAGGTGATTTGCAAGTGGCGCTGTGATTGACGGCAACACTAGTCATGCCAATTA
TATCTTCTGCGGTAATTCCACATATGACTATGTCTTACAATAGTGTACTTGATTTAAGCAAGTTCAATTGTAAGCAT
AGGCTACAGTTGTTATTAATTAAAAGATTCATCCATTAGTGATGTTGGTCAAGTAAAACAAATGAAGTCTTAAATTACTTC
TAGTGCGTAATAATGACGCCATTTGTGGTTTTCTAAACACTTCAACGTAAAACAAATGAAGTCTTAAATTACTTC
TGGTTGTTCTTACCAGTTACTTCAAACACTTCAACGCCTACCACAAGAGTCACTAGTTGCCAGTCCACTATTAACTTCAGGC
GGTTCTTTTCAAATTAATGCAGGCACTGCTGAAACTGTCTAGTGGCGTGCATGGTATTTCCTCAGTACATCGATGCTGGTCAGGGC
CTGGTACTGTGGCACAGGTCTGAAACTGTCTAGTGGCGTGCATGGTATTTCCTCAGTACATCGATGCTGGTCAGGGC
TTGAGATTGGCATTCACAGGACGCGTTTGATCGTAGTGGTTACCAGCTTATTTACATAAGGCCACTAATGGTAACC
ATAATGCTATTGCACGACTGCGCATTGCCAGTTCCAGATAATAAACATTGGCCCTACTGTTAATGATGTTACAAC
AGGTCGTAACTGCCATTCAACAAGCCATTCAGTTGCTGACAAGATCTATCATTTTATCTTAAAATGATTGGTCCGTGTTGCGACAA
GACAATGATCGTGTCACTGTTTTTGCTGACAAGATCTATCATTTTATCTTAAAATGATTGGTCCGTGTTGCGACAA
GATGTTACAATAAAAGAAGTTGTGCTATGCAATATGTTTATACACCTACTACTGCTTATGTTACTAGTGCAGG
TGAGGATGGCATTTATTATGAACCATGTACAGCTAATTGGTTCCAATGGTACGCTGCCAATGTGTTTGCCACTGATTCTAAT
GGCCACATACCAGAAGGTTTTAGTTTTAATAATTGGTTTCTTTGTCCAATGATTCCAACTTTGTTGCATGGTAAGGTGG
TTTCCAACAACCTTTGTGTCAATTGTCTTTGGTCATTGTAAGGAGCTGCTGCCGCAGAGGCTCTGAGGTTTAATATTAATGACACC
TCAAACGATGGATGGCGTTTGTAATGGAGCTGCTGCCGCAGAGGCTCTGAGGTTTAATATTAATGACACC
TCTGTCATTCTTGCTGAAGGCTCAATTGTACTTCATACCTCTGGGTGTACTACCCAAGTGCTTAGGAACAAATCTTCTTTTTTGTTTGCAGTAATTCTT
CAGATCCTCATCTAGCTACCTTCGCCATACCTCTGGGTGTACTACCCAAGTGCTTAGGAACAAATCTTCTTTTTTGTTTGCAGTAATTCTT
TACAACTCCACTGTTATAAATTTTTGGCTGTGTTTACCTCTACCGTCAGGAAATTGTCATCCAAGTATGGTGAT
GTTATGTCAATGGTTTGGATATCGCATCGGTTGTTGATGCGTCACAATTAATTTCACTGGTCATGCACTG
ACGATGATGTTTCTGTTTTGGACCATAGCATGGACTAATTTTGTTGATGCACTAATTGGCACTCAGGAACCGCCAT
TCAGCGTATTCTTTATTGTGATGATCCTGTTAGCCAACTCAAGTGTCTCAGGTGCTTTGACCTTGACGATGGTTTT
TACCCTATTCTTCTAGAAACCTTCGAGTCATGAACAGCCAATTCTTTGTTACTCTGCCATCATTAATGATCATT
CTTTTGTTAACATTACTGTATCTGCTCCTTTGGTGGTCACTAGTGGTCATAGTGGTCCAACCTTATTGCATCGTTTATAACGTTACACTACTATCAA
TGGGTTTAGTTCTTTCTGTGTTGACACTAGACAATTACCATTTCACTGTTTTATAACGTTACAACAGTTATGGTTAT
GTGTCTAAATCACATTCACAGGACAGTAATTGCCCTTTCACCTTGCAATCTGTTAATGATTACCTGTCTTTAGCAAATTTGTG
TTTCCACCAGCCTTTGCCTGTAGTGCCTGTAGTCTTTTTGGTTACCCTGAGTTTGGTGTAGTGGTGTTAAGTTTAC
```

Fig. 1J

GTCCCTTTACTTCAATTCACAAAGGGTGAGTTGATTACTGGCACGCCTAAACCACTTGAAGGTGTCACGGACGTTTCT
TTTATGACTCTGGATGTGTGTTATTACACATTCTGATTCTGGACAGTTGTTAGCCTTAAGAATGTCACTAGTGGTGCTGTTTA
GCTTTTTGGCAGGTGTTATTACACATTCTGATTCTGGACAGTTGTTAGCCTTAAGAATGTCACTAGTGGTGCTGTTTA
TTCTGTTACGCCATGTCTTTTTCAGAGCAGGCTGCATATGTTGATGATATAGTGGGTGTTATTCTAGTTGTCT
AGCTCCACTTTAACAGTACTAGGGAGTTGCCTGGTTCTTCTACCATTCTAATGATGGCTCTAATTGTACAGAGCCTG
TGTTGGTGTATAGTAACATAGGGTGTTTGTAAATCTGGCAGTATTGGCTACGTCCCATCCAGTCGCCCAAGTCAAGAT
TGCACCCACGGTTACTGGGAATATTAGTATTCCCACCAACTTAGTATGTTGTAATGGTAATTAGGACAGAATATTACAGCTTAC
AACACGCCTGTTAGTGTTGATTGTGCCACATATGTTTGTAATGTTAACTCTGTTGTAAACAATTACTCACCAGTACA
CTGCAGCATGTAAGACCATAGAGTCAGCATTACAACTCAGCGCTAGGCTGAGCTGTGAAGTTAACTCTATGCTTAC
TATTTCTGAGAGAGGCTCTACAGTTAGTACAGTTCGTTAATGGTGATGGATATAATTTACTAATGTGCTGGGT
GTTTCTGTGTATGATCCTGCAAGTGGCAGGGTGTACAAAAAGGTCTTTATTGAAGACCTGCTTTTAATAAGTGG
TTACTAATGGCCTTGGTACTGTTGATGAAGACTATAAGCCGTGTTCTAATGGTCGCTCTGTGGCAGATCTAGTCTGTGC
ACAGTATTACTCTGGTGTCATGGTACTGTGTCATGGTGTGTGACGCTGAGAAGCTTCACATGTATAGTGCGTCTCATC
GGTGGTATGGTGCTAGGAGGTTTACTTCTGCAGGCATTGCCTTTAGCTATGCTGTCAAGCTAGACTCAATTATC
TTGCTCTACAGACGGATGTCTACAGCGGAACCAGCAATTGCTTGCTGAGTCTCTTTAACTCTGCTATTGGTAATAAC
TTCAGCCTTTGAGAGTGTTAAAGAGGCTATTAGTCAAACTTCCAAGGTTTGAACACTGTGGCTCATGCGCTTACTAAG
GTTCAAGAGAGGTTGTTAACTCGCAGGGTGCAGCTTTGACTTGGACATTCTTCAGCGATGTTCAGGTTGACCGTCATCACCGGCAG
CTAGTTCTATTGATGACATTACTCTCGACTGGACATTCTTCAGCGATGTTCAGGTTGACCGTCATCACCGGCAG
ATTATCAGCACTTAATGCTTTGTTGTCTCAAACCCTCACTAAGTAGTATACTGGTTTTGTGGTGATGGCGAGCACATTTCTCTC
CAAAGGTTAATGAGTGCGTTAAATCGCAATCTCAGCGTTATACATACAGTAGTGTACTGTACCGAGTGATTTTGTAGATGTTATTGCCAT
TGGTACAGGCAGCACCTCAGGGCCTGCTGTTTTACATACAGTAGTGTACTGTACCGAGTGATTTTGTAGATGTTATTGCCAT
CGCTGGCTTATGCGTTAACGATGAAATTGCCCTGACTCTACGTGAGCCTGGCTTAGTTCTTGTTACGCATGAACTTCAA
AATCATACTGCGACGGAATATTTGTTTCATCGCGACGTATGTTTGAACCTAGAAAACCTACCGTTAGTGATTTGTTC
AAATTGAGAGTTGTGGTCACCTATGTCAATTTGACTAGAGACCAACTACCAGATGTAATCCCAGATTACATCGATGT
TAACAAAACACTTGATGAGATTTTAGCTTCTCTGCCCAATAGAACTGGTCCAAGTCTTCCTTTAGATGTTTTAATGCC
ACTTATCTTAATCTCACTGGTGAAATTCACAGAATTGCAGATTAGAGCAGCGGTTCAGAGTCTCTCCGTAATACTACAGAGGAGCTCC
AAAGTCTTATATATATATAAATCAACACACACTAGTGACCTTGAGTGGCTCAACGAGTTGAGACTTGAGACATATCAAGTGGCC
GTGGTGGTTTGGTTGATTATTTTCATTGTCGTGTGTTCATTACTACAGTGTTCTGCTGCATTCCACGGGT
TGTTGTGGATGCGGCTGCAGTGCAGTGATGTTTCTTGGACGTTTTCATTGTAGGGTCCTAGACTTCAACCTTACGAAGTTT
TGAAAAGGTCCAAGTCAGTGCAGTGATGTTTCTTGGACGTTTTCATTGTAGGGTCCTAGACTTCAACCTTACGAAGTTT
TCTGCTAACTTGTCTTTGGATGCTGTCCAAGAGTTGGAGCTCAATGTAGTTCCAATTAGACAAGTTCAAATGTGACGG
GTTTCTTTCACCAGTGTTTTATCTACTTCTTGCACTGTTTAAAGCGTCTTCTTTGAGGCGCAATTATTATTGTT

Fig. 1K

GGCAGGCGGTTTGCTGTCATTGTCTTATTGCCCACTTTATATTATTGTGGTGCATTTTAGATGCAACTATTATT
TGTTGCACACTTATTGGCAGGCTTGTTAGTCGTGCTTTACTCCTGGCGTGCTTTTATTATATTAAAATGCGCTCTTTATTATTTTA
ATACTACGACACTTCTTCCTCAATGGTAAAGCAGCTTATTATGACGGCAAATCCATTGTGATTTTAGAAGGTGGTGA
CCATTACATCACTTTGGCAACTCTTTGTTGCTTTTGTTAGTAGCATTGACTGTATCTAGCTATACGTGGGCGGCAA
GAAGCTGACCTACAGCTGTTGCGAACTGTTGAGCTTCTTGATGCATGCAAGAGTATGCTACAATTAGTGAAGTCTTTCGCACATCAAATTG
TGGCATTACTTACTGCTGCATTTGACTTCAATTCAACTAGACGAGTATGTCTACAATTAGTGAATGATAATGGTCTAGTAG
TAATGTTATACTTGGCTTTTCGTACTCTTTTCCTGCTTATTATAAGCATTACTTTCGTCCAATTGGTTAATCTGTG
CTTCACTTGTCACGGTTGTGTAATAGCGCAGTTTACACACCTATAGGGCGTTTGTATAGAGTTTATAAGTCTTACATG
CAAATAGACCCCCTCCTAGTACTGTTATTGACGTATAAACGAAATAGTCTAACGGTTCTATTCCCGTTGATGAGGTG
ATTCAACACCTTAGAAACTGGAATTTCACATGGAATTTCATAGATGGCTATTCTATGGATACTTTGGCCTCTCTGTTAGCACTGTCACT
ACAAGTACTCTGCGTTCTTGTATGGTGTCAAGATGGGTCTTTTTGCTTTCAGCATCCTATGGCTTGCATCACTCTTATG
TTTGATGCATGGGCTAGCTTCATGTCAATAGCATTCGGTTGTGGGCGCAGGACACAGGTCTGCATTCCAGTGCTTGGAGCACCAAGTGGTGTAAGCGTAAC
ACGCGCTTCTCACTTCTGTGATGGGCCGACCAGGTCTATAAGGTTGCTACTGGCGTACAGGTAAGTCAATTACCTAATTTCGTC
ACTCCTTAGTGGTACATTGCTTGTAGAGGGTATAAGGTTGCTACTGGCGTACAGGTAAGTCAATTACCTAATTTCGTC
ACAGTCCAAGGCCACTACAACAATTGTCTACGGACGACTACTCAGTGTGACGCGTGTTGTTGTCAGTCAATGCTTCATCTGGCACTGGTTGGG
CTTTCTATGTCCGGTCCAAACACGGCGACTACTCAGTGTGACTAATCCGAGTTCGGTTCTCACAGATAGTGAGAAGT
GCTTCATTTAGTCTAAACAGAAAACTTTATGGCTTCGTCAGTTTTCAGGATCGTGGCCGCAAACGGGTGCCATTATCC
TCTATGCCCCTCTTAGGGTTACTAATGACAAACCCTTTCTAAGGTACTTGCAAATAATGCTGTACCCACTAATAAGG
AAATAAGGACCAGCAAATTGGATACTGGAATAACTGGAACAATTCGCTGGCCATGCCCCGTTGGTGAGCGAATTGAACAACCT
TCCAATTGGCATTTCTACTACCTCCGGAAACAGGACCTCACGCAACCTGGGTGTCAGAAAGGCGTTAGGACTCGTACTGAGGGTGTTTCT
GGGTTGCTAAGAAGGGCAAAGAGTGAACCACTAACCTGGGTGTCAGAAAGGCGTTGAAAAGCCAATTATTCCAAA
TTTCTCTCAACAGCTTCCCAGCGTAGTTGAGATTGTTGAACCTAACACACCTCCTACTTCACGTGCAAATTCACGTAGC
AGGAGTCGTGTAATGGCAACAACAGGTCCAGATCTCCAAGTAACAACAGAGGCAATAACCAGTCCGCGGTAATTCAC
AGAATCGTGGAAATAACCAGGTCGTGGAGCTTCTCAGAGAACAGAGGCAATAATAACAAGGCGTAACAAGTCTCGTAA
CCAGTCCAAGAACAGAACCAGTCAAATGACCGTGGTTGTAACATCACGGATGATCGGTGCTGTCGTCAAGGAT
GCCCTTAAATCTTGGGTATTGGCGAAAACCCTGACAAGCTTAAGCAACAGCAGAAGCCAAACAGGAAAGGTCGACA
GCAGCGGCAAAATACACCTAAAGAAGAACAAATCCAGAGCCACTTGAAAGAAGAACGTGACCTCAAGAACATCCAGAGTG
GAGGAGAATTCCAAGGGCGAAAATAGGGCGAAAATAGCCTGCTTGGGACCCAGGAGGCTTCAAAAATTTGGAGATGCG
GAATTTGTCGAAAAGGTGTTGAYGCCTCAGGCTATGCTCAGATCGCCAGTTAGCACCAAATGTTGCAGCATTGCTCT
TTGGTGGTAATGTGGCTTCTGTGAGCTAGCGGACTCTTACGAGATTACATATAATTATAAAATGACTGTCCAAAGTC
TGATCCAAATGTAGAGCTTCTTGTTTCACAGGTGGATGCATTTAAAACTGGGAATGCAAAACCCCAGAGAAAGGAA

Fig. 1L

AAGAAGAACAAGCGTGAAACCACGCAGCAGCTGAATGAAGAGGCCATCTACGATGATGTGGGTGTGCCATCTGATGTGA
CTCATGCCAATTGGAATGGGACACAGCTGTTGATGGTGGTGACACGGCCGTTGAAATTATCAACGAGATCTTGACAC
AGGAAATTAAACAATGTTTGACTGTCCCAGGGTAGTGCCATTACACTGTATTACTGAGTGTT
TTTTAGGACTTGGCTGCTGGGCTATGGCCTCTAACTAGCGGTCTTGGTCTTGGTCTTGCACACAACGGTAAGCCAGT
GGTAATGTCAGTGCAAGAAGGATATTACCATAGCACTGTCATGAGGGAACGCAGTACCTTTCATCTAAACCTTTGCA
CGAGTAATCAAAGATCCGCTTGACGAGCCTATATGGAAGAGGCGTGCCAGGTATTTGACTCAAGGACTGTTAGTAACTGA
AGACCTGACGGTGTTGATATGGAT

Fig. 2A

USA/Iowa23.57/2013 (SEQ ID NO:2):

CTACGGATAGTTAGCTCTTTTCTAGACTCTTGTCTACTCAATTCAACTAAACGAAATTTGTCCTTCCGGCCGCATGT
CCATGCTGCTGGAAGCTGACGTGGAAATTCATTAGGTTGCTTAAGTAGCCATGCAAGTTGCTGTGCTGTCCTCAGTT
CCTGGTTGGCGTTCCGTCCGTCCCTTCTACATACTAGACAAACAGCCTTCCTCCGGTTCCGTCTGGGGTTGTGGATAAC
TAGTTCCGTCTAGTTGAAACCAGTAACTGTCGGCTATGGCAACCATGTACATTGGCTTTGCCAATGATGCAG
AAATTTCAGCTTTGGCTTTTCGTGTCCTTCGATCTGCTGACACTGTTGAGGGATTGCTTCCGAAGACTATTCTGAGGCGCCGCCTAGTGGATTTATGCA
ATGCCGTTCGTGTCCTTCGATCTGCTGACACTGTTGAGGGATTGCTTCCGAAGACTATGTCATGGTGGTCGGC
ACTACCAAGCTTAGTGCGTATGTGGACACTTTGGTAGCCGCCCAAAAACATTTGTGGTTGGCTGTATTTTCTAACT
GTAATTACTTCCTCGAAGAGTTAGAGCTTACTTTTGGTCGTGGTGGTAACATCGTGCCAGTTGACCAATACATGTG
TGGCGCTGACGGTAAACCTGTTCTCAGGAATCCGAATGGGAGTATACAGATTTCTTTGCTGACTCCGAAGACGGTCAA
CTCAACATTGCTGGTATCACTTATGTGAAGGCCTGGATTGTAGAGGCGATGGATCGGATGTCTCTTATGCAGTCAGAATTTAA
CATCTATTAAGTCTATTACTTACTGTTCAACCTATGAGCATACTTTCCTGATGGTACTGCCATGAAGGTTGCACGTAC
TCCAAAGATTAAGAAGACTGTTGTTCTATCATTAAGAGACCAAGTGTTCCTCCACGCTTTGTTAAGTGTAAGTGTAGTTATC
AATGGGAGCGATGCTCGTTCTACATTAAGAGACCAAGTTCCTCCACTGCTTTAAGTGTAAGCCAGTCCTTGTGGCTTCAT
ATTGGACTGTTGGTGATGGACTTCCTATGTCTCCCACTTGCTGTGCTGGCACTGACTGTTAAGTATTACAACATGTTCCTG
CTCTGCTACGCCTGGTTACGCGCTGGCATTCTGCCAATTCTCAGGTGCAGTCAAGACTCCAAGACGACCTCGCTTGCTCTG
CGCCATGCTGCAGACATTGATGGTTGGCATTCTGCCAATTCTCAGGTGCAGTCAAGACTCCAAGACGACCTCGCTGCTCTG
GTAAATTCCTTGAACACCATGAGGAAGGTTTCACAGATCCTTGCTACTTTTTGAATGACTCGAGCATTGCTACTAAGCT
CAAGTTGACATCCTTAGTGACAAGTTTCTGATGGCCAAGTTTCTGATGAAGTCAAACAAGCTATCTTTGCTGGTCATGTTGTTGGCAGC
GCGCTCGTTGACATTGTTGACGATGCACTGGGACACTGGGGACAGCCTTGGTTTATACGTAAGCTTGGTGACCTTGCAAGTGCAGCTT
GGGAGCAGCTTAAGCTGTCGTTAGAGGCCTTAACCTCCTGTCTAACCTCCTGTCAGCCGAAGTGCCTGAGAAGTTGGCTGCGGGCTGTTACAGTT
TGCCACTCTTAGTATCGTTAACGGTGTTTTTGAGTCGCCGTGACGTGCCTGTGACGTGCTTAAAGGTGGAGGTAAAACCTTTAAACAAGGTTG
TTTGTCAACTTCGAATCGTCTTTTTGACAACGCATTGGTTAAGCTTGTTAAGGCTGTCAAGGCAAAGGTTCCGGCCCACGACAGCCAGGTGTTTG
GCTCTTATGTCTTTTTGACAACGCATTGGTTATTGGGAGTACTACCAAGGTGGTTCCAAGCGCGTTGAAAATGCCAATGTGAAT
TGAAGTTCGTTACACAAGCCTTGTTATTGGGAGTACTACCAAGGTGGTTCCAAGCGCGTTGAAAATGCCAATGTGAAT
CTCGTCGTTGAGGAGATGTGACCCTCAACACCACTGGT

Fig. 2B

GCACCTTACATATCACAGCACCAAGTTATATGGAGGATGCTGCTAATTTTGTAGACCTCTGTACCAAGAACATTGGTAC
TGCTGGTTTCATGAGTTTACATTACGGCCCATGAACAACAGGATCTGCAAGGATCTGTAACCACTTGTTGCACGATG
TCAGGTTTTGAGTGTTTGTTTATGCCTATAATCCACAGTGTCCAGCAGTGTCCAGCAGTGCTGAAGAGATTGATGGTGGTAGCATCTGGC
GGTCTTTATCACTGGTCTTAATACAATGTGGGATTTTGCAAGCATCTAAAGTCAGCTTTGGACTAGATGGCATTGT
TGTCACTGTAGCACGCAAATTTAAACGACTTGGTCTCTCTTGGCAGAAATGTATAACACTTACCTTCAACTGTGGTG
GAAAACTTGGTACTGGCCGGTGTTAGCTTCAAGTTGCCTTCCAGATTCCTGTCCAGCAGGCATTGAGAAGTTAAAGTCTTCCTTAA
ACAGTGTTAAAGTGTTCTGCACGCGTCATTGAACTTCTTTGTGGAATTAGAAGAGAGACATTAAACCACCAGCA
CTGTGTTCACCCTGTCTATTGCTATTGTGATGCTTTGCTATTGATGCTTTGCTTTCTATTATGATGAACACTATACTATCCCACGATGTAATA
CTCAATGGTAGTAGTTCCCCTGAATTTGAGTTCGAGACTCGAGACTCGATGAAGAACTATCTGTTAGAACCATTGAA
GTGTTGTGCCTATTIGTTTAAGAAGAAGGGTGGTGATGTCAATTCTCTGATGAGTCTCTGTTAGAACCATTGA
CCCAGTTTATAAGGTCTCCCTTGAATTTGAGTTCGAGACTATTATGGCTGTGCTAATAAGGCTGTGGTAAT
CGTATCAAGGTTACAGGTGGTGGACGATGTTGTGAGTATATCAAGGTTGCCATTGAGGTCTTAAAGATCATATCG
ATGTGCCTAAGTACTACATCTATGATGAGGAAGGTGGCACCGATCCTAATCTTCCCGTAATGGTTTCTCAGTGGCGTT
GAATGATGACACGATCTCACAGATCTGCTTGATGTGGAAGTTGTTACTGATGCACCAATTGATTTCGAGGGTGATGAA
GTAGACTCCCTGACCTGATAAGGTGGCAGATGTGGCTAACCTGAGCCTGAGGATGGTCCTAATGTAGCTCCTG
AACAAATGTAGAGTCTGAAGTTGAGGAAGTTGCCGCAACCTGTCTTATTAAAGATACACCTTCCACAGTTACTAA
GGATCCTTTGCTTTGACTTGCAAGCTATGGAGGACTTAAGGTTTAAGACAATCTCATAACAACTGCTGGTTACT
TCTACCTTGGTGCAGTGCAAATGCTATGAGCCATCGTTGATGACCTGGGGATCGTTGATGTGCTGTGGATCGGGCTTGCTAGAGTCCCT
CAATGGTTCGCAAATGCTATGAGTCACAAGATTACCTGTTCTGTCAGTAGTAGTCCTGGTGTGGTACTGGTGAACGTATCTATGAGGGT
GACTAAGGACCTACACACACTTAAGATTCGTGAACCGTTCCATATGGTCCATATGTCCAGATACTACTGCTCTCTCCTTGGATTCTTGGTTGATGCACA
TGTGCTTTTCGTATGAGCCAACTTGGAACCGTTCCATATGGTCCAGATACTACTGCTCTCCCTTGGATTCTTGGTTGATGCACA
CTTTTAAAAGTATTGTTGCACCGGCACACTTTTATAGGCAAGGACAGTGGTCATTATGTCACTAACTTTATGATGCTATGCTATTGAT
TCTTTGTGCGGCTGCTTTTATAGGCAAGGACAGTGGTCATTATGTCACTAACTTTATGATGCTATGGCTATTGAT
GGTTATGGTCGTCATCAGATAAGTATGGAGCCTGTATTGGAGCCTGTGTCAAACCGGTTCATTCTTAAGACGTTAATTGGACAGCACCTTTG
TCCCAGACCGTTGAGCCTGTATTGGAGCCTGTGTCAAACCGGTTCAATGCTGCAAATGAGAATTGTCTCACGGTGCGCATA
TTTAGTGACCTGTTAAACTTCCATGTGACTTTGTTGTCAGAAGTGCATGTTGCAGAAGTGCTGAATGATTACATTAAAGCACACGGTCCATTA
GCAAAGGCCATTGATGTTATACCAAGGGCATGTTGGAGGCATTAGGTCTTAAGGTCTTTAATGTGTTGGTCACGTAAGCATGC
AAGTTGGACGTGGGTCATGTTGGAGGCTTATAAGTCCGTTTTGCTAATTCAGGTGTTGCTCTTACACCTTGATTAGTGTTGGA
ACCTGAGCTTCTGTTAAGGCTTATAAGTCCGTTTTGCTAATTCAGGTGTTGCTCTTACACCTTGATTAGTGTTGGA
ATTTTAGTTGTTCCTTTGGAAGAATCTTATCTGCTTTCTTCTGCATGTGTTGGTGATCGCCACTGTAAGTGCTTTGTT
ATAGTGACAAAGAGGCGAGGCGAGGATGATCATTAATTACATGATGGCTTGGTAGATGCTATTTCAAGATGCACTGTTGA
TACTACTCCTGTCCAGGAAGATGTTCAACAAGTTCACAAAAACCAGTTTGCCTAATTTGAACCTTTCAGGATTGAA

Fig. 2C

GGTGCTCATGCTTTCTATGAGTGCAACCCTGAAGGTTGATGTCATTAGGTGCTGACAAGCTGGTGTGTTACAAATT
CCAATTTGGATTTTTGTAGCGTTGGTAAGTGCTTAACAATGTGACTGGCGGTGCATTGCTTGAAGCCATAAATGTATT
TAAAAGAGTAACAAAACAGTGCTGCTGGCAACTGTGTTACTTTTGAGTGTGCAGATATGATTTCTATTACTAGGTA
GTATTGCCATCTGACGGTGATGCTAATATGACAAAATTATGCACGCGCCGTCGTCAAGGTATCTAAGCTTAAAGGCA
AGTTATTGCTGCTGGTTGGGTGGATGCTATGTTGTATTCCAAGTTGTCCACCTCAGCGTGTTAGGTTCGTATCCACAC
TGATGATGTGGAGCGTTTCTACGCAAATAAGAGTGTGGTTATTAAGTACTGAGGATACACGTAGTGTTAAGACTGTT
AAGTAGAATTCCACTGTACTTATTGGACAACAATTGGACCCTGTCTTGTTAATGACACCGTTGTCACAGACAACAAAC
CTGTTGTTGCTGATGTGTAGCTAAGGTTGTACCAAGTGCTAATTGGGATTCACATTATGTTTTGATAAGGCTGGTGA
GTTCCACATGCTAGACCATACTGGGTTGCCTTTCCTAGTGAAGTTGTTAACGGTAGGCGTGTGTTAAAACCACAGAT
AATAACTGTTGGGTTAATGTTACAATTGGCTAGATTTAGGTTCAAGTCAGCAGGTCTACAGGCTA
TGTGGGAGTCCTATTGTACTGGTGATGTTGTGCATTGGTTGTGTCATTGGTTGTACTGGCTTACTGGTGTTGACAAAGGTCA
GCCTAGTGATTCAGAAAATGCACTTAACATGTGTCTAAGTACATTGTTCCTGCTGGTCTGTCACTATTGAACGTGTC
ACGCATGACGGTTGTTGTAGTAAGCGTGTTGTCACTGCACCAAGTTGTGAATGCTAGCGTGTTGAAGCTTGGCGTCG
AGGATGGTCTTTGTCCACATGGTCTTAACTACATTGACAAAGGTGTTGTAAGGTACTACAATTGTGTCAATGT
TGGAAAACCTGTAGTGGCACCATCGCACCTCTTCTAAGGGTGTGTTCCTACACAACATTCCTAGATAATGGTAACGGT
GTTGCCGGCCATTATACTGTTTTGATCATGACACTGGTATGGTGCATGATGGTGTTCCAGTGATCTCA
ATGTCTCCTGTTACAAATGTGTCCTCCAGAGCAGACGGCTGTTGTGATTAAAGACCCTGAAGAAGTAGAGTT
AGACGCTACAAAGCTGTTAGACACTATGCATGGAAAGATTCTTTCCTTGGTGATTTATGTCACGTAAT
TTAATTACAGTGTTTTTGTACATCCTTAGTATTGTATTGCGTAAAAGTGTGCGCTATATTGCGCTTGGGTGTCTCTT
TAGCTGGTGTACCCCAACGTACAAGTTATTGGTTCAAGTTCTTGGTAAGTTTAGTTGGTAGTTGTCAAGCTTATGCATTCATG
CAAGCTAAAACTTTACACGCTTTACACCTATAGGTGGCCCTGTTGTGATGTGTTGTATGTGTTATTCTAGTTTTGACAAGA
ACAATACGGCTTTACACCTTTACACCTATAGGTGGCCCTGTTGTGATGTGTTGTATGTGTTATGCTAATTCTAGTTTTGACAAGA
ATGAGTATTGCAACAGTGTTATTTGTAAGGTCTGTCTCTATGGGTACCAGGAACTTCGGACTTCTCTCACACAGGT
AGTATGGCAACACCTTAGAGACCATTAATTGGTAATGGTAAGACCCTTTCTTTATTTGATGCCTTTCTTTATTTGGCATTTCTGGCAATTTCTGGG
GGTGTTTATGTAAAGGCTATTACTCTCTATTTATTTTCCAGTATCTTAACATACTGGTGTGTTTTCATCGTTACACGCGT
AGTCCATTGGTTTTTGCAGCTTGTCCTGGCCTTTGATGTCTTTGGTGACGAGATCGTCGTCTTTCATCGTTACACGCGT
ATTGATGTTCCTTAAGCATGTTTCCTTGGCTGCGATAAGGCATCTGTGTGGCTTGCTGTCTAAGAGTGCTCGCCTTAAG
CGGGTTCCTGTCCAGACTATTTTCAGGGTACTAGGGTACTAGCAAATCCTTCAGTAGCAATGGTGGTTCTAAGTTCTGTA
AGAAGCACAAATTCTTTGTTTAAATTGTGATTCTTATGGTCAAGGCTGCACTACTATCTTATTAATGACGTCATTGCAACTGA
AGTTGGTAATGTGTCAAACTTAATGCAACCGACAGGTCCTGCCACTATTGACAAGGTTGAATTCAGTAAT
GGTTTTTACTATCTTTATAGGTGTGACACATTTTGGAAGTACAACTTGACATAACAGATAACAATACACTTGCAAAG
AGTCACTTAAAAATTGTAGCATAATCACAGACTTTATTGTTTTAACAATAATGGTTCCAATGTAAATGGTAAGTAAGAA

Fig. 2D

TGCATGTGTGTATTTTCACAGATGCTTTGTAAGTCTGTTAAGTTAGTGGACTCAGCGTTGTTGGCCAGTTTGTCTGTT
GATTTTGGTGCAAGCTTACATAGTTGCTTTGTTAGTGCTTTGTTAGTGTGTTGTCGAATAGTTTGGCAAAGACCTGTCAAGTGTAATG
ACATGCAGGATTGCAAGAGCACATTGGGTTTGATGATGTACCATTGGATACCTTTAATGCTGCTGTTGCTGAGGCTCA
TCGTTACGATGTCCTCTGACTGACATGCATGCGTTCAACAATTTACCACCAGTAGTTCAACCAGAGAAAAACTTCC
GTCCATGACATTGCCACGTGTATGCGGTAGGTGCCAAGATTGTAATCATAACGTTCTTGTCAAGGATAGTATACCTG
TGGTGTGGCTTGTAGTGATTTCATTGCCCTTTCTGAAGAAACTAGGAAGTACATTATTCGTACGACTAAAGTTAAGGG
TATAACCTTCATGTTGACCTTTAATGATTGTCGTATGCATACTACCATACCTACGTTGCATTGCAAATAAGAAGGGT
GCAGGTCTTCCTAGTTTTTCAAAGGTTAAGAAATTCTTCTGGTTTTGTGTCGTTCATAGTTGCTGTTTCTTTGCAC
TAAGCTTTTTTGATTTTAGTACTCAAGGTTAGCAGTGATAGTAGTGATTATGACTTCAAGTATATTGAGAGTGGCCAGTTGAA
GACTTTTGACAATCACTTAGTTGTGTGTGCATAATGTCTTAGTAACTTCGACCAGTGGCATGATGCCAAGTTTGGTTTC
ACCCCGTCAACAATCCTAGTTGTGTCCTATAGTCGTTGGTGTATCAACACCAGTGTTACATTTGGTACATCTGGTTCTGCTTTGATGCTAG
GTGTTTATTTAGCTGGTAAACACTTGTTTTTGCTATTAATTCGGCTTGCACCACATTATCTCGGTTTGGGTGAACTGCTGTCTAC
TGGCGTTGCTGATAAGGGCGCTTGCAATTTTTAATTCGGCTTGCACCACATTATCTCGGTTGGGTGAACTGCTGTCTAC
TGTTATAAGAATGGTCTAGTTGAAGGTGCTAAACTTTATAGTGAGTTGGCACCTCATAGTCATAAATGTAGATG
GTAAATGCTGTGTCTTACCTGAAATTATCTCGCGCGGCTTGCATCCGTACTATCCGTACAAAGGCTATGACCTACTG
TCGCGTTGGCCAGTGTGTGTCCAATCTGCAGAAGGTGTGTTTTGGCGCCGATAGATCTTGTCTATAATCAGAATCT
GGTTCTGACTTGTTGTGGCACAGGGCTCTTACATTGTTGATGAACGTTATTAGTGTTTTTCCAAGACAGTACCAG
TAACTGTGTGTGTCGTCAATACTTTTAAATTGCATTATATGCTTTGCTGCTGTTGCCTGTGTTCTTATTTACAAA
GTTAAGCGCATGTCGGTGATATGGCCATTGCCAGTGTGGCTATGCAACTTGTACTTTTTGTGCACTAAGGTGTTAGATATGT
ATGTAACACAGAACACACTTGGGGATTTTGATCTCATATATAGCTTAAGGTTCAACACAACTTTTGAGGGTGACAAGTTCGTAGGCTCT
GGATTTGGCATTTGGCCATTTGGACCTTTTACCTTTTAAGCTTAACACAACTTTTGAGGGTGACAAGTTCGTAGGCTCT
CATTTTGAGTTTATGCCTAACCTTTTTAAGCTTAATGCATGCCTTGATATGCAATGCCTATGAGAGACTTGCCAACTTTCTCAACTGAA
TTTGAAAATGCTCAGCAGGTACATTGTGCTTGACAATAAGTACAAGTATTATTCAGCAGACTGCTTCAGAGGCTGATTACAGGCTTGC
AACTGGCTCAGTATGCTAGCAGTACTTACAATAAGTACAAGTATTATTCAGCAGACTGCTTCAGAGGCTGATTACAGGCTTGC
TTGTTTGCCCATTTGGCCAAGGCTATGATGGATTATGCTTCTAATCACAAACGACACGTTATACACACCACTGTG
AGTTACAATTCAACTCTACAGGCTGCTGGTAAGATGGCACAACCATCGGTGTTGTGAGAAGTGCATAGTTCGTG
TTTGCTATGTAATACTACTAGATTATGACTATGCCCTTTCTGTTTACGCCTCCACAACTTCTCCATTTCATCGGTAATGTT
TACTACTAGCACTATAGATTATGACTATGCCCTTTCTGTTTACGCCTCCACAACTTCTCCATTTCATCGGTAATGTT
TCCTAGGTTGTGTGGGTAACCATGCGAGTTGCTTGTGCAGATAAAGGTTAATCAAAACAATGTCCACACGCTA
CGGCCGTTAACATGCGCTCTAATTACACCTATTAGAGGCTCGTTCATTAATGGCCGCTTGTGTTCACCTGTTATATATT
AACAATGGTACCGTTGAGTTTGCTATTTACACCAGCTTGAACTTGGTTCAGGCGTCATGTGGTAGGGACTTAGATG

Fig. 2E

GTGTTATGTATGGTGGTTATGAGGACCAACCTACTTTGCAAGTTGAAGGCGCTAGTAGTCTGTTACAGAGAATGTGTT
GGCATTTCTTTATGCAGCCACTCATTAATGGTTCTACCTGGTGGCTTAGTTCTTCTAGGATTGCTGTAGACAGGTTAAT
GAGTGGGCTGTTCATAATGGTATGACAACAGTAGTAATACTGATTGCTTTCTATTCTTGCTGTAAGACTTGGTGTTG
ATGTACAACGTTGTTGGCCTCAATCCAGTCTCTGCATAAGAATTTGGTGGAAGCAAATTCTGGCTATACCTCGTT
GACAGATGAGTTACTACAGGTGAAGTTATACGTCAAATGTATGGCGTTAATCTTCAGAGTGGTTATGTTCACGCGC
TGTAGAAATGTCTGGTTGGTCTTTCTGACTTCTTTCTGACGTGTTGTTCATTGCATTGCTGTCCTCACTTTGATGTCACTCAAGCATAA
GACATTGTTTTCCAGTCTTTTCTAATACCTGCTCTGATTGTTACATCTTGCATTAATTTGGCATTTGATGTTGAAGTC
TACAACTATTTGGCAGAGCATTTGATTACCATTGTTCTCTCATGGGTTTAATGCACAAGGTCTTGTTAACATCTTG
TCTGCTTGTTGTTACCATTTTACACGGCACATACACATGGCGCTTTTTAACACACCTGTGTGCTATGACACTATTTGCTAGT
GGTAGCTTGCTGACTGCGCATATAACTATTTTACGTCAGTGACATTCTAGTGTGCTATGACACTATTTGCTAGT
GTGACTGGCAACTGGTTCGTTGGTGCTGTTGTTGTTATAAAGCTGCTGTTATATGGCCTTGAGATTTCCTACTTTGTGG
CTATTTTGGTGATATTAAGAGTGTTATGTTCTGTAACCTTGTGTTGGGTTATTTTACCTGTTGCTTCTACGGTATTCT
CTACTGGGTCAACAGGTTTTTAAGGTTAGTGTAGGTGTCTATGACTATACTGTTAGTGCTGTGAGTTTAAGTATATG
GTTGCTAACGGCCTACGTGCACCAACTGGAACACTTGATTCACTACTTCTCTGTCCAATTGATTGTATTGGTGGTG
AGCGGAATATTAAGATTTCTTCCGTTCAGTCTAAACTGACTGATATTAAGTGTAGTAACGTTGTGCTTTTAGGCTGTCT
CTCTAGCATGAATGTCTCAGCAAATTCAACAGAATGGGCTATGTGTTGACTGCATAACAAGATCAACTTGTAAT
GACCCAGAAAAGCGCAGGAAATGCTACTTGCTTTGTGGCATTTAGTAGTGTGCTATATGTCCGTTGCCTTCTTATGT
ACTTATTGGAATCCTATTTTAATGACAATAGTATGTGACAACAGTATGAAAGATGCTGTTAATAATGGTTCTCCAACTCAGTTGGTTAAGCAATTGCGC
CATTTATGAAAATGCACGCCAACAGTAGGCGAATTTGACCGTGAGGCTTCTACTCAGCGTAAGCTTGATAGAATGGCGAACAGG
CTGCAGCACAGATGTACAAAGAGGCACAGAGCAGTAATAGGAAGTCCAAAGTTGTAAGTGCTATGCATTCACTGCTTTT
TGGTATGTTGAGACGTTTGGACATGTCTCTGTAGACATTGTTACTTGTACTTCTGATATGCTTATATCGTATCCAGCGTGAGG
GTCATACCGGCAGTCAGTGCTACTAAGCTTAACATTGTTACTTCTGATATGCTTATATCGTATCCAGCGTGAGG
GATGTGTCCACTACGCTGGTACCATTTGGAATATAATTGATATCAAGGACAATGATGGCAAGGTGGTACACGTTAAGGA
GGTAACCGCACAGAATGCTGAGTCCTGTCATGCCCCTGTCATGGCCCTGGGTCCTGGGGTGTGAGGTATTGTCAGCTCCAGAATAAT
GAAATTATTCCTGGTAAGCTGAAGCAGCGCTCCATTAAGGCAGCAGAAGGAGGCATAGTAGTTGGAGAAGGTAAGGCACTTT
ACAATAATGAGGGGACGTACTTTTATGCTTTCATCGATGCTTCATGCTTGGACACAAACCGACCTGGTAGTCAAGTGGGAGTT
CGATGGTGTAACACTATTGAGCTAGAACAGGCTATTAACACGTAAGTTCTTGGTGATTCTCCTAAGTTGCACAGATCAAG
TATCTCTACTTGTTCGTAACCTTAACACTGTAACAACTTAACTCTTCATTGTTGACACTTTTGCGCTTGCCTGCTAAGAC
AGGCTGGTAACAACAAGAACAGGCTATTAACTCTTCATTGTTGACACTTTTGCGCTTGCCTGCTAAGAC
CTACATCGATGCTGTCACAAACCAGTAACTGGTTAAGATGTTAAGATGTTGCCAATGGTTCTGGTAATGGA

Fig. 2F

```
CAAGCTGTTACTAATGGTGTGGAGGCTAGTACTAACCAGGATTCATACGGTGGTGCGTCCGTGTCTATATTGTAGAG
CACATGTTGAGCATCCATCTATGGATGGTTTTGCAGACTGAAAGGCAAGTACGTACAGGTTCCACTAGGTACAGTGGA
TCCTATACGTTTGTACTTGAGAATGACGTTGTGGTTGTGGTTGCCTGGCTGCACTGTGACAGA
TCCATTATGCAAAGCACTGATATGGCTTATTTAAACGAGTACGGGCTCTAGTGCAGCTGACTAGAGCCTGTAACGG
TACTGATACAACAACATGTGATCGTCTTTGACATCTACAACAAGGATGTTGCTTGTCTAGGTAAATTCCTCAAGGTG
AACTGTGTTCGCCTGAAGAATTGGATAAGCATGATGATGCATTCTATGTTGTCAAAGATGTACCAAGTCTGCGATGGAAC
ACGAGCAATCCATCTATGCCAGACTTGAAAAGTGTGGAGCCGTAGCCGAACACGATTCTTCACTTGGAAGGATGGTCG
TGCCATCTATGGTAACGTTGTAGAAAGGATCTTACCGAGTATACTATGATGGATTTGTGTTACGCTTTACGTAACTTT
GATGAAAACAATTGCGATGTTCTTAAGAGCATTTAATTAAGGTAGGCGCTTGTGAGGAGTCCTACTTCAATAATAAAG
TCTGGTTTGACCCGTTGAAAATGAAGACATTCATGTGTCTATGCATTGTAGGTGCATTGTCACATTAGATAATCAGGATCTTAAT
TAAATGCGTTAAGTTCTGTGATGCAATGGTTGAACAAGGTATAGTTGGTGTTGTCACATTAGATAATCAGGATCTTAAT
GGTGATTTTATGATTTTGGTGATTTTACTGTAGCATCAAGGAATGGTATACCCATTGCACATATATTGGTGAGGATTT
ATATGACCTGTATGGTTATGGTTGCCTTGCTAGTGACTAATTGCCTTGCTAGTGAGTGTTTGTTAAGAGTACATCAAGTATTTGGTGAGGATT
CAAGTCATATGACCTGCTGGAATATGATTTCACGGAGCATAAGACAGCATAAGTCCTCAACAGCACTCTTCAACAAGTATTCAAGTATTGGGGA
CTGCAATACCACCCTAACTGTGTGTGGACTGCAGTGATGAGCAGTGCATAGTTCACTGTCCAACTTCAATACGTTGTTTT
CCACTACTATACCTATTACGGCATTTGGACCTTTGTCGTCCAAGTTGGATGATGGTGTCCAACTTACACTACAGC
TGGTTATCATTTTAAACAGTTAGGTATAGTTGGAACAATGCATCATCACCAGCCCTTGTGATCAGCGTACTGTTGCTTT
TACTCCAGTTGTAGTGATCCTGCATTGCTTATAGCACCAGACTTGTTAACCAGACTGTTAACTTTAAAGCACTTCTTCATAAGGAGTTTATGACTTCTT
CAGTTGCAGGCTAGGTACAGGTATGACTACAACAGGCTCTGAGCTTACTTACAACCAGACTTGTTAACTTTAAAGCACTTCTTCATAAGGAGTTTATGACTTCTT
ACTTGAGCAAGGTTCTTTTCTGACGTTCTATAATAGACCTACTACTGTTCTGGACATTGCCAGCTCGGTCGTGTATCAATAG
GTAAGGATTTGACTACTATAGGTATAATAGACCTACTACTGTTCTGGACATTGCCAGCTCGGTCGTGTATCAATAG
TGCAACGCTATTTTGATATTACGAAGGTGGTTGTATCACTGTAAAGAGGTGGTTGTTACAACCTTACACAAGAGCGC
AGGTATCCTTGAACAAGTTGGTAAAGCTGGTCTTTACTATGAGTCTTTATGAGTCTATGAGGAACAGGATGAACTTTAT
GCTTATACTAAGGTAACATCCTGCCCACTATGACACAGCTCAACTGAACACAGACTCAAACTATGCTATAAATGGGCAAAGAACGTGCAC
GCACAGTGGGTGGTTCGCTTGATGGTACTACTAAGTTTATCGTGGTTGGGACACATATGCTAAGAACCTTATTGAT
TACTAGGGCGCTTCGGTTGATGTTCTTATGGGGTTGGGACTACCCAAAGTGCGACAGAGCACTGCCAATATGATATGATTT
GGTGTTGAAATCCGTCTTATGGGTTGGGACTACCCAAAGTGCGACAGAGCACTGCCAATATGATATGATTT
CAGCCATGATTTTAGGCTCTAAGCACACACATGCAGTTCCACTGACCGCTTTCAGGTGTGCAATGAATTGGC
TCAAGTCCTTACTGAGGTGTGTTATTCTAATGGAGGTTTTATTGAAGCCAGGTGGTACTACCTCGTGATGCAACC
ACCGCATATGCAAACTCAGTTTTAATATCTTCCAAGCAGTAAGTGCCAATGTTAACAAACTTCTAGTGTTGACAGCA
ATGTCTGTCATAATTAGAAGTTAAGCAACAATTTTCAATGATGATTCTTCTGATGATGGCGTTGTTTGT
```

Fig. 2G

TATAACAATGACTATGCATCACTTGGTTATGTCGCTGATCTTAACGCATTCAAGGCTGTTTGTATTACCAGAACAATG
TCTTCATGAGCGCCTCTAAATGTTGGATCGAGCCTGACATTAATAAGGTCCTCATGAATTTGCTCGCAGCATACTAT
GCAGATTGTCGATAAAGATGGTACTTATTACCTTCCTTACCCTGATCCTTCAAGAATTCTCTCGCAGGTGTGTTGTT
GATGACGTTGTTAAAACTGATGCAGTTGTATTGCTTGAACGTTATGTGTCATTGGCTATAGATGCCTACCGTTATCTA
AGCATGAAAATCCTGAATATAAGAAGGTGTTTATGTGTCTTTGGATTGGGTAAGCATCTGTACAAACTCTTAATGC
TGGTGTGTTAGAGTCTTTTTCTGTCACACTTGGAAGATTCTACTGCTAAATTCTGGGATGAGAGCTTTTATGCCAAC
ATGTATGAGAAATCTGCAGTTTACAATCTGCAGGGCTTTGTTGTTGGCTCTCAAACTGTTTACGTTGTGGTG
ATTGTCTACGGCGTCCTATGCTTGTGTGCTTCAGATTGTGTACTAAGTGTGCTTATGATCATGTAACTAAGTCTACTTACTTAGTTAT
CATCACTCCATATGTCGTGTGCATCCCGTTGCATTCCCGTTGCTCAGATTGGACTTAATGTTTTTGGCTTGTACAAAATTCTG
TGGTGTCATGACCACCAAGCCACGTCTGCATTCGACGCTACATCCGATTGGACTGATGTTTCTGACTACAGGTTGGC
CTACCGGCTCACCCGATGTTGAAGACTTTAATGCATTGCAGCGGAAACTATCAAGGCCAAGGAGGAGCGTTAAGTCATCCTAT
AAATGATGTCAAGGACTCATTGCGTCGTTTGCAGCGGAAACTATCAAGGCCAAGGAGGAGCGTTAAGTCATCCTAT
GCTTGTGCAACACTACATGAGGTTTCACTTGTTATCATATAAAAACTACCGCCACAACAAACTGTTCCTGGCATGGTTTGTCTT
TAATAGAATTCGGTTTCACTTGTTATCATATAAAAACTACCGCCACAACAAACTGTTCCTGGCATGGTTTGTCTT
GGCAGAATATGATAATGTTCAGCGATTGCGCGCACCGACCATTGCTAATCAAGAACGTTATTCCACTATAAGTGCATC
ACCTCACATAATGTTCAGCGCATTGAGTGCCCTATTACCAATTGATTGGTAAGCAGAGATTACAACTAT
CTGCTTTTAACATACCTGAAGCTTATTCTAGCTTAGTGCCCTATTACCAATTGATTGGTAAGCAGAGATTACAACTAT
TCAGGGACCTCCCGGTAGTGGTAAATCTCACTGTTGTTATAGGGCTTCCACTGTTGTACTATCCAGGTGCACGTATAGTGTTT
ACAGTTGTCTCATGCAGCGGTCGATTCACTTGTGTGAAAGCTTCCACTGCTATAGCAATGACAAATGTTCACGCA
TCATACCACAGCGCGCTCGTGTTGAGTGTTATGATGGTTCAAGTCTAATAATACTAGTGCTCAGTACCTTTCTCTAC
TGTCAATGCTTTGCCAGAGTGCAATGCGGACAATTGTGTGGTGGATGAGGTCTCTATGGTCACTAATTATGACTTGTCT
GTCATAAATCAGCGCATCAGCTATAGGCATGTAGTCTATGTTGGTGACCCTCAACAGTCGCCTGCACCACGTGTTATGA
TTCACGTGGTACTTTGGAACCAAAGGACTACAACGTTGTCACTCAACGCATGTGTGCCCTTAGCCTGATGTTTCTT
GCACAAGTGTTATGCTGTCCTGAGATAGTGCGTACTGTGTCTGAGATGGTCTATGAAACCAATTCATTCCTGTG
CACCCAGATAGCAAGCAGTGTTTAAAATCTTTGCAAGGGTAAGTTCAGGTGATAAGGTTCAAGCATTAATCGCA
GGCAATTGGATGTGTGCGTATGTTTTGGCTAAAATCCTAGGTGGTCAAGTTGGTCAAAGGCTGTTTTATTTCCTTATAACAG
CCAGAATTATGTGCAGCCGCATGCTAGGTCTACAAATTCAGACAGTTGACTCATCCCAGGTAGTGATGACTAT
GTCATTTACACACAAACTTCAGATACTGCCCATGCCGTAATGTTAACAGGTTAACAGGTTGCCATCACAAGGCCAAGA
AAGGCATATTACGAGGGTGTGTCTTTTAAAGACTGTAGCAGAGGTGATGATCTTCAAATAGGTGTTAATAGGTGTTAATGACCATTAATATGAGC
GGCTAATGAGGGTTGTGTCTTTTAAAGACTGTAGCAGAGGTGATGATCTTCAAATAGGTGTTAATAGGTGTTAATGACCATTAATATGAGC
ATGTCTTTAGCGGACAATTTTATGGGCTTCCGTTTGATATCAACATACCAACCATCACACTCTCTTTGCACACGGCGACTTTGC

Fig. 2H

CATGCGCAATGTTAGAGGTTGGTTGGGTTTGACGTTGAAGGAGCACATGTTGTTGGCTCTAACGTCGTACAAATGTC
CCATTGCAATTAGGGTTTTCTAACGGTTGTTGTTAACGGTTGCGTTGTCAGACCTGAAGGTTGCGTTGTAACTGAGTCTGGTGACT
ACATTAAACCCGTCAGAGCTCGTGCTCCACCAGGGAACAATTGCACACCTTTGCCTCTACTTAAACGGGCCAACC
ATGGGATGTGGTTCGTAAGCGTATAGTGCAAATGTGTAGTGACTACTTGTCAACCTATCAGACATACTAATTTTGTG
TTGTGGGCTGGTGGTTTGGAGTTGACAACTATGCGTTACTTGTCAAGATTGGACCAAGCAAGAGTTGTGATTGTGGTA
AGGTTGCTACTTGTTACAATAGTGCGCTGCATAGTGACGTACTGTTGTTCAAACATGCCCTTGGTTGTGATTACCTGTACAA
TCCATACTGTATTGATATACAGCAGTGGGATACAAGGATCACTTAGCCTTACCCACCATGAGCATTGTAATGTACAT
AGAAACGAGCATGTGGCTTCTGGTGATGCCATAATGACTCGTGTCTAGCCATACATGATTGCTTTGTCAAGAACGTTG
ACTGGTCCATCACATACCATTTATTGGTATTCAAATGAGGCTGTTATTAATAAGAGCGGCCAATTGCAATCACACTAT
GCGGTCAGTTCTTAAGTTATACAATCCAAAAGCCATATATGATATTGGCAACCCTAAGGGCATTAGATGTGCGTAACG
GATGCTAAGCGGTCGTCTGCTTTGACAAGAATCCTACTAATCTCAAGACATTGGAGTATGACTATATAACACACG
GCCAATTTGATGGTTGTGCTTGTTTGGAATTGACCATATGCAATGTGGACATGTATCCAGAATTCTCTGTCTGTCGGTTTGA
CACTCGCTAGGTCACCACTCAACTTGGAGGGTTGTAATGTGGTTCACTGTATGTTAATCATGCATTCCATACA
CCGGTCTTTTGACAAGCGTGCTTTGCAAGTTGAAGCCAATGCCATTTTCTTCTATGATACTGAGTGTGACAAGT
TACAGGACTCTATAAACTACGTTCCTCTTAGGGCTAGTAATTGCATTACTAAATGTAATGTTGGTGGAGCTGTCTGTAG
TAAGCATTGTGCTATGTACCATAGTGTTATGCTAACACCACCTTTACGTCGGCGGGCTTTACGATTGGGTGCCC
ACTTCGTTGACACCTACATCTGTGGCAGACATTTAGTGGTTCACTGTATGTTCACTGTATGTTCAAGGATCGGCGACAGTCTTAGACAGTTGACAACTGAATGTGACAAGTCTTCAATGTCG
TAAAGAAGGATCTTGTTGGTGCTGAAGGTCAGCTTCCTGTGAGCTTGGTTAATGACAAAGTGCTCGTTAGAGATGG
TACTGTTGATACTCTTGTTTCACAAAGACATCACTACCACTAACGTAGCTTTGAGTTGTATGCCAAGCGTAAG
GTAGGACTCACCCACCATTAGATCCTACTGTAACTTGGGGTGTTGTTGCACATCTAAGTGTGTCATTGGGACTATG
AAGCCGAACGTCCACTTACTACTTTACAAGGATGCTGTAATATACCGACTTGAGGGTGCGTTGCACACTCTT
TGATAACAGCATTGTGGTTCATTAGAGGCGATTCTCTATGACCCAAAATGTCCCAGTTAACACACATGAAGATAAACCTTTTACT
AGCTTACTGGCATAAGTTAACTTATGTTATCTTAAGTGGTCCCAGTTAACACACATGAAGATAAACCTTTTACT
GGTACATTTACACTAGGAAGAACGGCAAGTTCGAGGACTATCCTGATGGCTATTTTACCCAAGGTAGAACAACGCTGA
TTTTAGCCCTCGTAGTGACATGGAAGGACTTCCTAAGTTATGGATATGGGTCGTTTATTAACAAGTACGACTCGAA
GATTACGGCTTTGAGCACGTTGTGTATGGTAGTGTTCTAAAACCACCCTTGGTCGTTACATCTACTAATTTCGCAGG
TGCGTCTGGCCTGTATGGGTGTGCTTAAATAGACGAGTTTGTGTCTAGTAATGATAGCACGTTAAGTCTTGTACTGT
TACATATGCTGATAACCCTAGTAGTAAGATGGTTTGCACGTATATGGATCTCCTTCTGACGATTTTGTCAGCATTCTT
AAATCGTTGGATTTGAGTGTGTATCTAAAGTTCATGAAGTTATGGTCGATGGTGTAAAATGTGGAGGTGATGTGTGT
GTAAGGATCATAAACCTATGTGTTTATCCGCAACTTCAGGCCAGTGAATGGAAATGTGGTTATTCCATGCCTTCTAT
TTACAAGATACAACGTATGTGTTTAGAACCTTGCAATCTCTATAACTAGTGGCTGGTATTAAGTTACCTGATGGCATT
ATGTTTAACGTAGTTAATATACCAGCTTGTCAATATCTTAATAGCACCACAATGTGTGTACCCATCACATGCGCG

Fig. 21

TGCTACATCTTGGTGCTGGCTCCGACAAGGGTGTTGCACCTGGCACGGCTGTCTTACGACGTTGGTTGCCACTGGATGC
CATTATAGTTGACAATGATAGTGTGGATTACGTTAGCGATGCTGATTATAGTTACGGGAGATTGCTCTACCTTATAC
CTGTCAGATAAGTTGACTAGTTATATCTGATATGTATGATGTAAGATTAAAAGTTGTGATGGGAGAACGTGCTA
AGAAGGCTTCTTTCCCTATATTAATGGTGTCATCACTGAAAAGTTGGCACTTGGTGGTACTGTAGCTATTAAGGTGAC
GGAGTTTAGTTGGAATAAGAAGTTGTATGAACTCATTCAGAGGTTGAGTATTGGACAATGTTCTGTACAGTGTTAAC
ACGTCATCGTCAGAGGCATTCTTAATTGGTGTTCACTATTTAGGTGATTTTGCAAGTGGCGCTGTGATTGACGGCAACA
CTATGCATGCCAATTATATCTTCTGGGTAATTCCACAATTATGACTATGTCTTACAATAGTGTACTTGATTTAAGCAA
GTTCAATTGTAAGCATAAGGCTACAGTTGTCATTATTAAAAGATTCATCCATTAGTGATGTTGTTAGTTTGTTG
AAGAATGGTAAGTTGCTAGTGCGTAATAATGACGCCATTTGTGGTTTTCTAATCATTTGGTCAACGTAAACAAATGAA
GTCTTTAACCTACTTCTGGTTGTTCTTACCAGTACTTTCAACACTCAGCCTACCACACAAGATGTCACTAGGTGCCAGTCC
ACTATTAACTTCAGGCGGTTCTTTCAAATTTAATGTGCAGGCACCTGCTGTCGTGTTATCTACCTA
GTATGAACTCCTCTAGCTGGTCTGGTACTGTGGCACAGGTCTGAAACTGCTAGTGGCGTGTAGCTATTTCCTCAGTTACAT
CGATTCTGGTCAGGGCTTGAGATTGGCATTTCACAGGAGCCGTTGATCCTAGTGGTTACCAGCTTTATTACATAAG
GCCACTAATGGTAACCATAATGCTATTGCACGACTGCGCATTCCAGATAATAAACATTGGGCCTACTG
TTAATGATGTTACAACAGGTCGTAACTGCCTATTCAACAAGCCATTCCAGCTTATATGCAGGATGGAAAAATATCGT
TGTCGGCATAACATGGACAATGATCGTGTCACTGTTTTGCTGACAAGATCTATCATTTTATCTTACACCTACTACTGCTA
TCCCGTGTTGCGACAAGATGTTACAATAAAAGAAGTTGTGCTATGCAATATGTTATACACCTACTACTACATGCTA
ATGTTACTAGTGCAGGTGAGGATGGCATTTATATGAACCATGTACAGCTAATGGTTACGCTGCCAATGTGT
TGCCACTGATCTAATGGCCACATACCAGAAGGTTTAGTTTTAATAATTGGTTCTTTGTCCAATGATTCCACTTG
TTGCATGTAAGGTGGTTCCAACCAACGATGGTTGGTCAATTGTCTTTTGGCCATTCTAAGATTTATGACTAGGCC
AATTTTCTACTCAATCAACGATGATGGCGTTGTAATGAGCTGCTGCGCAGCGTGCACCAGAGGCTCTGAGGTT
TAATATTAATGACACCTCTGTCATTCTTGCTGAAGGCTCATTCATACTGCTTTAGGAACAAATCTTTCTTT
GTTTGCAGTAATTCTTCAGATCCTCATCTAGCTACCTTCGCCATATCTCGGGTGCTACCAAGTGCTACCTATTATTGTT
TTCTTAAAGTGGATACTTACAACTCCACTGTTTATAAATTTTGGCTGTTTACCTCCTACTGTCAGGGAAATTGTCAT
CACCAAGTATGGTGATGTTTATGTCAATGGGTTTGATACTGCATCTCGGTTTGTTGGATGCTGTCACATTAATTC
ACTGGTCATGGCACTGACGATGATGTTCTCGGTTTTGGACCATAGCATGACTGACTAATTTGTTGATGCACTCATGAAG
TTCAAGGAACCGGCATTCAGCGTATTCTTATTGTGATGAAACCTTCTGTTAGCCAACTCAAGTGTTCTCAGGTTGCTTTGA
CCTTGACGATGGTTTTACCCTGTTTACTCTAGAAACCTTCTGAGTCATGAACGCCAATTCTTTGTTACTCTGCCA
TCATTAATGATCATTCTTTGTTAACATTACTGTATCTGCTTCCTTTGACACTAGTGGTCATAGTGGTGCCAACCTTATGCAT
CTGACACTACTATCAATGGGTTTAGTCTTTTCGTGTTGACACTAGACAATTTACCATTTACACTGTTTTATAACGTTAC
AAACAGTTATGGTTATGTGCTAAATCACAGGACAGTAATTGCCCTTCACCTTGCAATCTGTAATGATTACCTGTCT
TTTAGCAAATTTTGTGTTCCACCAGCCTTTGGCTAGTGMCTGTAGTGCTAGTCTTTGGTTACCCTGAGTTTGGTA

Fig. 2J

```
GTGGTGTTAAGTTTACGTCCCTTTACTTCAATTCACAAGGGTGAGTTGATTACTGGCACGCCTAAACCACTTGAAGG
TGTCACGGACGTTCTTTTATGACTCTTTATGACTCTGGAGGTGTGTATTACACATGTGTTATTACACATCTGATTCTGGACAGTTGTTAGCCTTTAAGGTGAGGGTATCATT
ACCCTTACAAATTCTAGCTTTTGGCAGCTTTTATCTGTTACGCCATGTCTTTTCAGAGCAGGCTGCATATGTTGATGATAGTGGGTGT
CTAGTGGTGCTGTTTATCTGTTACGCCATGTCTTTTCAGAGCAGGCTGCATATGTTGATGATAGTGGGTGT
TATTTCTAGTTGTCTAGCTCCACTTTAACAGCACTAGGGAGTTGCCTGGTTCTTCTACCATTCTAATGATGGCTCT
AATTGTACAGAGCCTGTGTTGGGTATAGTAAACATAGGTGTTTGTAAATCGGCAGTATTGGCTACGTCCCATCTCAGT
CTGGCCAAGTCAAGATTGCACCCACGGTTACTGGGAATATTAGTATTCCCACCACTTAGTAGTAATCTCGTTGTAAACAA
ATATTTACAGCTTTACAACACTGCAGCAAGTGTTTGATTGTGCCACATATGTTGTAATGTAACTCTCGTTGTAAACAA
TTACTCACCCAGTACACTGCAGCATGTAAGACCATAGAGTCAGCATTACAACTCAGCGCTAGCTTGAGTCTGTTGAAG
TTAACTCTATGCTACTATTTCTGAAGAGGCTCTACAGTTAGTACCATTAGTTCGTTTAATGGTGATGGATATAATTT
TACTAATGTGCTGGGTGTTTCTGTTCTGTATGATCCTGCAAGTGGCAGGTGGTACAAAAAAGGTCTTTATTGAGACCTG
CTTTTAATAAAGTGGTTACTAAGTGCCTTGGTACTGTTGATGAAGACTATAAGCCGTGTTCTAATGGTCGCTCTGTGG
CAGATCTAGTCTGTGCACAGTATTACTCTGGTGTCATGGTACTACCTGGTGTGTTGACGCTGAAAGCTCACATGTA
TAGTGGTCTCTCATCGGTGGTATGGGTGCTAGGAGGTTTTACTTCTGCAGCGGCAATTGCTTTTAGCTATGCTGTTCAA
GCTAGACTCAATTATCTTGCTCTACAGACGATGTCTACAGCGGAACCAGCAATTGCTTGCTGAGTCTTTAACTCTG
CTATTGGTAATATAACTTCAGCTTTGAGAGTGTTAAAGAGCTATTAGTTCAAACTTCCAAGGGTTTGAACACTGTGGC
TCATGCGCTTACTAAGGTTCAAGAGGTTGTAACTCGCAGGGTGCAGCTTTGACTCAACTTACCGTACCAGTGCAACAC
AACTTCCAAGCCATTTCTAGTTCTATTCACAGCACTTAAGCACTTAAGTTCATTACTCTCGACTGGACATTCTTTCAGCCGATGTTCAGGTTGACC
GTCTCATCACCGGCAGATTATCAGCACTTAAGCACTTAAGTCTTTGTTGCTCAAACCCTCACTAAGTATACGAGGTTCAGGCTAG
CAGGAAGTTAGCACAGCAAAAGGTTAAGAGTTAATGAGTGCGTTAAATCGCAATCTCAGCGTTATGGTTTTGTGGTGATGGC
GAGCACATTTCTCTGGTACAGGCAGCAGCCTCAGGGCCTGCTGTTTTTACATACAGTACTTGTACCGAGTGATTTTG
TAGATGTTATTGCCATCGCTGGCTTATGCGTTAAACGATGAAATTGCCTGACTCTACGTGAGCCTGGCTTAGTCTTGTT
TACGCAATGAAACTCAAAATCATACTGCGACGAGTGTGCGACGTATGTTTGAACCTAGAAACCTACC
GTTAGTGATTTGTTCAAATTGAGAGTTGTGGTCACCTATGTCAATTGACTAGAGACCAACTACCAGATGTAATCC
CAGATTACATGCGATGTTAACAAACACTTGATGAGATTTAGCTTCTCTGCCCAATAGAACTGGTTCAGAGTCTCCTTT
AGATGTTTTAATGCCACTTATCTTAAATCTCACTGGTGAAATTGCAGATTTAGAGCAGCGTTCAGATTTCTCCGTAAT
ACTACAGAGGAGCTCAACTGTCCAAAGTCTTTATAATAATCAACAACACACTAGTTGACCTTGAGTGGCTCAACCGAGTTGAGA
CATATATCAAGTGACCGTGTGGTTGTGAAAAGGTCCACGTGCAGTGATGTTTCTTGGACTTTTCAATACACGATTGACACAGTTGT
CTGCATTTCCACGAAGTTGTGATGGCTGTCGGCTGTCAACGTTGTCTGTTCTCAGGTTGTGTAGGGGTGTTAGGGGTGTTAGGTAGGGGTCTG
CAACCTTACGAAGTTTGAAAGTCTGTAACTTGCTTTGTCAAGAGTTGGAGCTCAATGTAGTCAATTGACACAA
GCTTCAAATGTGACGGGTTTCTTCTCCACCAGTGTTTTATCTACTTCTTGCACTGTTTAAGCGTCTTCTTGAGGC
```

Fig. 2K

GCAATTATATTATGTTGGCAGGCGCGGTTTGCTGTCATTGTCTCTTATTGCCCACTTTATATTATTGTGGTGCATTTT
AGATGCAACTATTATTGTTGCACACTATTGGCAGGCTTTGTTAGTCTGCTTTGTTACTCCTGGCGCTATAAAATGCG
CTCTTTATTATTTTAATACTACGACACTTCTTCCTCAATGTAAAGCAGCTTATTATGACGGCAAATCCATTGTGA
TTTAGAAGGTGGTGACCATTACATCACTTTGGCAACTCTTTGTTGCTTTGTTAGTAGCATCGACTTGTATCTAGC
TATACGTGGGCGGCAAGAAGCTGACTTACAGCTGTTGCGAACTGTTGAGCTCTTGAGCTTCTTGATGCAAGAAGCTTTATGTCTTT
TCGCAACATCAAATTGTGGCATTACTATGTTATATGCTGCATTTGACTCAATTGACTCAATCTAGACGAGTATGCTACAATTAGTGAAT
GATAATGGTCTAGTAGTTAATGTTATACTTTGGCTTTTGGTGTACTCTTTCCTGCTTATTATAAGCATTACTTTCGTCC
AATTGGTTAATCTGTGCTTCACTTGTCTGTGGATAAATGTACTTGCCCGGTTGTGTGTCAATAGCATTCGGTTGTGGCGCAGGACACATTCTTGGTGGTCT
TATAAGTCTTACATGCAAATAGACCCCCTACCTAGTCAGTTATTATGACGTATAAACGAATATGTCTAACGGTTCTAT
TCCGTTGATGAGGTGATTCAACACCTTAGAAACTGGAATTCACATGGAATATCATACTGACGATACTACTTGTAGTG
CTTCAGTATGGCATTACAAGTACTCGCGTTCTGTATGGTGTCAAGATGGCTATTCTATGGATACTTTGGCCTCTG
TGTTAGCACTGTCACTTTTGATGCATGGCTAGCTTCAGGTCAATTGGGTCTTTTTTGCTTTCAGCATCCTTATGGC
TTGCATCACTCTTATGCTGTGGATAAATGTACTTGTCAATAGCATTCGGTTGTGGCGCAGGACACATTCTTGGTGGTCT
TCAATCCTGAAACAGACGCGCTTCTCACTACTTCTGTGATGGGCTGACAGGTCTGCATTCCAGTGCTTGGAGCACCAA
CTGGTGTAACGCTAACACTCCTTAGTGGTACATTGCTTGTAGAGGGCTATAAGGTTGCTACTGGCGTACAGGTAAGTCA
ATTACCTAATTTCGTCACAGTGCCAAGGCCACTACAACAATTGTCTACGACGTGTTGGTCGTTCAGTCAATGCTTCA
TCTGCACTGGTTGGGCTTTCTATGTCCGGTCAAACGGGACTACTCAGCTGTGAGTAATCCGAGTTCGGTTCTCA
CAGATAGTGAGAAAGTGCTTCATTTAGTCATTAGTCATTGGTTACTAATGACAACTTTATGCTCTGCTCAGTTTTCAGATGTCGTGGCCGCAAA
CGGGTGCCATTATCCCTCTATGCCCCTCTTAGGTTACTAGTCATTATGGATACTGAAGCAAATTCGCTGGCCATGCGCCGTGGTGA
TACCCACTAATAAGGAAATAAGGACCAGCAAATTGGATACTGGAAATGAGCAAATTCGCTGGCCATGCGCCGTGGTGA
GCGAATTGAACAACCTTCAATTGGCATTTCTACTACCTCGGAACAGGACCTCACGCCGACCTCCGCTATAGGACTCGT
ACTGAGGGTGTTTTCGGTTGCTAAAGAAGGGCAAAGACTGAACCCACTAACCTGGGTGTCAGAAAGGCGTCTGAAA
AGCCAATTATTCCAAATTCTCTCAACAGCTTCCCAGCGTAGTGAGATTGTTGAACCTAACACCACCTCCTACTTCACG
TGCAAATTCACGTAGCAGGAGTCGTGGTAATGCAACTACAGGTCAGATCTCCAGTTCCAGTAACAACAGAGGCAATAACCAG
TCCGCGGTAATTCACAGAATCGTGGAAATAACCAGGGTCGTGGAGCTTCTCAGAACAGAGGAGCAATAATAATAACA
ATAACAAGTCTGTAACAGTCCAAGAACAGAACCAGTCAAATGACCGTGGTGGTGTAACATCACGCGATGATCTGGT
GGCTGCTGTCAAGGATGCCCTTAAATCTTTGGGTATTGGCGAAAGCTTAAGCAACAGCCACTTCGAAGAACCTGACCTCA
CAGGAAAGGTCTGACACGCAGCGCAAATACACCTAAGAAGAACAAATAGCGTAGCAGCTGCTTCGGACCCAGGGAGGCTTCAA
AAGACATCCAGAGATGGAGAGAATTCCAAGGGGGAAATTCCAAGGGGCGAAAATAGCCTCAGCTATGCTCAGATCGCCAGTTAGCACCAAT
AAATTTTGGAGATGCGGAATTTGTCGAAAAGGTGTTGCGCTGCTGTTCAACGATGCATTACATATAATTATAAA
GTTGCAGCATTGCTCTTTGGTGTAATGTGGGCTGTCCGTGAGCTAGCGACTCTTACGAGATTACATATAATTATAAA
TGACTGTGCCAAAGTCTGATCCAAATGTAGAGCTTCTTGTTCACAGGTGGATGCATTTAAAACTGGAATGCAAACC

Fig. 2L

CCAGAGAAAGAAGGAAAAGAAGAACAAGCGTGAAACCACCGCAGCAGCTGAATGAAGAGCCATCTACGATGATGTGGGT
GTGCCATCTGATGTGACTCATGCCAATTTGGAATGGACACAGCTGTTGATGGTGGTGACACGGCCGTTGAAATTATCA
ACGAGATCTTCGACACAGGAAATTAAACAATGTTGACTGGCTTATCCTGGCTATGTCCCAGGTAGTGCCATTACACT
GTTATTACTGAGTGTTTTCTAGCGACTTGGCTGCTGGGCTATGGCTTGCCCTCTAACTAGCGGTCTTGGTCTTGCAC
ACAACCGTAAGCCAGTGGTAATGTCAGTGCAAGAAGGATATATTACCATAGCACTGTCATGAGGGAACGCAGTACCTTT
CATCTAAACCTTTGCACGAGTAATCAAAGATCCGCTTGACGAGCCTATATGGAAGAGCGTGCCAGGTATTTGACTCAAG
GACTGTTAGTAACTGAAGACCTGACGGGTGTTGATATGGA

FIGURE 3

USA.Indiana12.83.2013 (SEQ ID NO:3):

ATGAAGTCTTTAAATTACTTCTGGTTGTTCTTACCAGTACTTTCAACACTCAGCCTAC
CACAAGATGTCACTAGGTGCCAGTCCACTATTAACTTCAGGCGGTTCTTTTCAAAAT
TTAATGTGCAGGCACCTGCTGTCGTTGTGTTGGGTGGTTATCTACCTAGTATGAACTC
CTCTAGCTGGTACTGTGGCACAGGTCTTGAAACTGCTAGTGGCGTGCATGGTATTTT
CCTCAGTTACATCGATGCTGGTCAGGGCTTTGAGATTGGCATTTCACAGGAGCCGTT
TGATCCTAGTGGTTACCAGCTTTATTTACATAAGGCCACTAATGGTAACCATAATGC
TATTGCACGACTGCGCATTTGCCAGTTTCCAGATAATAAAACATTGGGCCCTACTGT
TAATGATGTTACAACAGGTCGTAACTGCCTATTCAACAAAGCCATTCCAGCTTATAT
GCAGGATGGAAAAAATATCGTTGTCGGCATAACATGGGACAATGATCGTGTCACTG
TTTTTGCTGACAAGATCTATCATTTTTATCTTAAAAATGATTGGTCCCGTGTTGCGAC
AAGATGTTACAATAAAAGAAGTTGTGCTATGCAATATGTTTATACACCTACCTACTA
CATGCTTAATGTTACTAGTGCAGGTGAGGATGGCATTTATTATGAACCATGTACAGC
TAATTGCAGTGGTTACGCTGCCAATGTGTTTGCCACTGATTCTAATGGCCACATACC
AGAAGGTTTTAGTTTTAATAATTGGTTTCTTTTGTCCAATGATTCCACTTTGTTGCAT
GGTAAGGTGGTTTCCAACCAACCTTTGTTGGTCAATTGTCTTTTGGCCATTCCTAAGA
TTTATGGACTAGGCCAATTTTTCTCATTCAATCAAACGATGGATGGCGTTTGTAATG
GAGCTGCTGCGCAGCGTGCACCAGAGGCTCTGAGGTTTAATATTAATGACACCTCTG
TCATTCTTGCTGAAGGCTCAATTGTACTTCATACTGCTTTAGGAACAAATCTTTCTTT
TGTTTGCAGTAATTCTTCAGATCCTCATCTAGCTACCTTCGCCATACCTCTGGGTGCT
ACCCAAGTACCTTATTATTGTTTTCTTAAAGTGGATACTTACAACTCCACTGTTTATA
AATTTTTGGCTGTTTTACCTCCT

FIGURE 4

USA.Iowa23.57.2013 (SEQ ID NO:4):

ATGAAGTCTTTAACCTACTTCTGGTTGTTCTTACCAGTACTTTCAACACTCAGCCTAC
CACAAGATGTCACTAGGTGCCAGTCCACTATTAACTTCAGGCGGTTCTTTTCAAAAT
TTAATGTGCAGGCACCTGCTGTCGTTGTGTTGGGTGGTTATCTACCTAGTATGAACTC
CTCTAGCTGGTACTGTGGCACAGGTCTTGAAACTGCTAGTGGCGTGCATGGTATTTT
CCTCAGTTACATCGATTCTGGTCAGGGCTTTGAGATTGGCATTTCACAGGAGCCGTT
TGATCCTAGTGGTTACCAGCTTTATTTACATAAGGCCACTAATGGTAACCATAATGC
TATTGCACGACTGCGCATTTGCCAGTTTCCAGATAATAAAACATTGGGCCCTACTGT
TAATGATGTTACAACAGGTCGTAACTGCCTATTCAACAAAGCCATTCCAGCTTATAT
GCAGGATGGAAAAAATATCGTTGTCGGCATAACATGGGACAATGATCGTGTCACTG
TTTTTGCTGACAAGATCTATCATTTTTATCTTAAAAATGATTGGTCCCGTGTTGCGAC
AAGATGTTACAATAAAAGAAGTTGTGCTATGCAATATGTTTATACACCTACCTACTA
CATGCTTAATGTTACTAGTGCAGGTGAGGATGGCATTTATTATGAACCATGTACAGC
TAATTGCAGTGGTTACGCTGCCAATGTGTTTGCCACTGATTCTAATGGCCACATACC
AGAAGGTTTTAGTTTTAATAATTGGTTTCTTTTGTCCAATGATTCCACTTTGTTGCAT
GGTAAGGTGGTTTCCAACCAACCTTTGTTGGTCAATTGTCTTTTGGCCATTCCTAAGA
TTTATGGACTAGGCCAATTTTTCTCATTCAATCAAACGATGGATGGCGTTTGTAATG
GAGCTGCTGCGCAGCGTGCACCAGAGGCTCTGAGGTTTAATATTAATGACACCTCTG
TCATTCTTGCTGAAGGCTCAATTGTACTTCATACTGCTTTAGGAACAAATCTTTCTTT
TGTTTGCAGTAATTCTTCAGATCCTCATCTAGCTACCTTCGCCATACCTCTGGGTGCT
ACCCAAGTACCTTATTATTGTTTTCTTAAAGTGGATACTTACAACTCCACTGTTTATA
AATTTTTGGCTGTTTTACCTCCT

PORCINE EPIDEMIC DIARRHEA VIRUS VACCINES AND METHODS OF USE THEREOF

RELATED APPLICATION

This application claims priority under 35 U.S.C. 119(e) to provisional U.S. Ser. No. 61/951,439 filed Mar. 11, 2014, which application is incorporated hereby by reference.

SEQUENCE LISTING

The instant application contains a Sequence Listing which has been submitted electronically in ASCII format and is hereby incorporated by reference in its entirety. Said ASCII copy, created on Feb. 24, 2015, is named 09531.389WO1_SL.txt and is 76,617 bytes in size.

BACKGROUND OF THE INVENTION

Porcine epidemic diarrhea virus (PEDV) is a coronavirus that infects the cells lining the small intestine of a pig, causing porcine epidemic diarrhea, a condition of severe diarrhea and dehydration. It generally causes illness in older hogs, causing weight loss, but is a severe disease in newborn piglets, usually lethal within days of contracting the virus. PEDV was first discovered in Europe, but has become increasingly problematic in Asian countries, such as Korea, China, Japan, the Philippines, and Thailand. It has also spread to North America in 2013, and. (Stevenson, et al., *Journal of Veterinary Diagnostic Investigation*, 25(5) 649-654, 2013). PEDV has a substantial economic burden given that it is highly infectious, resulting in significant morbidity and mortality in piglets and is associated with increased vaccination and disinfection costs (Song, et al., *Virus Genes*, 44 (2): 167-175, 2012).

No known vaccine exists to prevent PEDV infection. Thus, there remains a significant, continuing need for an effective means to prevent or ameliorate PEDV infections.

SUMMARY OF THE INVENTION

The present invention provides a vaccine, and methods of vaccination, effective to immunize a susceptible pig against Porcine Epidemic Diarrhea Virus (PEDV). In certain embodiments, the vaccine contains an immunogenic amount of PEDV in combination with a physiologically-acceptable, non-toxic vehicle. In certain embodiments, the vaccine contains an immunogenic amount of a PEDV S1 protein (also called a "Spike" protein), or a variant thereof, in combination with a physiologically-acceptable, non-toxic vehicle.

In certain embodiments, the present invention provides a composition comprising a first immunogenic composition comprising Porcine epidemic diarrhea virus (PEDV) and a pharmaceutically-acceptable, non-toxic vehicle, wherein the PEDV has at least 90% identity (i.e., 90%, 91%, 92%, 93%, or 94%, or 95%, 96%, 97%, 98%, 99%, 99.1%, 99.2%, 99.3%, 99.4%, 99.5%, 99.6%, 99.7%, 99.8%, 99.9% or 100%) to SEQ ID NO:1 or SEQ ID NO:2. In certain embodiments, the PEDV has at least 99%, 99.9% or 99.99% identity to SEQ ID NO:1 or SEQ ID NO:2. In certain embodiments, the PEDV consists of SEQ ID NO:1 or SEQ ID NO:2.

In certain embodiments, the present invention provides a composition comprising a first immunogenic composition comprising Porcine Epidemic Diarrhea Virus (PEDV) S1 protein and a pharmaceutically-acceptable, non-toxic vehicle, wherein the PEDV S1 protein has at least 90% identity (i.e., 90%, 91%, 92%, 93%, or 94%, or 95%, 96%, 97%, 98%, 99%, 99.1%, 99.2%, 99.3%, 99.4%, 99.5%, 99.6%, 99.7%, 99.8%, 99.9% or 100%) to a protein encoded by SEQ ID NO:3 or SEQ ID NO:4. In certain embodiments, the PEDV has at least 99%, 99.9% or 99.99% identity to a protein encoded by SEQ ID NO:3 or SEQ ID NO:4. In certain embodiments, the PEDV S1 protein consists of a protein encoded by SEQ ID NO:3 or SEQ ID NO:4.

In certain embodiments, the composition further comprises an effective amount of an immunological adjuvant.

In certain embodiments, the composition comprises PEDV or PEDVS1 protein conjugated or linked to a non-PEDV S1 peptide.

In certain embodiments, the composition comprises PEDV or PEDVS1 protein conjugated or linked to a polysaccharide.

In certain embodiments, the composition further comprises a second immunogenic composition.

In certain embodiments, the present invention provides a method of protecting a susceptible pig against Porcine Epidemic Diarrhea Virus (PEDV) infection comprising administering to the pig an effective amount of a composition described above. In certain embodiments, the composition is administered by intramuscular, intradermal, subcutaneous delivery, or via a mucosal surface. In certain embodiments, the composition is administered by oral ingestion. In certain embodiments, the composition is administered intranasally.

In certain embodiments, the present invention provides a composition comprising an expression cassette comprising a promoter and a sequence encoding Porcine Epidemic Diarrhea Virus (PEDV) S1 protein, wherein the PEDV S1 protein has at least 90% identity (i.e., 90%, 91%, 92%, 93%, or 94%, or 95%, 96%, 97%, 98%, 99%, 99.1%, 99.2%, 99.3%, 99.4%, 99.5%, 99.6%, 99.7%, 99.8%, 99.9% or 100%) to a protein encoded by SEQ ID NO:3 or SEQ ID NO:4. In certain embodiments, the PEDV has at least 99%, 99.9% or 99.99% identity to a protein encoded by SEQ ID NO:3 or SEQ ID NO:4. In certain embodiments, the PEDV S1 protein consists of a protein encoded by SEQ ID NO:3 or SEQ ID NO:4.

BRIEF DESCRIPTION OF THE FIGURES

Figure 1B:
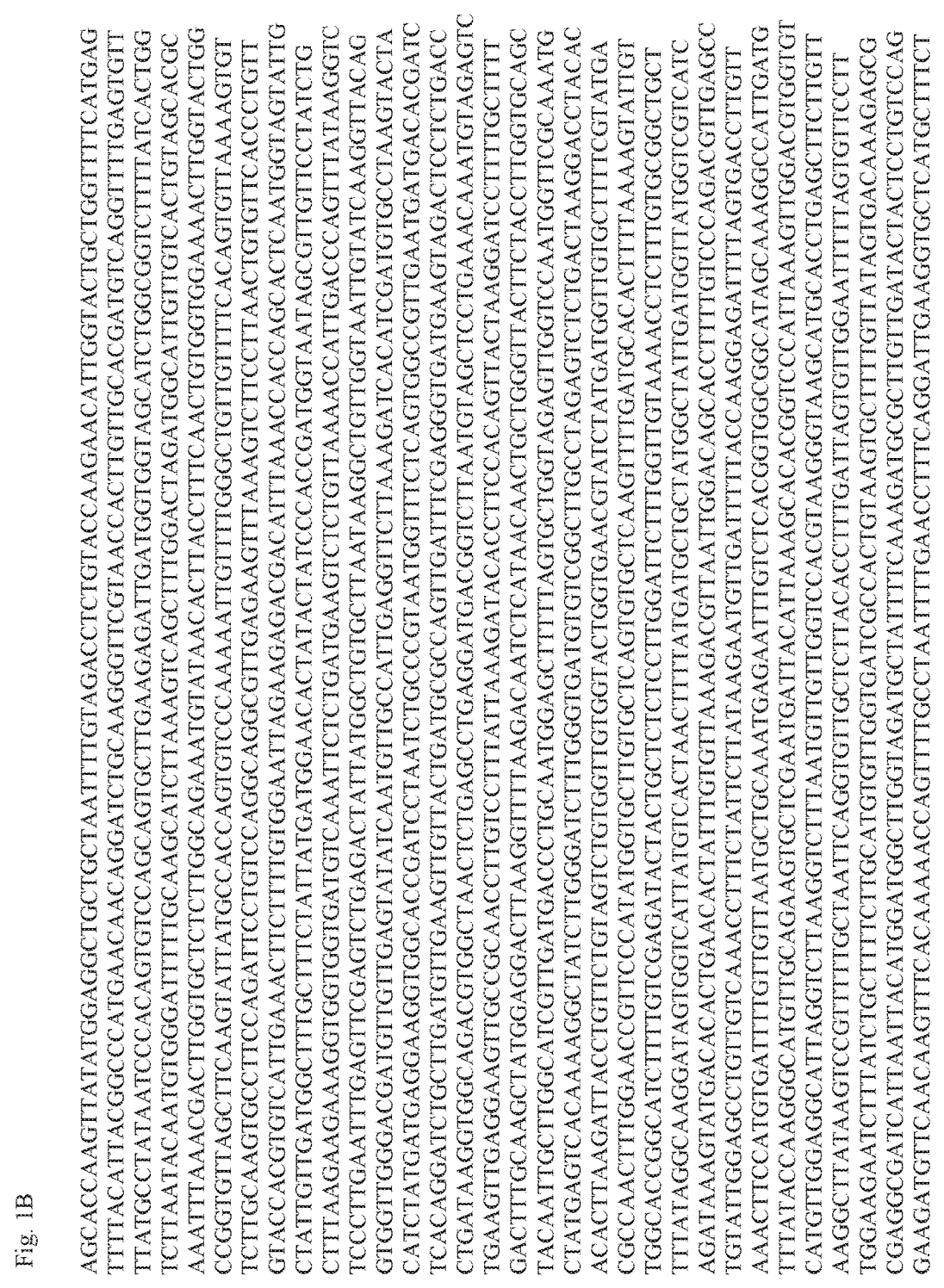

FIGS. 1A-1L together provide the sequence of USA/Indiana12.83/2013 (SEQ ID NO:1).

FIGS. 2A-2L together provides the sequence of USA/Iowa23.57/2013 (SEQ ID NO:2).

FIG. 3 provides USA.Indiana12.83.2013 (SEQ ID NO:3).

FIG. 4 provides USA.Iowa23.57.2013 (SEQ ID NO:4).

DETAILED DESCRIPTION OF THE INVENTION

Nucleic Acids

The present invention provides nucleic acids that encode portions or all of PEDV or PEDV S1 protein. The term "nucleic acid" refers to deoxyribonucleic acid (DNA) or ribonucleic acid (RNA) and polymers thereof in either single- or double-stranded form, composed of monomers (nucleotides) containing a sugar, phosphate and a base that is either a purine or pyrimidine. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues. A "nucleic acid fragment" is a portion of a given nucleic acid molecule.

The terms "polynucleotide", "nucleic acid" and "nucleic acid fragment" are used interchangeably herein. These terms encompass nucleotides connected by phosphodiester linkages. A "polynucleotide" may be a ribonucleic acid (RNA) or deoxyribonucleic acid (DNA) polymer that is single- or double-stranded, that optionally contains synthetic, non-natural or altered nucleotide bases. A polynucleotide in the form of a polymer of DNA may comprise one or more segments of cDNA, genomic DNA, synthetic DNA, or mixtures thereof. Nucleotide bases are indicated herein by a single letter code: adenine (A), guanine (G), thymine (T), cytosine (C), inosine (I) and uracil (U). Unless specifically limited, the term encompasses nucleic acids containing known analogs of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues.

A "nucleotide sequence" is a polymer of DNA or RNA that can be single-stranded or double-stranded, optionally containing synthetic, non-natural or altered nucleotide bases capable of incorporation into DNA or RNA polymers. The terms "nucleic acid," "nucleic acid molecule," "nucleic acid fragment," "nucleic acid sequence or segment," or "polynucleotide" are used interchangeably and may also be used interchangeably with gene, cDNA, DNA and RNA encoded by a gene.

The invention encompasses isolated or substantially purified nucleic acid compositions. In the context of the present invention, an "isolated" or "purified" DNA molecule or RNA molecule is a DNA molecule or RNA molecule that exists apart from its native environment and is therefore not a product of nature. An isolated DNA molecule or RNA molecule may exist in a purified form or may exist in a non-native environment such as, for example, a transgenic host cell. For example, an "isolated" or "purified" nucleic acid molecule or biologically active portion thereof, is substantially free of other cellular material, or culture medium when produced by recombinant techniques, or substantially free of chemical precursors or other chemicals when chemically synthesized. In one embodiment, an "isolated" nucleic acid is free of sequences that naturally flank the nucleic acid (i.e., sequences located at the 5' and 3' ends of the nucleic acid) in the genomic DNA of the organism from which the nucleic acid is derived. Fragments and variants of the disclosed nucleotide sequences are also encompassed by the present invention. By "fragment" or "portion" is meant a full length or less than full length of the nucleotide sequence.

"Naturally occurring," "native," or "wild-type" is used to describe an object that can be found in nature as distinct from being artificially produced. For example, a protein or nucleotide sequence present in an organism (including a virus), which can be isolated from a source in nature and that has not been intentionally modified by a person in the laboratory, is naturally occurring.

"Genome" refers to the complete genetic material of an organism.

"Identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48: 1073 (1988). Preferred methods to determine identity are designed to give the largest match between the sequences tested. Methods to determine identity and similarity are codified in publicly available computer programs. Preferred computer program methods to determine identity and similarity between two sequences include, but are not limited to, the GCG program package (Devereux, J., et al. 1984), BLASTP, BLASTN, and FASTA (Altschul, S. F., et al., 1990. The BLASTX program is publicly available from NCBI and other sources (BLAST Manual, Altschul, S., et al., NCBI NLM NIH Bethesda, Md. 20894; Altschul, S., et al., 1990). The well-known Smith Waterman algorithm may also be used to determine identity.

Nucleic acid molecules encoding amino acid sequence variants of a PEDV S1 protein are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the PEDV S1 protein.

Promoters

"Promoter" refers to a nucleotide sequence, usually upstream (5') to its coding sequence, that controls the expression of the coding sequence by providing the recognition for RNA polymerase and other factors required for proper transcription. "Promoter" includes a minimal promoter that is a short DNA sequence comprised of a TATA-box and other sequences that serve to specify the site of transcription initiation, to which regulatory elements are added for control of expression. "Promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. Accordingly, an "enhancer" is a DNA sequence that can stimulate promoter activity and may be an innate element of the promoter or a heterologous element inserted to enhance the level or tissue specificity of a promoter. It is capable of operating in both orientations (normal or flipped), and is capable of functioning even when moved either upstream or downstream from the promoter. Both enhancers and other upstream promoter elements bind sequence-specific DNA-binding proteins that mediate their effects. Promoters may be derived in their entirety from a native gene, or be composed of different elements derived from different promoters found in nature, or even be comprised of synthetic DNA segments. A promoter may also contain DNA sequences that are involved in the binding of protein factors that control the effectiveness of transcription initiation in response to physiological or developmental conditions. A general discussion of promoters is provided in U.S. Pat. No. 7,501,129, which is incorporated by reference herein.

The invention encompasses isolated or substantially purified nucleic acid compositions. In the context of the present invention, an "isolated" or "purified" DNA molecule or RNA molecule is a DNA molecule or RNA molecule that exists apart from its native environment and is therefore not a product of nature. An isolated DNA molecule or RNA molecule may exist in a purified form or may exist in a non-native environment such as, for example, a transgenic host cell. For example, an "isolated" or "purified" nucleic acid molecule or biologically active portion thereof, is substantially free of other cellular material, or culture medium when produced by recombinant techniques, or substantially free of chemical precursors or other chemicals when chemically synthesized. In one embodiment, an "isolated" nucleic acid is free of sequences that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. Fragments and variants of the disclosed nucleotide sequences are also encompassed by the present invention. By "fragment" or "portion" is meant a full length or less than full length of the nucleotide sequence.

"Naturally occurring," "native," or "wild-type" is used to describe an object that can be found in nature as distinct from being artificially produced. For example, a protein or nucleotide sequence present in an organism (including a virus), which can be isolated from a source in nature and that has not been intentionally modified by a person in the laboratory, is naturally occurring.

In certain embodiments, the present invention provides vectors and expression cassettes containing the promoters described above. A "vector" is defined to include, inter alia, any viral vector, as well as any plasmid, cosmid, phage or binary vector in double or single stranded linear or circular form that may or may not be self-transmissible or mobilizable, and that can transform prokaryotic or eukaryotic host either by integration into the cellular genome or exist extrachromosomally (e.g., autonomous replicating plasmid with an origin of replication).

Nucleic acids encoding therapeutic compositions can be engineered into a vector using standard ligation techniques, such as those described in Sambrook and Russell, Molecular Cloning: A Laboratory Manual, Cold Spring Harbor Laboratory Press Cold Spring Harbor, N.Y. (2001). For example, ligations can be accomplished in 20 mM Tris-Cl pH 7.5, 10 mM MgCl2, 10 mM DTT, 33 μg/ml BSA, 10 mM-50 mM NaCl, and either 40 μM ATP, 0.01-0.02 (Weiss) units T4 DNA ligase at 0° C. (for "sticky end" ligation) or 1 mM ATP, 0.3-0.6 (Weiss) units T4 DNA ligase at 14° C. (for "blunt end" ligation). Intermolecular "sticky end" ligations are usually performed at 30-100 μg/ml total DNA concentrations (5-100 nM total end concentration).

In certain embodiments, the present invention provides a vector containing an expression cassette comprising a promoter operably linked to a target sequence (e.g., PEDV S1 protein) for production of vaccine. "Expression cassette" as used herein means a nucleic acid sequence capable of directing expression of a particular nucleotide sequence in an appropriate host cell, which includes a promoter operably linked to the nucleotide sequence of interest that may be operably linked to termination signals. The coding region usually codes for a functional RNA of interest, for example an RNAi molecule. The expression cassette including the nucleotide sequence of interest may be chimeric.

"Operably-linked" refers to the association of nucleic acid or amino acid sequences on single molecular fragment so that the function of one of the sequences is affected by another. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation. Nucleic acid is "operably linked" when it is placed into a functional relationship with another nucleic acid sequence. Generally, "operably linked" means that the DNA sequences being linked are contiguous. However, enhancers do not have to be contiguous. Linking is accomplished by ligation at convenient restriction sites. If such sites do not exist, the synthetic oligonucleotide adaptors or linkers are used in accordance with conventional practice. Additionally, multiple copies of the nucleic acid encoding enzymes may be linked together in the expression vector. Such multiple nucleic acids may be separated by linkers.

"Expression" refers to the transcription and/or translation of an endogenous gene or a transgene in cells. For example, in the case of antisense constructs, expression may refer to the transcription of the antisense DNA only. In addition, expression refers to the transcription and stable accumulation of sense (mRNA) or functional RNA. Expression may also refer to the production of protein.

"Expression cassette" as used herein means a DNA sequence capable of directing expression of a particular nucleotide sequence in an appropriate host cell, comprising a promoter operably linked to the nucleotide sequence of interest that is operably linked to termination signals. It also typically comprises sequences required for proper translation of the nucleotide sequence. The coding region usually codes for a protein of interest but may also code for a functional RNA of interest, for example antisense RNA or a nontranslated RNA, in the sense or antisense direction. The expression cassette comprising the nucleotide sequence of interest may be chimeric, meaning that at least one of its components is heterologous with respect to at least one of its other components. The expression cassette may also be one that is naturally occurring but has been obtained in a recombinant form useful for heterologous expression. Such expression cassettes will comprise the transcriptional initiation region linked to a nucleotide sequence of interest. Such an expression cassette may be provided with a plurality of restriction sites for insertion of the gene of interest to be under the transcriptional regulation of the regulatory regions. The expression cassette may additionally contain selectable marker genes.

The present disclosure also provides a mammalian cell containing a vector described herein.

Proteins

The PEDV S1 protein can be conjugated or linked to another peptide or to a polysaccharide. For example, immunogenic proteins well-known in the art, also known as "carriers," may be employed. Useful immunogenic proteins include keyhole limpet hemocyanin (KLH), bovine serum albumin (BSA), ovalbumin, human serum albumin, human gamma globulin, chicken immunoglobulin G and bovine gamma globulin. Useful immunogenic polysaccharides include polysaccharides from other pathogens, such as those that are effective as vaccines. The immunogenic polysaccharides or proteins of other pathogens can be conjugated to, linked to, or mixed with PEDV S1 protein.

The terms "protein," "peptide" and "polypeptide" are used interchangeably herein.

The term "amino acid" includes the residues of the natural amino acids (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in Dextrorotary or Levorotary stereoisomeric forms, as well as unnatural amino acids (e.g., phosphoserine, phosphothreonine, phosphotyrosine, hydroxyproline, and gamma-carboxyglutamate; hippuric acid, octahydroindole-2-carboxylic acid, statine, 1,2,3,4,-tetrahydroisoquinoline-3-carboxylic acid, penicillamine, ornithine, citruline, alpha-methyl-alanine, para-benzoylphenylalanine, phenylglycine, propargylglycine, sarcosine, and tert-butylglycine). The term also comprises natural and unnatural amino acids (Dextrorotary and Levorotary stereoisomers) bearing a conventional amino protecting group (e.g. acetyl or benzyloxycarbonyl), as well as natural and unnatural amino acids protected at the carboxy terminus (e.g., as a $(C_1-C_6)$alkyl, phenyl or benzyl ester or amide; or as an α-methylbenzyl amide). Other suitable amino and carboxy protecting groups are known to those skilled in the art (See for example, Greene, T. W.; Wutz, P. G. M., Protecting Groups In Organic Synthesis; second edition, 1991, New York, John Wiley & sons, Inc, and documents cited therein). An amino acid can be linked to the remainder of a compound through the carboxy terminus, the amino terminus, or through any other convenient point of attachment, such as, for example, through the sulfur of cysteine.

The invention encompasses isolated or substantially purified protein compositions. In the context of the present invention, an "isolated" or "purified" polypeptide is a polypeptide that exists apart from its native environment and is therefore not a product of nature. A polypeptide may exist in a purified form or may exist in a non-native environment such as, for example, a transgenic host cell. For example, an "isolated" or "purified" protein, or biologically active portion thereof, is substantially free of other cellular material, or culture medium when produced by recombinant techniques, or substantially free of chemical precursors or other chemicals when chemically synthesized. A protein that is substantially free of cellular material includes preparations of protein or polypeptide having less than about 30%, 20%, 10%, 5%, (by dry weight) of contaminating protein. When the protein of the invention, or biologically active portion thereof, is recombinantly produced, preferably culture medium represents less than about 30%, 20%, 10%, or 5% (by dry weight) of chemical precursors or non-protein-of-interest chemicals. Fragments and variants of the disclosed proteins or partial-length proteins encoded thereby are also encompassed by the present invention. By "fragment" or "portion" is meant a full length or less than full length of the amino acid sequence of, a polypeptide or protein.

A "variant" of a molecule is a sequence that is substantially similar to the sequence of the native molecule.

"Isolated" means altered or removed from the natural state. For example, a nucleic acid or a peptide naturally present in a living animal is not "isolated." but the same nucleic acid or peptide partially or completely separated from the coexisting materials of its natural state is "isolated." An isolated nucleic acid or protein can exist in substantially purified form, or can exist in a non-native environment such as, for example, a host cell. Unless it is particularly specified otherwise herein, the proteins, virion complexes, antibodies and other biological molecules forming the subject matter of the present invention are isolated, or can be isolated.

The term "substantial identity" in the context of a peptide indicates that a peptide comprises a sequence with at least 70%, 71%, 72%, 73%, 74%, 75%, 76%, 77%, 78%, or 79%, 80%, 81%, 82%, 83%, 84%, 85%, 86%, 87%, 88%, or 89%, at least 90%, 91%, 92%, 93%, or 94%, or 95%, 96%, 97%, 98% or 99%, sequence identity to a reference sequence over a specified comparison window. Optimal alignment is conducted using the homology alignment algorithm of Needleman and Wunsch, J. Mol. Biol. 48:443 (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution.

Adjuvants

The term "adjuvant" as used herein refers to non-specific stimulators of the immune response or substances that allow generation of a depot in the host, which when combined with the vaccine and pharmaceutical composition, respectively, of the present invention may provide for an even more enhanced immune response. Vaccines commonly contain two components: antigen (e.g., PEDV S1 protein or PEDV) and adjuvant. The antigen is the molecular structure encoded by the pathogen or tumor against which the immune response is directed. To activate an antigen-specific immune response, the antigen must be presented in the appropriate immunostimulatory microenvironment. In certain embodiments, adjuvants establish such microenvironments by stimulating the production of immune-activating molecules such as proinflammatory cytokines. Vaccine efficacy depends on the types of antigen and adjuvant, and how they are administered. Striking the right balance among these components is important to eliciting the desired immunological result.

Immunogenic compositions as described herein also comprise, in certain embodiments, one or more adjuvants. An adjuvant is a substance that enhances the immune response when administered together with an immunogen or antigen. A number of cytokines or lymphokines have been shown to have immune modulating activity, and thus are useful as adjuvants, including, but not limited to, the interleukins 1-α, 1-β, 2, 4, 5, 6, 7, 8 and 10, 12 (see, e.g., U.S. Pat. No. 5,723,127), 13, 14, 15, 16, 17 and 18 (and its mutant forms); the interferons-α,β and γ; granulocyte-macrophage colony stimulating factor (GM-CSF) (see, e.g., U.S. Pat. No. 5,078, 996 and ATCC Accession Number 39900); macrophage colony stimulating factor (M-CSF); granulocyte colony stimulating factor (G-CSF); and the tumor necrosis factors α and β. Still other adjuvants that are useful with the immunogenic compositions described herein include chemokines, including without limitation, MCP-1, MIP-1α, MIP-1β, and RANTES; adhesion molecules, such as a selectin, e.g., L-selectin, P-selectin and E-selectin; mucin-like molecules, e.g., CD34, GlyCAM-1 and MadCAM-1; a member of the integrin family such as LFA-1, VLA-1, Mac-1 and p150.95; a member of the immunoglobulin superfamily such as PECAM, ICAMs, e.g., ICAM-1, ICAM-2 and ICAM-3, CD2 and LFA-3; co-stimulatory molecules such as CD40 and CD40L; growth factors including vascular growth factor, nerve growth factor, fibroblast growth factor, epidermal growth factor, B7.2, PDGF, BL-1, and vascular endothelial growth factor; receptor molecules including Fas, TNF receptor, Flt, Apo-1, p55, WSL-1, DR3, TRAMP, Apo-3, AIR, LARD, NGRF, DR4, DR5, KILLER, TRAIL-R2, TRICK2, and DR6; and Caspase (ICE).

Still other adjuvants include muramyl peptides, such as N-acetyl-muramyl-L-threonyl-D-isoglutamine (thr-MDP), N-acetyl-normuramyl-L-alanine-2-(1'-2' dipalmitoyl-sn-glycero-3-hydroxyphosphoryloxy)-ethylamine (MTP-PE); oil-in-water emulsions, such as MF59 (U.S. Pat. No. 6,299,884) (containing 5% Squalene, 0.5% Tween 80, and 0.5% Span 85 (optionally containing various amounts of MTP-PE) formulated into submicron particles using a microfluidizer such as Model 110Y microfluidizer (Microfluidics, Newton, Mass.)), and SAF (containing 10% Squalene, 0.4% Tween 80, 5% pluronic-blocked polymer L121, and thr-MDP, either microfluidized into a submicron emulsion or vortexed to generate a larger particle size emulsion); aluminum salts (alum), such as aluminum hydroxide, aluminum phosphate, aluminum sulfate; Amphigen; Avridine; L121/squalene; D-lactide-polylactide/glycoside; pluronic polyols; killed *Bordetella*; saponins, such as Stimulon™ QS-21 (Antigenics, Framingham, Mass.), described in U.S. Pat. No. 5,057,540, ISCOMATRIX (CSL Limited, Parkville, Australia), described in U.S. Pat. No. 5,254,339, and immunostimulating complexes (ISCOMS); *Mycobacterium tuberculosis*; bacterial lipopolysaccharides; synthetic polynucleotides such as oligonucleotides containing a CpG motif (e.g., U.S. Pat. No. 6,207,646); IC-31 (Intercell AG, Vienna, Austria), described in European Patent Nos. 1,296,713 and 1,326,634; a pertussis toxin (PT) or mutant thereof, a cholera toxin or mutant thereof (e.g., U.S. Pat. Nos. 7,285,281, 7,332,174, 7,361,355 and 7,384,640); or an *E. coli* heat-labile toxin (LT) or mutant thereof, particularly LT-K63, LT-R72 (e.g., U.S. Pat. Nos. 6,149,919, 7,115,730 and 7,291,588).

Suitable adjuvants used to enhance an immune response further include, without limitation, MPL™ (3-O-deacylated monophosphoryl lipid A, Corixa, Hamilton, Mont.), which is described in U.S. Pat. No. 4,912,094. Also suitable for use as adjuvants are synthetic lipid A analogs or aminoalkyl glucosamine phosphate compounds (AGP), or derivatives or analogs thereof, which are available from Corixa (Hamilton, Mont.), and which are described in U.S. Pat. No. 6,113,918. One such AGP is 2-[(R)-3-Tetradecanoyloxytetradecanoylamino]ethyl 2-Deoxy-4-O-phosphono-3-O—[(R)-3-tetradecanoyoxytetradecanoyl]-2-[(R)-3-tetradecanoyloxytetradecanoyl-amino]-b-D-glucopyranoside, which is also known as 529 (formerly known as RC529). This 529 adjuvant is formulated as an aqueous form (AF) or as a stable emulsion (SE).

Suitable adjuvants include but are not limited to surfactants, e.g., hexadecylamine, octadecylamine, lysolecithin, dimethyldioctadecylammonium bromide, N,N-dioctadecyl-N'—N-bis(2-hydroxyethyl-propane di-amine), methoxyhexadecyl-glycerol, and pluronic polyols; polanions, e.g., pyran, dextran sulfate, poly IC, polyacrylic acid, carbopol; peptides, e.g., muramyl dipeptide, MPL, aimethylglycine, tuftsin, oil emulsions, alum, and mixtures thereof. Other potential adjuvants include the B peptide subunits of *E. coli* heat labile toxin or of the cholera toxin. McGhee, J. R., et al., "On vaccine development," *Sem. Hematol.*, 30:3-15 (1993). Finally, the immunogenic product may be incorporated into liposomes for use in a vaccine formulation, or may be conjugated to proteins such as keyhole limpet hemocyanin (KLH) or human serum albumin (HSA) or other polymers.

Vaccines of the Invention

In certain embodiments, the present invention provides vaccines for use to protect mammals against or to treat a PEDV infection.

As used herein, the term "therapeutic agent" or "therapeutic complex" refers to any agent or material that has a beneficial effect on the mammalian recipient. Thus, "therapeutic agent" embraces both therapeutic and prophylactic molecules having nucleic acid or protein components.

To prepare a vaccine, the PEDV or PEDV S1 protein can be isolated, lyophilized and stabilized. The PEDV or PEDV S1 protein may then be adjusted to an appropriate concentration, optionally combined with a suitable vaccine adjuvant, and packaged for use.

In certain embodiments, the present invention comprises two or more immunogenic polypeptides. In certain embodiments, one or more polypeptides are adjusted to an appropriate concentration and can be formulated with any suitable adjuvant, diluent, pharmaceutically acceptable carrier, or any combination thereof. As used herein the phrase "pharmaceutically acceptable carrier" is intended to include any and all solvents, dispersion media, coatings, antibacterial and antifungal agents, isotonic and absorption delaying agents, excipients and the like, compatible with pharmaceutical administration. The use of such media and agents for pharmaceutically active substances is well known in the art. Physiologically acceptable vehicles may be used as carriers and/or diluents. A pharmaceutically acceptable vehicle is understood to designate a compound or a combination of compounds entering into a pharmaceutical or immunogenic composition which does not cause side effects and which makes it possible, for example, to facilitate the administration of the active compound, to increase its life and/or its efficacy in the body, to increase its solubility in solution or alternatively to enhance its preservation. These pharmaceutically acceptable vehicles are well known and will be adapted by persons skilled in the art according to the nature and the mode of administration of the active compound chosen. These include, but are not limited to, water, Ringer's solution, an appropriate isotonic medium, glycerol, ethanol and other conventional solvents, phosphate buffered saline, and the like.

"Treating" as used herein refers to ameliorating at least one symptom of, curing and/or preventing the development of a given disease or condition.

"Antigen" refers to a molecule capable of being bound by an antibody. An antigen is additionally capable of being recognized by the immune system and/or being capable of inducing a humoral immune response and/or cellular immune response leading to the activation of B- and/or T-lymphocytes. An antigen can have one or more epitopes (B- and/or T-cell epitopes). Antigens as used herein may also be mixtures of several individual antigens. "Antigenic determinant" refers to that portion of an antigen that is specifically recognized by either B- or T-lymphocytes. B-lymphocytes responding to antigenic determinants produce antibodies, whereas T-lymphocytes respond to antigenic determinants by proliferation and establishment of effector functions critical for the mediation of cellular and/or humoral immunity.

An "immune response" refers to a humoral immune response and/or cellular immune response leading to the activation or proliferation of B- and/or T-lymphocytes and/or and antigen presenting cells. In some instances, however, the immune responses may be of low intensity and become detectable only when using at least one substance in accordance with the invention. "Immunogenic" refers to an agent used to stimulate the immune system of a living organism, so that one or more functions of the immune system are increased and directed towards the immunogenic agent. An "immunogenic polypeptide" is a polypeptide that elicits a cellular and/or humoral immune response, whether alone or linked to a carrier. Preferably, antigen presenting cell may be activated.

A substance that "enhances" an immune response refers to a substance in which an immune response is observed that is greater or intensified or deviated in any way with the addition of the substance when compared to the same immune response measured without the addition of the substance. For example, the lytic activity of cytotoxic T cells can be measured, e.g. using a $^{51}$Cr release assay, in samples obtained with and without the use of the substance during immunization. The amount of the substance at which the CTL lytic activity is enhanced as compared to the CTL lytic activity without the substance is said to be an amount sufficient to enhance the immune response of the animal to the antigen. In certain embodiments, the immune response in enhanced by a factor of at least about 2, such as by a factor of about 3 or more. The amount or type of cytokines secreted may also be altered. Alternatively, the amount of antibodies induced or their subclasses may be altered.

The terms "immunize" or "immunization" or related terms refer to conferring the ability to mount a substantial immune response (comprising antibodies and/or cellular immunity such as effector CTL) against a target antigen or epitope. These terms do not require that complete immunity be created, but rather that an immune response be produced which is substantially greater than baseline. For example, a mammal may be considered to be immunized against a target antigen if the cellular and/or humoral immune response to the target antigen occurs following the application of methods of the invention.

The term "immunotherapeutic" refers to a composition for the treatment of diseases, disorders or conditions. More specifically, the term is used to refer to a method of treatment wherein a beneficial immune response is generated by vaccination or by transfer of immune molecules. An "immunologically effective amount" refers to an amount of a composition sufficient to induce an immune response in an individual when introduced into that individual. In the context of active immunization, the term is synonymous with "immunogenically effective amount." The amount of a composition necessary to be immunologically effective varies according many factors including to the composition, the presence of other components in the composition, the antigen, the route of immunization, the individual, the prior immune or physiologic state etc.

The term "epitope" refers to basic element or smallest unit of recognition by an individual antibody or T-cell receptor, and thus the particular domain, region or molecular structure to which said antibody or T-cell receptor binds. An antigen may consist of numerous epitopes while a hapten, typically, may possess few epitopes. As used herein "correspond essentially to" refers to an epitope that will elicit an immunological response at least substantially equivalent to the response generated by the native epitope. An immunological response to a composition or vaccine is the development in the host of a cellular and/or antibody-mediated immune response to the polypeptide or vaccine of interest. Usually, such a response consists of the subject producing antibodies, B cell, helper T cells, suppressor T cells, and/or cytotoxic T cells directed specifically to an antigen or antigens included in the composition or vaccine of interest. Vaccines of the present invention can also include effective amounts of immunological adjuvants, known to enhance an immune response. An "effective amount" refers to an amount necessary or sufficient to realize a desired biologic effect. An effective amount of the composition would be the amount that achieves this selected result, and such an amount could be determined as a matter of routine by a person skilled in the art. For example, an effective amount for treating an immune system deficiency could be that amount necessary to cause activation of the immune system, resulting in the development of an antigen specific immune response upon exposure to antigen. The term is also synonymous with "sufficient amount." The effective amount for any particular application can vary depending on such factors as the disease or condition being treated, the particular composition being administered, the size of the subject, and/or the severity of the disease or condition. One of ordinary skill in the art can empirically determine the effective amount of a particular composition of the present invention without necessitating undue experimentation.

To immunize a subject, the composition is administered parenterally, usually by intramuscular or subcutaneous injection in an appropriate vehicle. Other modes of administration, however, such as oral, intranasal or intradermal delivery, are also acceptable.

Vaccine formulations will contain an effective amount of the active ingredient in a vehicle, the effective amount being readily determined by one skilled in the art. The active ingredient may typically range from about 1% to about 95% (w/w) of the composition, or even higher or lower if appropriate. The quantity to be administered depends upon factors such as the age, weight and physical condition of the animal or the human subject considered for vaccination. The quantity also depends upon the capacity of the animal's immune system to synthesize antibodies, and the degree of protection desired. Effective dosages can be readily established by one of ordinary skill in the art through routine trials establishing dose response curves. The subject is immunized by administration of the biofilm peptide or fragment thereof in one or more doses. Multiple doses may be administered as is required to maintain a state of immunity to the bacterium of interest.

Intranasal formulations may include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

Oral liquid preparations may be in the form of, for example, aqueous or oily suspension, solutions, emulsions, syrups or elixirs, or may be presented dry in tablet form or a product for reconstitution with water or other suitable vehicle before use. Such liquid preparations may contain conventional additives such as suspending agents, emulsifying agents, non-aqueous vehicles (which may include edible oils), or preservative.

To prepare a vaccine, the purified composition can be isolated, lyophilized and stabilized. The composition may then be adjusted to an appropriate concentration, optionally combined with a suitable vaccine adjuvant, and packaged for use.

Formulations and Methods of Administration

In certain embodiments, an effective amount of the virus, vaccine or therapeutic composition is administered to the subject. "Effective amount" or "therapeutically effective amount" are used interchangeably herein, and refer to an amount of a compound, formulation, material, or composition, as described herein effective to achieve a particular biological result. Such results may include, but are not limited to the inhibition of virus infection as determined by any means suitable in the art.

In certain embodiments, an amount of the vaccine is administered in order to immunize to the subject. As used herein, "immunization" or "vaccination" are used interchangeably herein and are intended for prophylactic or therapeutic immunization or vaccination.

In certain embodiments, the vaccine, therapeutic composition or virus is administered via intramuscular, intradermal, or subcutaneous delivery. In certain embodiments, the vaccine, therapeutic composition or virus is administered via a mucosal surface, such as an oral, or intranasal surface. In certain embodiments, the vaccine, therapeutic composition or virus is administered via intrasternal injection, or by using infusion techniques.

In certain embodiments, "pharmaceutically acceptable" refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability. "Pharmaceutically acceptable carrier" refers to a medium that does not interfere with the effectiveness of the biological activity of the active ingredient(s) and is not toxic to the host to which it is administered.

The vaccines and compositions of the invention may be formulated as pharmaceutical compositions and administered to a mammalian host, such as a human patient, in a variety of forms adapted to the chosen route of administration, i.e., orally, intranasally, intradermally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts may be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient that are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions. For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Additional ingredients such as fragrances or antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

To immunize a subject, the PEDV S1 protein or PEDV is administered parenterally, usually by intramuscular or subcutaneous injection in an appropriate vehicle. Other modes of administration, however, such as oral delivery or intranasal delivery, are also acceptable. Vaccine formulations will contain an effective amount of the active ingredient in a vehicle.

Formulations will contain an effective amount of the active ingredient in a vehicle, the effective amount being readily determined by one skilled in the art. "Effective amount" is meant to indicate the quantity of a compound necessary or sufficient to realize a desired biologic effect. The active ingredient may typically range from about 1% to about 95% (w/w) of the composition, or even higher or lower if appropriate. The amount for any particular application can vary depending on such factors as the severity of the condition. The quantity to be administered depends upon factors such as the age, weight and physical condition of the animal considered for vaccination and kind of concurrent treatment, if any. The quantity also depends upon the capacity of the animal's immune system to synthesize antibodies, and the degree of protection desired. Typically, dosages used in vitro may provide useful guidance in the amounts useful for in situ administration of the composition, and animal models may be used to determine effective dosages for treatment of particular disorders. Various considerations are described, e.g., in Gilman et al., eds., Goodman And Gilman's: The Pharmacological Bases of Therapeutics, 8th ed., Pergamon Press, 1990; and Remington's Pharmaceutical Sciences, 17th ed., Mack Publishing Co., Easton, Pa., 1990, each of which is herein incorporated by reference. Additionally, effective dosages can be readily established by one of ordinary skill in the art through routine trials establishing dose response curves. The subject is immunized by administration of the composition thereof in one or more doses. Multiple doses may be administered as is required to maintain a state of immunity to the target. For example, the initial dose may be followed up with a booster dosage after a period of about four weeks to enhance the immunogenic response. Further booster dosages may also be administered. The composition may be administered multiple (e.g., 2, 3, 4 or 5) times at an interval of, e.g., about 1, 2, 3, 4, 5, 6 or 7, 14, or 21 days apart.

Intranasal formulations may include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

Oral liquid preparations may be in the form of, for example, aqueous or oily suspension, solutions, emulsions, syrups or elixirs, or may be presented dry in tablet form or a product for reconstitution with water or other suitable vehicle before use. Such liquid preparations may contain conventional additives such as suspending agents, emulsifying agents, non-aqueous vehicles (which may include edible oils), or preservative.

Thus, the present compositions may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the present compositions may be combined with one or more excipients and used in the form of ingestible tablets, buccal tablets, troches, capsules, elixirs, suspensions, syrups, wafers, and the like. Such preparations should contain at least 0.1% of the present composition. The percentage of the compositions may, of course, be varied and may conveniently be between about 2 to about 60% of the weight of a given unit dosage form. The amount of present composition in such therapeutically useful preparations is such that an effective dosage level will be obtained.

Useful dosages of the compositions of the present invention can be determined by comparing their in vitro activity, and in vivo activity in animal models. The amount of the compositions described herein required for use in treatment will vary with the route of administration and the age and condition of the subject and will be ultimately at the discretion of the attendant veterinarian or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

All publications, patents and patent applications cited herein are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and "or" and similar referents in the context of describing the invention are to be construed to cover both the singular and the plural, unless otherwise indicated herein or clearly contradicted by context. Thus, for example, reference to "a subject polypeptide" includes a plurality of such polypeptides and reference to "the agent" includes reference to one or more agents and equivalents thereof known to those skilled in the art, and so forth.

The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventor for carrying out the invention. Variations of those embodiments may become apparent to those of ordinary skill in the art upon reading the foregoing description. The inventor expects skilled artisans to employ such variations as appropriate, and the inventor intends for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

With respect to ranges of values, the invention encompasses each intervening value between the upper and lower limits of the range to at least a tenth of the lower limit's unit, unless the context clearly indicates otherwise. Further, the invention encompasses any other stated intervening values. Moreover, the invention also encompasses ranges excluding either or both of the upper and lower limits of the range, unless specifically excluded from the stated range.

Further, all numbers expressing quantities of ingredients, reaction conditions, % purity, polypeptide and polynucleotide lengths, and so forth, used in the specification and claims, are modified by the term "about," unless otherwise indicated. Accordingly, the numerical parameters set forth in the specification and claims are approximations that may vary depending upon the desired properties of the present invention. At the very least, and not as an attempt to limit the application of the doctrine of equivalents to the scope of the claims, each numerical parameter should at least be construed in light of the number of reported significant digits, applying ordinary rounding techniques. Nonetheless, the numerical values set forth in the specific examples are reported as precisely as possible. Any numerical value, however, inherently contains certain errors from the standard deviation of its experimental measurement.

Unless defined otherwise, the meanings of all technical and scientific terms used herein are those commonly understood by one of skill in the art to which this invention belongs. One of skill in the art will also appreciate that any methods and materials similar or equivalent to those described herein can also be used to practice or test the invention. Further, all publications mentioned herein are incorporated by reference in their entireties.

What is claimed is:

1. A composition comprising a Porcine Epidemic Diarrhea Virus (PEDV) and a pharmaceutically-acceptable, non-toxic vehicle, wherein the PEDV has at least 99% identity to SEQ ID NO:1 or SEQ ID NO:2, wherein the PEDV is conjugated or linked to a non-PEDV peptide or polysaccharide.

2. The composition of claim 1, further comprising an effective amount of an immunological adjuvant.

3. The composition of claim 1, further comprising a second immunogenic composition.

* * * * *

SEQUENCE LISTING

```
<160> NUMBER OF SEQ ID NOS: 4

<210> SEQ ID NO 1
<211> LENGTH: 27990
<212> TYPE: DNA
<213> ORGANISM: Porcine epidemic diarrhea virus

<400> SEQUENCE: 1 cttttctag actcttgtct actcaattca actaaacgaa attttgtcct tccggccgca      60
tgtccatgct gctggaagct gacgtggaat ttcattaggt ttgcttaagt agccatcgca     120
agtgctgtgc tgtcctctag ttcctggttg gcgttccgtc gccttctaca tactagacaa     180
acagccttcc tccggttccg tctgggggtt gtgtggataa ctagttccgt ctagtttgaa     240
accagtaact gtcggctatg gctagcaacc atgttacatt ggcttttgcc aatgatgcag     300
aaatttcagc ttttggcttt tgcactgcta gtgaagccgt ctcatactat tctgaggccg     360
ccgctagtgg atttatgcaa tgccgtttcg tgtccttcga tctcgctgac actgttgagg     420
gattgcttcc cgaagactat gtcatggtgg tggtcggcac taccaagctt agtgcgtatg     480
tggacacttt tggtagccgc cccaaaaaca tttgtggttg gctgttattt tctaactgta     540
attacttcct cgaagagtta gagcttactt ttggtcgtcg tggtggtaac atcgtgccag     600
ttgaccaata catgtgtggc gctgacggta aacctgttct tcaggaatcc gaatgggagt     660
atacagattt ctttgctgac tccgaagacg gtcaactcaa cattgctggt atcacttatg     720
tgaaggcctg gattgtagag cgatcggatg tctcttatgc gagtcagaat ttaacatcta     780
ttaagtctat tacttactgt tcaacctatg agcatacttt tcctgatggt actgccatga     840
aggttgcacg tactccaaag attaagaaga ctgttgtctt gtctgagcca cttgctacta     900
```

```
tctacaggga aattggttct ccttttgtgg ataatgggag cgatgctcgt tctatcatta    960
agagaccagt gttcctccac gcttttgtta agtgtaagtg tggtagttat cattggactg   1020
ttggtgattg gacttcctat gtctccactt gctgtggctt taagtgtaag ccagtccttg   1080
tggcttcatg ctctgctacg cctggttctg ttgtggttac gcgcgctggt gctggcactg   1140
gtgttaagta ttacaacaac atgttcctgc gccatgtggc agacattgat gggttggcat   1200
tctggcgaat tctcaaggtg cagtccaaag acgacctcgc ttgctctggt aaattccttg   1260
aacaccatga ggaaggtttc acagatcctt gctactttt gaatgactcg agcattgcta   1320
ctaagctcaa gtttgacatc cttagtggca agttttctga tgaagtcaaa caagctatct   1380
ttgctggtca tgttgttgtt ggcagcgcgc tcgttgacat tgttgacgat gcactgggac   1440
agccttggtt tatacgtaag cttggtgacc ttgcaagtgc agcttgggag cagcttaagg   1500
ctgtcgttag aggccttaac ctcctgtctg atgaggtcgt gctctttggc aaaagactta   1560
gctgtgccac tcttagtatc gttaacggtg ttttgagtt catcgccgaa gtgcctgaga   1620
agttggctgc ggctgttaca gttttgtca acttcttgaa tgagctttt gagtctgcct   1680 gtgactgctt aaaggtcgga ggtaaaacct taacaaggt tggctcttat gttctttttg   1740
acaacgcatt ggttaagctt gtcaaggcaa aagttcgcgg cccacgacag gcaggtgttt   1800
gtgaagttcg ttacacaagc cttgttattg gagtactac caaggtggtt ccaagcgcg   1860 ttgaaaatgc caatgtgaat ctcgtcgtcg ttgacgagga tgtgaccctc aacaccactg   1920
gtcgtacagt tgttgttgac ggacttgcat tcttcgagag tgacgggttt tacagacatc   1980
ttgctgatgc tgacgttgtc attgaacatc ctgtttataa gtctgcttgt gagctcaagc   2040 cagttttga gtgtgaccca atacctgatt ttcctatgcc tgtggccgct agtgttgcag   2100
agctttgtgt gcaaactgat ctgttgctta aaaattacaa cactccttat aaaacttaca   2160
gctgcgttgt gagaggtgat aagtgttgta tcacttgcac cttacatttc acagcaccaa   2220
gttatatgga ggctgctgct aatttgtag acctctgtac caagaacatt ggtactgctg   2280
gttttcatga gttttacatt acggcccatg aacaacagga tctgcaaggg ttcgtaacca   2340
cttgttgcac gatgtcaggt tttgagtgtt ttatgcctat aatcccacag tgtccagcag   2400
tgcttgaaga gattgatggt ggtagcatct ggcggtcttt tatcactggt cttaatacaa   2460
tgtgggattt ttgcaagcat cttaaagtca gctttggact agatggcatt gttgtcactg   2520
tagcacgcaa atttaaacga cttggtgctc tcttggcaga aatgtataac acttaccttt   2580
caactgtggt ggaaaacttg gtactggccg gtgttagctt caagtattat gccaccagtg   2640
tcccaaaaat tgttttgggc tgttgttttc acagtgttaa aagtgttctt gcaagtgcct   2700
tccagattcc tgtccaggca ggcgttgaga gtttaaagt cttccttaac tgtgttcacc   2760
ctgttgtacc acgtgtcatt gaaacttctt ttgtggaatt agaagagacg acatttaaac   2820
caccagcact caatggtagt attgctattg ttgatgctt tgctttctat tatgatggaa   2880
cactatacta tcccaccgat ggtaatagcg ttgttcctat ctgctttaag aagaaaggtg   2940
gtggtgatgt caaattctct gatgaagtct ctgttaaaac cattgaccca gtttataagg   3000
tctcccttga atttgagttc gagtctgaga ctattatggc tgtgcttaat aaggctgttg   3060
gtaattgtat caaggttaca ggtggttggg acgatgttgt tgagtatatc aatgttgcca   3120
ttgaggttct taaagatcac atcgatgtgc ctaagtacta catctatgat gaggaaggtg   3180
gcaccgatcc taatctgccc gtaatggttt ctcagtggcc gttgaatgat gacacgatct   3240
```

```
cacaggatct gcttgatgtt gaagttgtta ctgatgcgcc agttgatttc gagggtgatg    3300
aagtagactc ctctgaccct gataaggtgg cagacgtggc taactctgag cctgaggatg    3360
acggtcttaa tgtagctcct gaaacaaatg tagagtctga agttgaggaa gttgccgcaa    3420
ccttgtcctt tattaaagat acaccttcca cagttactaa ggatcctttt gcttttgact    3480
ttgcaagcta tggaggactt aaggttttaa dacaatctca taacaactgc tgggttactt    3540
ctaccttggt gcagctacaa ttgcttggca tcgttgatga ccctgcaatg gagcttttta    3600
gtgctggtag agttggtcca atggttcgca aatgctatga gtcacaaaag gctatcttgg    3660
gatctttggg tgatgtgtcg gcttgcctag agtctctgac taaggaccta cacacactta    3720
agattacctg ttctgtagtc tgtggttgtg gtactggtga acgtatctat gatggttgtg    3780
cttttcgtat gacgccaact ttggaaccgt tcccatatgg tgcttgtgct cagtgtgctc    3840
aagttttgat gcacactttt aaaagtattg ttggcaccgg catcttttgt cgagatacta    3900
ctgctctctc cttggattct ttggttgtaa aacctctttg tgcggctgct tttataggca    3960
aggatagtgg tcattatgtc actaactttt atgatgctgc tatggctatt gatggttatg    4020
gtcgtcatca dataaagtat gacacactga acactatttg tgttaaagac gttaattgga    4080
cagcaccttt tgtcccagac gttgagcctg tattggagcc tgttgtcaaa ccttctcatt    4140
cttataagaa tgttgatttt taccaaggag attttagtga ccttgttaaa cttccatgtg    4200
attttgttgt taatgctgca atgagaattt tgtctcacgg tggcggcata gcaaaggcca    4260
ttgatgttta taccaagggc atgttgcaga agtgctcgaa tgattacatt aaagcacacg    4320
gtcccattaa agttggacgt ggtgtcatgt tggaggcatt aggtcttaag gtctttaatg    4380
ttgttggtcc acgtaagggt aagcatgcac ctgagcttct tgttaaggct tataagtccg    4440
tttttgctaa ttcaggtgtt gctcttacac ctttgattag tgttggaatt tttagtgttc    4500
ctttggaaga atctttatct gcttttcttg catgtgttgg tgatcgccac tgtaagtgct    4560
tttgttatag tgacaaagag cgcgaggcga tcattaatta catggatggc ttggtagatg    4620
ctattttcaa agatgcgctt gttgatacta ctcctgtcca ggaagatgtt caacaagttt    4680
cacaaaaacc agttttgcct aattttgaac ctttcaggat tgaaggtgct catgctttct    4740
atgagtgcaa ccctgaaggt ttgatgtcat taggtgctga taagctggtg ttgtttacaa    4800
attccaattt ggattttgt agcgttggta agtgtcttaa caatgtgacc ggcggtgcat    4860
tgcttgaagc cataaatgta tttaaaaaga gtaacaaaac agtgcctgct ggcaactgtg    4920
ttacttttga gtgtgcagac atgatttcta ttactatggt agtattgcca tctgatggtg    4980
atgctaatta tgacaaaaat tatgcacgcg ccgtcgtcaa ggtatctaag cttaaaggca    5040
agttattgct tgctgttggt gatgccacgt tgtattccaa gttgtcccat ctcagcgtgg    5100
taggtttcgt atccacacct gatgatgtgg agcgtttcta cgcaaataag agtgtggtta    5160
ttaaagtcac tgaggataca cgtagtgtta aggctgttaa agtagaatcc actgttactt    5220
atggacaaca aattggaccct tgtcttgtta atgacaccgt tgtcacagac aacaaacctg    5280
ttgttgctga tgttgtagct aaggttgtac caagtgctaa ttgggattca cattatggtt    5340
ttgataaggc tggtgagttc cacatgctag accatactgg gtttgtcttt cctagtgaag    5400
ttgttaacgg taggcgtgtg cttaaaacca cagataataa ctgttgggtt aatgttacat    5460
gtttacaatt acagtttgct agatttaggt tcaagtcagc aggtctacag gctatgtggg    5520
agtcctattg tactggtgat gttgctatgt ttgtgcattg gttgtactgg cttactggtg    5580
ttgacaaagg tcagcctagt gattcagaaa atgcacttaa catgttgtcc aagtacattg    5640
```

```
tttctgctgg ttctgtcact attgaacgtg tcacgcatga cggctgttgt tgtagtaagc    5700
gtgttgtcac tgcaccagtt gtgaatgcta gcgtattgaa gcttggcgtc gaggatggtc    5760
tttgtccaca tggtcttaac tacattgaca agttgttgt agttaaaggt actacaattg     5820
ttgtcaatgt tggaaaacct gtagtggcac catcacacct ctttcttaag ggtgtttctt    5880
acacaacatt cctagataat ggtaacggtg ttgtcggcca ttatactgtt tttgatcatg    5940
acactggtat ggtgcatgat ggagatgctt ttgtaccggg tgatctcaat gtatctcctg    6000
ttacaaatgt tgtcgtctca gagcagacgg ctgttgtgat aaagaccct gtgaagaaag     6060 tagagttaga cgctacaaag ctgttagaca ctatgcatta tgcatcggaa agattctttt    6120
cctttggtga ttttatgtca cgtaatttaa ttacagtgtt tttgtacatc cttagcattt    6180
tgggtctctg ttttagggcc tttcgtaaga gggatgttaa agttctagct ggtgtacccc    6240
aacgtactgg tattatattg cgtaaaagtg tgcgctataa tgcaaaggcg ttgggtgtct    6300
tcttcaagct aaaactttat tggttcaaag ttcttggtaa gtttagtttg ggtatttatg    6360
cattgtatgc attactattc atgacaatac gctttacacc tataggtggc cctgtttgtg    6420
atgatgttgt tgctggttat gctaattcta gttttgacaa gaatgagtat tgcaacagtg    6480
ttatttgtaa ggtctgtctc tatgggtacc aggaacttttc agacttctct cacacacagg    6540
tagtatggca acaccttaga gacccattaa ttggtaatgt gatgccttc ttttatttgg     6600 catttctggc aattttttggg ggtgtttatg taaaggctat tactctctat tttatttttcc    6660 agtaccttaa cattcttggt gtgttttttgg gcctacaaca gtccatttgg ttttttgcagc    6720 ttgtgccttt tgatgtcttt ggtgacgaga tcgtcgtctt tttcatcgtt acacgcgtat    6780
tgatgttcct taagcatgtt ttccttggct gcgataaggc atcttgtgtg gcttgctcta    6840
agagtgctcg ccttaagcgc gttcctgtcc agactatttt tcagggtact agcaaatcct    6900
tctacgtaca tgccaatggt ggttctaagt tctgtaagaa gcacaatttc ttttgtttaa    6960
attgtgattc ttatggtcca ggctgcactt ttattaatga cgtcattgca actgaagttg    7020
gtaatgttgt caaacttaat gtgctaccga caggtcctgc cactattctt attgacaagg    7080
ttgaattcag taatggtttt tactatcttt atagtggtga cacattttgg aagtacaact    7140
ttgacataac agatagcaaa tacacttgca agaatcact taaaaattgt agcataatca     7200
cagactttat tgttttttaac aataatggtt ccaatgtaaa tcaggttaag aatgcatgtg    7260
tttatttttc acagatgctt tgtaaacctg ttaagttagt ggactcagcg ttgttggcca    7320
gtttgtctgt tgatttttggt gcaagcttac atagtgcttt tgttagtgtg ttgtcgaata    7380
gttttggcaa agatctgtca agttgtaatg acatgcagga ttgcaagagc acattgggtt    7440
ttgatgatgt accattggat acctttaatg ctgctgttgc tgaggctcat cgttacgatg    7500
tcctcttgac tgacatgtcg ttcaacaatt ttaccaccag ttatgcaaaa ccagaggaaa    7560
aatttcccgt ccatgacatt gccacgtgta tgcgtgtagg tgccaagatt gttaatcata    7620
acgttcttgt caaggatagt atacctgtgg tgtggcttgt acgtgatttc attgcccttt    7680
cggaagaaac taggaagtac attattcgta cgactaaagt taagggtata accttcatgt    7740 tgaccttttaa tgattgtcgt atgcacacta ccatacctac tgtttgcatt gcaaataaga    7800
agggtgcagg tcttcctagt ttttcaaagg ttaagaaatt cttctggttt ttgtgtctgt    7860
tcatggttgc tgttttctttt gcactaagct ttccttgatttt tagtactcag gttagcagtg    7920
atagcgatta tgacttcaag tatattgaga gtggccagtt gaagacttttt gacaatccac    7980
```

```
ttagttgtgt gcataatgtc tttagtaact tcgaccagtg gcatgatgcc aagtttggtt    8040
tcaccccgt  caacaatcct agttgtccta tagtcgttgg tgtatcagac gaagctcgca    8100
ctgttccagg tatyccagca ggtgtttatt tagctggtaa aacacttgtt tttgctatta    8160
acaccatttt tggtacatct ggtttgtgct ttgatgctag tggcgttgct gataagggcg    8220
cttgcatttt taattcggct tgcaccacat tatctggttt gggtggaact gctgtctact    8280
gttataagaa tggtctagtt gaaggtgcta aactttatag tgagttggca cctcatagct    8340
actataaaat ggtagatggt aatgctgtgt ctttacctga aattatttca cgcggctttg    8400
gcatccgtac tatccgtaca aaggctatga cctactgtcg cgttggccag tgtgtgcaat    8460
ctgcagaagg tgtttgtttt ggcgccgata gattctttgt ctataatgca gaatctggtt    8520
ctgactttgt ttgtggcaca gggctcttta cattgttgat gaacgttatt agtgtttttt    8580
ccaagacagt accagtaact gtgttgtctg gtcaaatact ttttaattgc attattgctt    8640
ttgctgctgt tgcggtgtgt ttcttattta caaagtttaa gcgcatgttc ggtgatatgt    8700
ctgttggcgt tttcactgtc ggtgcttgta cttttgttgaa caatgtttct tacattgtaa    8760
cacagaacac acttggcatg ttgggctatg caactttgta cttcttgtgc actaaaggtg    8820
ttagatatat gtggatttgg catttgggat ttttgatctc atatatactt attgcaccat    8880
ggtgggtttt gatggtttat gccttttcgg ccattttga  gtttatgcct aacctttta    8940
agcttaaggt ttcaacacaa cttttgagg  gtgacaagtt cgtaggctct tttgaaaatg    9000
ctgcagcagg tacatttgtg cttgatatgc atgcctatga gagacttgcc aactctatct    9060
caactgaaaa actgcgtcag tatgctagta cttacaataa gtacaagtat tattcaggca    9120
gtgcttcaga ggctgattac aggcttgctt gttttgccca tttggccaag gctatgatgg    9180
attatgcttc taatcacaat gacacgttat acacaccacc cactgtgagt tacaattcaa    9240
ctctacaggc tggcttgcgt aagatggcac aaccatctgg tgttgttgag aagtgcatag    9300
ttcgtgtttg ctatggtaat atggctctta atggcctatg gcttggtgat actgttatgt    9360
gcccacgcca tgttatagcg tctagtacta ctagcactat agattatgac tatgcccttt    9420
ctgttttacg cctccacaac ttctccattt catctggtaa tgttttccta ggtgttgtgg    9480
gtgtaaccat gcgaggtgct tgttgcaga  taaaggttaa tcaaaacaat gtccacacgc    9540
ctaagtacac ctatcgcaca gttagaccag gtgaatcttt taatatcttg gcgtgctatg    9600
atggtgctgc agctggtgtt tatggcgtta acatgcgctc taattacact attagaggct    9660
cgttcattaa tggcgcttgt ggttcacctg gttataatat taacaatggt accgttgagt    9720
tttgctattt acatcagctt gaacttggtt caggctgtca tgttggtagc gacttagatg    9780
gtgttatgta tggtggttat gaggaccaac ctacttgca  agttgaaggc gctagtagtc    9840
tgtttacaga gaatgtgttg gcatttcttt atgcagcact cattaatggt tctacctggt    9900
ggcttagttc ttctaggatt gctgtagaca ggtttaatga gtgggctgtt cataatggta    9960
tgacaacagt aggtaatact gattgctttt ctattcttgc tgctaagact ggtgttgatg   10020
tacaacgttt gttggcctca atccagtctc tgcataagaa ttttggtgga aagcaaattc   10080
ttggctatac ctcgttgaca gatgagttta ctacaggtga agttatacgt caaatgtatg   10140
gcgttaatct tcagagtggt tatgtttcac gcgcctgcag aaatgtcttg ctggttggtt   10200
ctttttctgac tttcttttgg tcagaattag tttcctacac taagttcttt tgggtaaatc   10260
ctggttatgt cacacctatg tttgcgtgtt tgtcattgct gtcctcactt ttgatgttca   10320
cactcaagca taagacattg ttcttccagg tctttctaat acctgctctg attgttacat   10380
```

```
cttgcattaa tttggcattt gatgttgaag tctacaacta tttggcagag cattttgatt   10440
accatgtttc tctcatgggt tttaatgcac aaggtcttgt taacatcttt gtctgctttg   10500
ttgttaccat tttacacggc acatacacat ggcgcttttt taacacacct gtgagttctg   10560
tcacttatgt ggtagctttg atgactgcgg catataacta tttttacgct agtgacattc   10620
ttagttgtgc tatgacacta tttgctagtg tgactggcaa ctggttcgtt ggtgctgttt   10680
gttataaagc tgctgtttat attgccttga gatttcctac ttttgtggct attttggtg    10740 atattaagag tgttatgttc tgttaccttg tgttgggtta ttttacctgt tgtttctacg   10800
gtattctcta ctggttcaac aggttttta  aggttagtgt aggtgtctat gactatactg   10860
ttagtgctgc tgagtttaag tatatggttg ctaacggcct acgtgcacca actggaacac   10920
ttgattcact acttctgtct gccaaattga ttggtattgg tggtgagcgg aatattaaga   10980
tttcttccgt tcagtctaaa ctgactgata ttaagtgtag taacgttgtg cttttaggct   11040
gtctctctag catgaatgtc tcagcaaatt caacagaatg ggcctattgt gttgacttgc   11100
ataacaagat caacttgtgt aatgacccag aaaaagcgca ggaaatgcta cttgctttgt   11160
tggcattttt ccttagtaag aatagtgctt ttggttttgga tgacttattg gaatcctatt   11220
ttaatgacaa tagtatgttg cagagtgttg catctactta tgtcggtttg ccttcttatg   11280
tcatttatga aaatgcacgc caacagtatg aagatgctgt taataatggt tctccacctc   11340
agttggttaa gcaattgcgc catgccatga atgtagcaaa gagcgaattt gaccgtgagg   11400
cttctactca gcgtaagctt gatagaatgg cggaacaggc tgcagcacag atgtacaaag   11460
aggcaagagc agttaatagg aagtccaaag ttgtaagtgc tatgcattca ctgcttttg    11520 gtatgttgag acgtttggac atgtcttctg tagacaccat tctcaacttg gcaaaggatg   11580
gggttgtacc tctgtctgtc ataccggcag tcagtgctac taagcttaac attgttactt   11640
ctgatatcga ttcttataat cgtatccagc gtgagggatg tgtccattac gctggtacca   11700
tttggaatat aattgatatc aaggacaatg atggcaaggt ggtacacgtt aaggaggtaa   11760
ccgcacagaa tgctgagtcc ctgtcatggc ccctggtcct tgggtgtgag cgtattgtca   11820
agctccagaa taatgaaatt attcctggta agctgaagca gcgctccatt aaggcagaag   11880
gagatggcat agttggagaa ggtaaggcac tttacaataa tgagggtgga cgtacttta    11940 tgtatgcttt catctcggac aaaccggacc tgcgtgtagt taagtgggag ttcgatggtg   12000
gttgtaacac tattgagcta gaaccaccac gtaagttctt ggtggattct cctaatggtg   12060
cacagatcaa gtatctctac tttgttcgta accttaacac gttacgtagg ggtgctgttc   12120
ttggctacat aggtgccact gtacgcttgc aggctggtaa acaaacagaa caggctatta   12180
actcttcatt gttgacactt tgcgcttccg ctgtggatcc tgctaagacc tacatcgatg   12240
ctgtcaaaag tggtcacaaa ccagtaggta actgcgttaa gatgttggcc aatggttctg   12300
gtaatggaca agctgttact aatggtgtgg aggctagtac taaccaggat tcatacggtg   12360
gtgcttccgt gtgtctatat tgtagagcac atgttgagca tccatctatg gatggttttt   12420
gcagactgaa aggcaagtac gtacaggtgc cactaggtac agtggatcct atacgttttg   12480
tacttgagaa tgacgtttgc aaggtctgtg gttgttggct ggctaatggc tgcacttgtg   12540
acagatccat tatgcaaagc actgatatgg cttatttaaa cgagtacggg gctctagtgc   12600
agctcgacta gagccctgta acggtactga tacacaacat gtgtatcgtg cttttgacat   12660
ctacaacaag gatgttgctt gtctaggtaa attcctcaag gtgaactgtg ttcgcctgaa   12720
```

```
gaatttggat aagcatgatg cattctatgt tgtcaaaaga tgtaccaagt ctgcgatgga    12780
acacgagcaa tccatctata gcagacttga aaagtgtgga gccgtagctg aacacgattt    12840
cttcacttgg aaggatggtc gtgcaatcta tggtaacgtt tgtagaaagg atcttaccga    12900
gtatactatg atggatttgt gttacgcttt acgtaacttt gatgaaaaca attgcgatgt    12960
tcttaagagc attttaatta aggtaggcgc ttgtgaggag tcctacttca ataataaagt    13020
ctggtttgac cctgttgaaa atgaagacat tcatcgtgtt tatgcattgt taggtaccat    13080
tgtttcacgt gctatgctta aatgcgttaa gttctgtgat gcaatggttg aacaaggtat    13140
agttggtgtt gtcacattag ataatcagga tcttaatggt gattttatg attttggtga    13200 ttttacttgt agcatcaagg gaatgggtat acccatttgc acatcatatt actcttatat    13260
gatgcctgtt atgggtatga ctaattgcct tgctagtgag tgttttgtta agagtgatat    13320
atttggtgag gatttcaagt catatgacct gctggaatat gatttcacgg agcataagac    13380
agcactcttc aacaagtatt tcaagtattg gggactgcaa taccacccta actgtgtgga    13440
ctgcagtgat gagcagtgca tagttcactg tgccaacttc aatacgttgt tttccactac    13500
tatacctatt acggcatttg gacctttgtg tcgcaagtgt tggattgatg gtgttccact    13560
ggtaactaca gctggttatc attttaaaca gttaggtata gtttggaaca atgacctcaa    13620
cttacactct agcaggctct ctattaacga actactccag ttttgtagtg atcctgcatt    13680
gcttatagca tcatcaccag cccttgttga tcagcgtact gtttgctttt cagttgcagc    13740
gctaggtaca ggtatgacta accagactgt taaacctggc catttcaata aggagtttta    13800
tgacttctta cttgagcaag gtttcttttc tgagggctct gagcttactt taaagcactt    13860
cttctttgca cagaagggtg atgcagctgt taaggatttt gactactata ggtataatag    13920
acctactgtt ctggacattt gccaagctcg cgtcgtgtat caaatagtgc aacgctattt    13980
tgatatttac gaaggtggtt gtatcactgc taaagaagtg gttgttacaa accttaacaa    14040
gagcgcaggt tatcctttga acaagtttgg taaagctggt ctttactatg agtctttatc    14100
ctatgaggaa caggatgaac tttatgctta tactaagcgt aacatcctgc ccactatgac    14160
acagctcaac cttaaaatgt ctataagtgg caaagaacgt gcacgcacag tgggtggtgt    14220
ttcgcttttg tcaaccatga ctactcggca gtatcaccag aaacaccttt agtccatagt    14280
taatactagg ggcgcttcgg ttgttattgg tactactaag ttttatggtg gttgggacaa    14340
tatgcttaag aaccttattg atggtgtcga aaatccgtgt cttatgggtt gggattaccc    14400
aaagtgcgac agagcactgc ccaatatgat acgcatgatt tcagccatga ttttaggctc    14460
taagcacacc acatgctgca gttccactga ccgcttttc aggttgtgca atgaattggc    14520
tcaagtcctt actgaggttg tttattctaa tggaggtttt tatttgaagc aggtggtac    14580 tacctctggt gatgcaacca ccgcatatgc aaactcagtt tcaatatct tccaagcagt    14640 aagtgccaat gttaacaaac ttcttagtgt tgacagcaat gtctgtcata atttagaagt    14700
taagcaattg cagcgtaagc tttatgagtg ctgttataga tcaactaccg tcgatgacca    14760
gttcgtcgtt gagtattatg gttacttgcg taaacatttt tcaatgatga ttcttcctga    14820
tgatggcgtt gtttgttaca acaatgacta tgcatcactt ggttatgtcg ctgatctaa    14880 cgcattcaag gctgttttgt attaccagaa caatgtcttc atgagcgcct ctaaatgttg    14940
gatcgagcct gacattaata aaggtcctca tgaattttgc tcgcagcata ctatgcagat    15000
tgtcgataaa gatggtactt actacctacc ttaccctgat cctcaagaa tcctctctgc    15060 aggtgtgttt gttgacgacg ttgttaaaac tgatgcagtt gtattgcttg aacgttatgt    15120
```

```
gtcattggct atagatgcct acccgttatc taagcatgaa aaccctgaat ataagaaggt   15180
gttttatgtg cttttggatt gggttaagca cctgtataaa actttgaatg ctggtgtgtt   15240
agagtctttt tctgtcacac ttttggaaga ttctactgct aaattctggg atgagagctt   15300
ttatgccaac atgtatgaga aatctgcagt tttgcaatct gcagggcttt gtgttgtttg   15360
tggctctcaa actgttttac gttgtggtga ttgtctacgg cgtcctatgc tttgtactaa   15420
gtgtgcttat gatcatgtca ttggaacaac tcacaagttc attttggcta tcactccata   15480
tgtgtgttgt gcttcagatt gtggtgtcaa tgatgtaact aagctctact taggtggtct   15540
tagttattgg tgtcatgaac acaagccacg tcttgcattc ccgttgtgtt ctgctggtaa   15600 tgttttggt ttgtacaaaa attctgctac cggctcaccc gatgttgagg actttaatcg   15660
cattgctaca tccgattgga ctgatgtttc tgactacagg ttggcaaatg atgtcaaaga   15720
ctcattgcgt ctatttgcag cggaaactat caaggccaag gaggagagcg ttaagtcatc   15780
ctacgcttgt gcaacactac atgaggttgt aggacctaaa gagttgttgc tcaaatggga   15840
agtcggcaga cccaaaccac ctcttaatag aaattcggtt ttcacttgtt atcatataac   15900
gaagaacacc aaatttcaaa tcggtgagtt tgtgtttgag aaggcagaat atgataatga   15960
tgctgtaaca tataaaacta ccgccacaac aaaacttgtt cctggcatgg ttttttgtgct   16020 tacctcacat aatgttcagc cattgcgcgc accgaccatt gctaatcaag aacgttattc   16080
cactatacat aagttgcacc ctgcttttaa catacctgaa gcttattcta gcttagtgcc   16140
ctattaccaa ctgattggta agcagaagat tacaactatc cagggacctc caggtagtgg   16200
taaatctcac tgtgttatag ggctaggttt gtactatcca ggtgcacgta tagtgtttac   16260
agcttgttct catgcagcgg tcgattcact ttgtgtgaaa gcctccactg cttatagcaa   16320
tgacaaatgt tcacgcatca taccacagcg tgctcgtgtt gagtgttatg acggtttcaa   16380
gtctaataat actagtgctc agtacctttt ctccactgtc aatgctttgc cagagtgcaa   16440
tgcggacatt gttgtggtgg atgaggtttc tatgtgcact aattatgact tgtctgtcat   16500
aaatcagcgc atcagctata ggcatgtagt ctatgttggt gaccctcaac agctgcctgc   16560
accacgtgtt atgatttcac gtggtacttt ggaaccaaag gactacaacg ttgtcactca   16620
acgcatgtgt gcccttaagc ctgatgtttt cttgcacaag tgttatcgct gtcctgctga   16680
gatagtgcgc actgtgtctg agatggtcta tgaaaaccaa ttcattcctg tgcacccaga   16740
tagcaagcag tgttttaaaa tcttttgcaa gggtaatgtt caggttgaca atggttcaag   16800
catcaatcgc aggcaattgg atgttgtgcg tatgttttg gctaaaaacc ctaggtggtc   16860
aaaggctgtt tttatttctc cttataacag ccagaattat gttgccagcc gcatgctagg   16920
tttacaaatt cagacagttg actcatccca gggtagtgag tatgactatg tcatttatac   16980
acaaacttca gatactgccc atgcctgtaa tgttaacagg tttaatgttg ccatcacaag   17040
ggctaagaaa ggcatattat gtataatgtg cgataggtcc ctttttgatg tgcttaaatt   17100
ttttgagctt aaaattgtctg atttgcaggc taatgagggt tgtggtcttt taaagactg   17160 tagcagaggt gatgatctgt tgccaccatc tcacgctaac accttcatgt ctttagcgga   17220 caatttaag actgatcaag atcttgctgt tcaaataggt gttaatgac ccattaaata   17280 tgagcatgtt atctcgttta tgggcttccg ttttgatatc aacatacccca accatcacac   17340 tctcttttgc acacgcgact ttgccatgcg caatgttaga ggttggttgg gttttgacgt   17400
tgaaggagca catgttgttg gctctaacgt cggtacaaat gtcccattgc aattagggtt   17460
```

```
ttctaacggt gttgattttg ttgtcagacc tgaaggttgc gttgtaactg agtctggtga   17520
ctacattaaa cccgtcagag ctcgtgctcc accaggggaa caatttgcac acctttttgcc  17580 tctacttaaa cgcggccaac catgggatgt ggttcgtaag cgtatagtgc aaatgtgtag   17640
tgactacctg gctaacctat cagacatact aattttttgtg ttgtgggctg gtggtttgga  17700
gttgacaact atgcgttact ttgtcaagat tggaccaagc aagagttgtg attgtggtaa   17760
ggttgctact tgttacaata gtgcgctgca tacgtactgt tgtttcaaac atgcccttgg   17820
ttgtgattac ctgtacaatc catactgtat tgatatacag cagtggggat acaagggatc   17880
acttagcctt aaccaccatg agcattgtaa tgtacataga aacgagcatg tggcttctgg   17940
tgatgccata atgactcgct gtctagccat acatgattgc tttgtcaaga acgttgactg   18000
gtccatcaca tacccatttta ttggtaatga ggctgttatt aataagagcg gccgaattgt   18060
gcaatcacac actatgcggt cagttcttaa gttatacaat ccaaaagcca tatatgatat   18120
tggcaaccct aagggcatta gatgtgccgt aacggatgct aagtggttct gctttgacaa   18180
gaatcctact aattctaatg tcaagacatt ggagtatgac tatataacac acggccaatt   18240
tgatgggttg tgcttgtttt ggaattgcaa tgtggacatg tatccagaat tctctgtggt   18300
ctgtcggttt gacactcgct gtaggtcacc actcaacttg gagggttgta atggtggttc   18360
actgtatgtt aataatcatg cattccatac accggctttt gacaagcgtg cttttgccaa   18420
gttgaagcca atgccatttt tcttctatga tgatactgag tgtgacaagt acaggactc    18480 tataaactac gttcctctta gggctagtaa ttgcattact aaatgtaatg ttggtggagc   18540
tgtctgtagt aagcattgtg ctatgtacca tagctatgtt aatgcttaca acacctttac   18600
gtcggcgggc tttacgattt gggtgcccac ttcgtttgac acctacaatc tgtggcagac   18660
atttagtaac aacttgcaag gtcttgagaa cattgctttc aatgtcgtaa agaaaggatc   18720
ttttgttggt gctgaaggtg agcttcctgt agctgtggtt aatgacaaag tgctcgttag   18780
agatggtact gttgatactc ttgttttcac aaacaagaca tcactaccca ctaacgtagc   18840
ttttgagttg tatgccaagc gtaaggtagg actcacccca cccattacga tcctacgtaa   18900
cttgggtgtt gtttgcacat ctaagtgtgt catttgggac tatgaagccg aacgtccact   18960
tactactttt acaaaggatg tctgtaaata taccgacttt gagggtgacg tttgcacact   19020
ctttgataac agcattgttg gttcattaga gcgattctct atgacccaaa atgctgtgct   19080
tatgtcactt acagctgtta aaaagcttac tggcataaag ttaacttatg ttatcttaa    19140 tggtgtccca gttaacacac atgaagataa acctttttact tggtacattt acactaggaa   19200
gaacggcaag ttcgaggact atcctgatgg ctatttttacc caaggtagaa caaccgctga   19260
ttttagccct cgtagtgaca tggaaaagga cttcctaagt atggatatgg gtctgtttat   19320
taacaagtac ggactcgaag attacggctt tgagcacgtt gtgtatggtg atgtttctaa   19380
aaccaccctt ggtggtttac atctactaat ttcgcaggtg cgtctggcct gtatgggtgt   19440
gcttaaaata gacgagtttg tgtctagtaa tgatagcacg ttaaagtctt gtactgttac   19500
atatgctgat aaccctagta gtaagatggt ttgcacgtat atggatctcc ttcttgacga   19560
ttttgtcagc attcttaaat cgttggattt gagtgttgta tctaaagttc atgaagttat   19620
ggtcgattgt aaaatgtgga ggtggatgtt gtggtgtaag gatcataaac tccagacatt   19680
ttatccgcaa cttcaggcca gtgaatggaa atgtggttat tccatgcctt ctatttacaa   19740
gatacaacgt atgtgtttag aaccttgcaa tctctataac tatggtgctg gtattaagtt   19800
acctgatggc attatgtttta acgtagttaa atatacacag ctttgtcaat atcttaatag   19860
```

```
caccacaatg tgtgtacccc atcacatgcg cgtgctacat cttggtgctg gctccgacaa   19920
gggtgttgca cctggcacgg ctgtcttacg acgttggttg ccactggatg ccattatagt   19980
tgacaatgat agtgtggatt acgttagcga tgctgattat agtgttacgg gagattgctc   20040
tacctttatac ctgtcagata agtttgactt agttatatct gatatgtatg atggtaagat   20100
taaaagttgt gatggggaga acgtgtctaa agaaggcttc tttccctata ttaatggtgt   20160
catcactgaa aagttggcac ttggtggtac tgtagctatt aaggtgacgg agtttagttg   20220
gaataagaag ttgtatgaac tcattcagaa gtttgagtat tggacaatgt tctgtaccag   20280
tgttaacacg tcatcgtcag aggcattttt aattggtgtt cactatttag gtgattttgc   20340
aagtggcgct gtgattgacg gcaacactat gcatgccaat tatatcttct ggcgtaattc   20400
cacaattatg actatgtctt acaatagtgt acttgattta agcaagttca attgtaagca   20460
taaggctaca gttgttatta atttaaaaga ttcatccatt agtgatgttg tgttaggttt   20520
gttgaagaat ggtaagttgc tagtgcgtaa taatgacgcc atttgtggtt tttctaatca   20580
tttggtcaac gtaaacaaat gaagtctttta aattacttct ggttgttctt accagtactt   20640
tcaacactca gcctaccaca agatgtcact aggtgccagt ccactattaa cttcaggcgg   20700
ttcttttcaa aatttaatgt gcaggcacct gctgtcgttg tgttgggtgg ttatctacct   20760
agtatgaact cctctagctg gtactgtggc acaggtcttg aaactgctag tggcgtgcat   20820
ggtattttcc tcagttacat cgatgctggt cagggctttg agattggcat ttcacaggag   20880
ccgtttgatc ctagtggtta ccagctttat ttacataagg ccactaatgg taaccataat   20940
gctattgcac gactgcgcat ttgccagttt ccagataata aaacattggg ccctactgtt   21000
aatgatgtta caacaggtcg taactgccta ttcaacaaag ccattccagc ttatatgcag   21060
gatggaaaaa atatcgttgt cggcataaca tgggacaatg atcgtgtcac tgtttttgct   21120
gacaagatct atcattttta tcttaaaaat gattggtccc gtgttgcgac aagatgttac   21180
aataaaagaa gttgtgctat gcaatatgtt tatacaccta cctactacat gcttaatgtt   21240
actagtgcag gtgaggatgg catttattat gaaccatgta cagctaattg cagtggttac   21300
gctgccaatg tgtttgccac tgattctaat ggccacacac cagaaggttt tagttttaat   21360
aattggtttc ttttgtccaa tgattccact tgttgcatg gtaaggtggt ttccaaccaa   21420
cctttgttgg tcaattgtct tttggccatt cctaagattt atggactagg ccaatttttc   21480
tcattcaatc aaacgatgga tggcgtttgt aatggagctg ctgcgcagcg tgcaccagag   21540
gctctgaggt ttaatattaa tgacacctct gtcattcttg ctgaaggctc aattgtactt   21600
catactgctt taggaacaaa tctttctttt gtttgcagta attcttcaga tcctcatcta   21660
gctaccttcg ccatacctct gggtgctacc caagtacctt attattgttt tcttaaagtg   21720
gatacttaca actccactgt ttataaattt ttggctgttt tacctcctac cgtcagggaa   21780
attgtcatca ccaagtatgg tgatgtttat gtcaatgggt ttggatactt gcatctcggt   21840
tgttggatg ctgtcacaat taatttcact ggtcatggca ctgacgatga tgtttctggt   21900
ttttggacca tagcatcgac taattttgtt gatgcactca tcgaagttca aggaaccgcc   21960
attcagcgta ttctttattg tgatgatcct gttagccaac tcaagtgttc tcaggttgct   22020
tttgaccttg acgatggttt ttaccctatt tcttctagaa accttctgag tcatgaacag   22080
ccaatttctt tgttactct gccatcattt aatgatcatt cttttgttaa cattactgta   22140
tctgcttcct ttggtggtca tagtggtgcc aaccttattg catctgacac tactatcaat   22200
```

```
gggtttagtt cttctgtgt tgacactaga caatttacca tttcactgtt ttataacgtt   22260
acaaacagtt atggttatgt gtctaaatca caggacagta attgcccttt caccttgcaa   22320
tctgttaatg attacctgtc ttttagcaaa ttttgtgttt ccaccagcct tttggctagt   22380
gcctgtacca tagatctttt tggttaccct gagtttggta gtggtgttaa gtttacgtcc   22440
ctttactttc aattcacaaa gggtgagttg attactggca cgcctaaacc acttgaaggt   22500
gtcacggacg tttcttttat gactctggat gtgtgtacca agtatactat ctatggcttt   22560
aaaggtgagg gtatcattac ccttacaaat tctagctttt tggcaggtgt ttattacaca   22620
tctgattctg gacagttgtt agcctttaag aatgtcacta gtggtgctgt ttattctgtt   22680
acgccatgtt ctttttcaga gcaggctgca tatgttgatg atgatatagt gggtgttatt   22740
tctagtttgt ctagctccac ttttaacagt actagggagt tgcctggttt cttctaccat   22800
tctaatgatg gctctaattg tacagagcct gtgttggtgt atagtaacat aggtgtttgt   22860
aaatctggca gtattggcta cgtcccatct cagtctggcc aagtcaagat tgcacccacg   22920
gttactggga atattagtat tcccaccaac tttagtatga gtattaggac agaatattta   22980
cagctttaca acacgcctgt tagtgttgat tgtgccacat atgtttgtaa tggtaactct   23040
cgttgtaaac aattactcac ccagtacact gcagcatgta agaccataga gtcagcatta   23100
caactcagcg ctaggcttga gtctgttgaa gttaactcta tgcttactat ttctgaagag   23160
gctctacagt tagctaccat tagttcgttt aatggtgatg gatataattt tactaatgtg   23220
ctgggtgttt ctgtgtatga tcctgcaagt ggcagggtgg tacaaaaaag gtcttttatt   23280
gaagacctgc ttttttaataa agtggttact aatggccttg gtactgttga tgaagactat   23340
aagcgctgtt ctaatggtcg ctctgtggca gatctagtct gtgcacagta ttactctggt   23400
gtcatggtac tacctggtgt tgttgacgct gagaagcttc acatgtatag tgcgtctctc   23460
atcggtggta tggtgctagg aggtttttact tctgcagcgg cattgccttt tagctatgct   23520
gttcaagcta gactcaatta tcttgctcta cagacggatg ttctacagcg gaaccagcaa   23580
ttgcttgctg agtctttaa ctctgctatt ggtaatataa cttcagccct tgagagtgtt   23640
aaagaggcta ttagtcaaac ttccaagggt tgaacactg tggctcatgc gcttactaag   23700
gttcaagagg ttgttaactc gcagggtgca gctttgactc aacttaccgt acagctgcaa   23760
cacaacttcc aagccatttc tagttctatt gatgacattt actctcgact ggacattctt   23820
tcagccgatg ttcaggttga ccgtctcatc accggcagat tatcagcact taatgctttt   23880
gttgctcaaa ccctcactaa gtatactgag gttcaggcta gcaggaagtt agcacagcaa   23940
aaggttaatg agtgcgttaa atcgcaatct cagcgttatg gttttgtgg tggtgatggc   24000
gagcacattt tctctctggt acaggcagca cctcagggcc tgctgttttt acatacagta   24060
cttgtaccga gtgattttgt agatgttatt gccatcgctg gctatgcgt taacgatgaa   24120
attgccttga ctctacgtga gcctggctta gtcttgttta cgcatgaact tcaaaatcat   24180
actgcgacgg aatattttgt tcatcgcgca cgtatgtttg aacctagaaa acctaccgtt   24240
agtgattttg ttcaaattga gagttgtgtg gtcacctatg tcaatttgac tagagaccaa   24300
ctaccagatg taatcccaga ttacatcgat gttaacaaaa cacttgatga gattttagct   24360
tctctgccca atagaactgg tccaagtctt cctttagatg ttttaatgc cacttatctt   24420
aatctcactg gtgaaattgc agatttagag cagcgttcag agtctctccg taatactaca   24480
gaggagctcc aaagtcttat atataatatc aacaacacac tagttgacct tgagtggctc   24540
aaccgagttg agacatatat caagtggccg tggtgggttt ggttgattat tttcattgtt   24600
```

```
ctcatctttg ttgtgtcatt actagtgttc tgctgcattt ccacggggttg ttgtggatgc   24660 tgcggctgct gctgtgcttg tttctcaggt tgttgtaggg gtcctagact tcaaccttac   24720 gaagttttttg aaaaggtcca cgtgcagtga tgtttcttgg acttttttcaa tacacgattg   24780 acacagttgt caaagatgtc tcaaagtctg ctaacttgtc tttggatgct gtccaagagt   24840
tggagctcaa tgtagttcca attagacaag cttcaaatgt gacgggtttt cttttcacca   24900
gtgtttttat ctacttctttt gcactgttta aagcgtcttc tttgaggcgc aattatatta   24960
tgttggcagc gcgttttgct gtcattgttc tttattgccc acttttatat tattgtggtg   25020
catttttaga tgcaactatt atttgttgca cacttattgg caggctttgt ttagtctgct   25080
tttactcctg gcgctataaa aatgcgctct ttattatttt taatactacg acactttctt   25140
tcctcaatgg taaagcagct tattatgacg gcaaatccat tgtgatttta gaaggtggtg   25200
accattacat cacttttggc aactcttttg ttgcttttgt tagtagcatc gacttgtatc   25260
tagctatacg tgggcggcaa gaagctgacc tacagctgtt gcgaactgtt gagcttcttg   25320
atggcaagaa gctttatgtc ttttcgcaac atcaaattgt tggcattact aatgctgcat   25380
ttgactcaat tcaactagac gagtatgcta caattagtga atgataatgg tctagtagtt   25440
aatgttatac tttggctttt cgtactctttt ttcctgctta ttataagcat tactttcgtc   25500
caattggtta atctgtgctt cacttgtcac cggttgtgta atagcgcagt ttacacacct   25560
atagggcgtt tgtatagagt ttataagtct tacatgcaaa tagaccccct ccctagtact   25620
gttattgacg tataaacgaa atatgtctaa cggttctatt cccgttgatg aggtgattca   25680
acaccttaga aactggaatt tcacatggaa tatcatactg acgatactac ttgtagtgct   25740
tcagtatggc cattacaagt actctgcgtt cttgtatggt gtcaagatgg ctattctatg   25800
gatactttgg cctcttgtgt tagcactgtc acttttttgat gcatgggcta gctttcaggt   25860
caattgggtc ttttttgctt tcagcatcct tatggcttgc atcactctta tgctgtggat   25920 aatgtactttt gtcaatagca ttcggttgtg gcgcaggaca cattcttggt ggtctttcaa   25980
tcctgaaaca gacgcgcttc tcactacttc tgtgatgggc cgacaggtct gcattccagt   26040
gcttggagca ccaactggtg taacgctaac actccttagt ggtacattgc ttgtagaggg   26100
ctataaggtt gctactggcg tacaggtaag tcaattacct aatttcgtca cagtcgccaa   26160
ggccactaca acaattgtct acggacgtgt tggtcgttca gtcaatgctt catctggcac   26220
tggttgggct ttctatgtcc ggtccaaaca cggcgactac tcagctgtga gtaatccgag   26280
ttcggttctc acagatagtg agaaagtgct tcatttagtc taaacagaaa ctttatggct   26340
tctgtcagtt ttcaggatcg tggccgcaaa cgggtgccat tatccctcta tgcccctctt   26400
agggttacta atgacaaacc cctttctaag gtacttgcaa ataatgctgt acccactaat   26460
aaaggaaata aggaccagca aattggatac tggaatgagc aaattcgctg gcgcatgcgc   26520
cgtggtgagc gaattgaaca accttccaat tggcatttct actacctcgg aacaggacct   26580
cacgccgacc tccgctatag gactcgtact gagggtgttt tctgggttgc taaagaaggc   26640
gcaaagactg aacccactaa cctgggtgtc agaaaggcgt ctgaaaagcc aattattcca   26700
aatttctctc aacagcttcc cagcgtagtt gagattgttg aacctaacac acctcctact   26760
tcacgtgcaa attcacgtag caggagtcgt ggtaatggca acaacaggtc cagatctcca   26820
agtaacaaca gaggcaataa ccagtcccgc ggtaattcac agaatcgtgg aaataaccag   26880
ggtcgtggag cttctcagaa cagaggaggc aataataata caataacaa gtctcgtaac   26940
```

| | | |
|---|---|---|
| cagtccaaga acagaaacca gtcaaatgac cgtggtggtg taacatcacg cgatgatctg | 27000 | |
| gtggctgctg tcaaggatgc ccttaaatct ttgggtattg gcgaaaaccc tgacaagctt | 27060 | |
| aagcaacagc agaagcccaa acaggaaagg tctgacagca gcggcaaaaa tacacctaag | 27120 | |
| aagaacaaat ccagagccac ttcgaaagaa cgtgacctca agacatccc agagtggagg | 27180 | |
| agaattccca agggcgaaaa tagcgtagca gcttgcttcg acccagggg aggcttcaaa | 27240 | |
| aattttggag atgcggaatt tgtcgaaaaa ggtgttgayg cctcaggcta tgctcagatc | 27300 | |
| gccagtttag caccaaatgt tgcagcattg ctctttggtg gtaatgtggc tgttcgtgag | 27360 | |
| ctagcggact cttacgagat tacatataat tataaaatga ctgtgccaaa gtctgatcca | 27420 | |
| aatgtagagc ttcttgtttc acaggtggat gcatttaaaa ctgggaatgc aaaccccag | 27480 | |
| agaaagaagg aaaagaagaa caagcgtgaa accacgcagc agctgaatga agaggccatc | 27540 | |
| tacgatgatg tgggtgtgcc atctgatgtg actcatgcca atttggaatg ggacacagct | 27600 | |
| gttgatggtg gtgacacggc cgttgaaatt atcaacgaga tcttcgacac aggaaattaa | 27660 | |
| acaatgtttg actggcttat cctggctatg tcccaggta gtgccattac actgttatta | 27720 | |
| ctgagtgttt ttttagcgac ttggctgctg ggctatggct ttgccctcta actagcggtc | 27780 | |
| ttggtcttgc acacaacggt aagccagtgg taatgtcagt gcaagaagga tattaccata | 27840 | |
| gcactgtcat gaggggaacg cagtacctt tcatctaaac ctttgcacga gtaatcaaag | 27900 | |
| atccgcttga cgagcctata tggaagagcg tgccaggtat ttgactcaag gactgttagt | 27960 | |
| aactgaagac ctgacggtgt tgatatggat | 27990 | |

<210> SEQ ID NO 2
<211> LENGTH: 28005
<212> TYPE: DNA
<213> ORGANISM: Porcine epidemic diarrhea virus

<400> SEQUENCE: 2

| | | |
|---|---|---|
| ctacggatag ttagctcttt ttctagactc ttgtctactc aattcaacta aacgaaattt | 60 | |
| tgtccttccg gccgcatgtc catgctgctg gaagctgacg tggaatttca ttaggttttgc | 120 | |
| ttaagtagcc atcgcaagtg ctgtgctgtc ctctagttcc tggttggcgt tccgtcgcct | 180 | |
| tctacatact agacaaacag ccttcctccg gttccgtctg ggggttgtgt ggataactag | 240 | |
| ttccgtctag tttgaaacca gtaactgtcg gctatggcta gcaaccatgt tacattggct | 300 | |
| tttgccaatg atgcagaaat tcagcttttt ggcttttgca ctgctagtga agccgtctca | 360 | |
| tactattctg aggccgccgc tagtggattt atgcaatgcc gtttcgtgtc cttcgatctc | 420 | |
| gctgacactg ttgagggatt gcttcccgaa gactatgtca tggtggtggt cggcactacc | 480 | |
| aagcttagtg cgtatgtgga cactttggt agccgcccca aaaacatttg tggttggctg | 540 | |
| ttattttcta actgtaatta cttcctcgaa gagttagagc ttactttggg tcgtcgtggt | 600 | |
| ggtaacatcg tgccagttga ccaatacatg tgtggcgctg acggtaaacc tgttcttcag | 660 | |
| gaatccgaat gggagtatac agatttcttt gctgactccg aagacggtca actcaacatt | 720 | |
| gctggtatca cttatgtgaa ggcctggatt gtagagcgat cggatgtctc ttatgcgagt | 780 | |
| cagaatttaa catctattaa gtctattact tactgttcaa cctatgagca actttttcct | 840 | |
| gatggtactg ccatgaaggt tgcacgtact ccaaagatta gaagactgt tgtcttgtct | 900 | |
| gagccacttg ctactatcta cagggaaatt ggttctcctt ttgtggataa tgggagcgat | 960 | |
| gctcgttcta tcattaagag accagtgttc ctccacgctt ttgttaagtg taagtgtggt | 1020 | |
| agttatcatt ggactgttgg tgattggact tcctatgtct ccacttgctg tggctttaag | 1080 | |

```
tgtaagccag tccttgtggc ttcatgctct gctacgcctg gttctgttgt ggttacgcgc   1140
gctggtgctg gcactggtgt taagtattac aacaacatgt tcctgcgcca gtgtggcagac  1200 attgatgggt tggcattctg gcgaattctc aaggtgcagt ccaaagacga cctcgcttgc   1260
tctggtaaat tccttgaaca ccatgaggaa ggtttcacag atccttgcta cttttttgaat  1320 gactcgagca ttgctactaa gctcaagttt gacatcctta gtggcaagtt ttctgatgaa   1380
gtcaaacaag ctatctttgc tggtcatgtt gttgttggca gcgcgctcgt tgacattgtt   1440
gacgatgcac tgggacagcc ttggtttata cgtaagcttg gtgaccttgc aagtgcagct   1500
tgggagcagc ttaaggctgt cgttagaggc cttaacctcc tgtctgatga ggtcgtgctc   1560
tttggcaaaa gacttagctg tgccactctt agtatcgtta acggtgtttt tgagttcatc   1620
gccgaagtgc ctgagaagtt ggctgcggct gttacagttt ttgtcaactt cttgaatgag   1680 cttttttgagt ctgcctgtga ctgcttaaag gtcggaggta aaaccttaa caaggttggc    1740 tcttatgttc tttttgacaa cgcattggtt aagcttgtca aggcaaaagt tcgcggccca   1800
cgacaggcag gtgtttgtga agttcgttac acaagccttg ttattgggag tactaccaag   1860
gtggtttcca agcgcgttga aaatgccaat gtgaatctcg tcgtcgttga cgaggatgtg   1920
accctcaaca ccactggtcg tacagttgtt gttgacggac ttgcattctt cgagagtgac   1980
gggttttaca gacatcttgc tgatgctgac gttgtcattg aacatcctgt ttataagtct   2040
gcttgtgagc tcaagccagt ttttgagtgt gacccaatac ctgattttcc tatgcctgtg   2100
gccgctagtg ttgcagagct ttgtgtgcaa actgatctgt tgcttaaaaa ttacaacact   2160
ccttataaaa cttacagctg cgttgtgaga ggtgataagt gttgcatcac ttgcaccttta  2220 catatcacag caccaagtta tatggaggat gctgctaatt tgtagacct ctgtaccaag    2280 aacattggta ctgctggttt tcatgagttt tacattacgg cccatgaaca acaggatctg   2340
caagggttcg taaccacttg ttgcacgatg tcaggttttg agtgttttat gcctataatc   2400
ccacagtgtc cagcagtgct tgaagagatt gatggtggta gcatctggcg gtctttttatc  2460 actggtctta atacaatgtg ggattttttgc aagcatctta aagtcagctt tggactagat   2520
ggcattgttg tcactgtagc acgcaaattt aaacgacttg tgctctcttt ggcagaaatg   2580
tataacactt acctttcaac tgtggtggaa aacttggtac tggccggtgt tagcttcaag   2640
tattatgcca ccagtgtccc aaaaattgtt ttgggctgtt gttttcacag tgttaaaagt   2700
gttcttgcaa gtgccttcca gattcctgtc caggcaggca ttgagaagtt taaagtcttc   2760
cttaactgtg ttcaccctgt tgtaccacgc gtcattgaaa cttcttttgt ggaattagaa   2820
gagacgacat ttaaaccacc agcactcaat ggtagtattg ctattgttga tggctttgct   2880
ttctattatg atggaacact atactatccc accgatggta atagtgttgt gcctatttgt   2940
tttaagaaga agggtggtgg tgatgtcaaa ttctctgatg aagtctctgt tagaaccatt   3000
gacccagttt ataaggtctc ccttgaattt gagttcgagt ctgagactat tatggctgtg   3060
cttaataagg ctgttggtaa tcgtatcaag gttacaggtg gttgggacga tgttgttgag   3120
tatatcaacg ttgccattga ggttcttaaa gatcatatcg atgtgcctaa gtactacatc   3180
tatgatgagg aaggtggcac cgatcctaat cttcccgtaa tggtttctca gtggccgttg   3240
aatgatgaca cgatctcaca ggatctgctt gatgtggaag ttgttactga tgcaccaatt   3300
gatttcgagg gtgatgaagt agactcctct gaccctgata aggtggcaga gtggctaaac   3360
tctgagcctg aggatgatgg tcctaatgta gctcctgaaa caaatgtaga gtctgaagtt   3420
```

-continued

```
gaggaagttg ccgcaacctt gtcttttatt aaagatacac cttccacagt tactaaggat    3480
ccttttgctt ttgactttgc aagctatgga ggacttaagg ttttaagaca atctcataac    3540
aactgctggg ttacttctac cttggtgcag ctacaattgc ttggcatcgt tgatgaccct    3600
gcaatggagc ttttagtgc tggtagagtt ggtccaatgg ttcgcaaatg ctatgagtca    3660
caaaaggcta tcttgggatc tttgggtgat gtgtcggctt gcctagagtc cctgactaag    3720
gacctacaca cacttaagat tacctgttct gtagtctgtg gttgtggtac tggtgaacgt    3780
atctatgagg gttgtgctt tcgtatgacg ccaactttgg aaccgttccc atatggtgct    3840
tgtgctcagt gtgctcaagt tttgatgcac acttttaaaa gtattgttgg caccggcatc    3900
ttttgtcgag atactactgc tctctccttg gattctttgg ttgtaaaacc tctttgtgcg    3960
gctgctttta taggcaagga cagtggtcat tatgtcacta actttatga tgctgctatg    4020
gctattgatg gttatggtcg tcatcagata aagtatgaca cactgaacac tatttgtgtt    4080
aaagacgtta attggacagc accttttgtc ccagacgttg agcctgtatt ggagcctgtt    4140
gtcaaaccgt tctattctta taagaatgtt gattttacc aaggagattt tagtgacctt    4200
gttaaacttc catgtgactt tgttgttaat gctgcaaatg agaatttgtc tcacggtggc    4260
ggcatagcaa aggccattga tgtttatacc aagggcatgt tgcagaagtg ctcgaatgat    4320
tacattaaag cacacggtcc cattaaagtt ggacgtggtg tcatgttgga ggcattaggt    4380
cttaaggtct ttaatgttgt tggtccacgt aagggtaagc atgcacctga gcttcttgtt    4440
aaggcttata agtccgtttt tgctaattca ggtgttgctc ttacaccttt gattagtgtt    4500
ggaatttta gtgttccttt ggaagaatct ttatctgctt tcttgcatg tgttggtgat    4560
cgccactgta agtgcttttg ttatagtgac aaagagcgcg aggcgatcat taattacatg    4620
gatggcttgg tagatgctat tttcaaagat gcacttgttg atactactcc tgtccaggaa    4680
gatgttcaac aagtttcaca aaaccagtt tgcctaatt ttgaaccttt caggattgaa    4740
ggtgctcatg ctttctatga gtgcaaccct gaaggtttga tgtcattagg tgctgacaag    4800
ctggtgttgt ttacaaattc caatttggat ttttgtagcg ttggtaagtg tcttaacaat    4860
gtgactggcg gtgcattgct tgaagccata aatgtattta aaaagagtaa caaaacagtg    4920
cctgctggca actgtgttac ttttgagtgt gcagatatga tttctattac tatggtagta    4980
ttgccatctg acggtgatgc taattatgac aaaaattatg cacgcgccgt cgtcaaggta    5040
tctaagctta aaggcaagtt attgcttgct gttggtgatg ctatgttgta ttccaagttg    5100
tcccacctca gcgtgttagg tttcgtatcc acacctgatg atgtggagcg tttctacgca    5160
aataagagtg tggttattaa agttactgag gatacacgta gtgttaagac tgttaaagta    5220
gaatccactg ttacttatgg acaacaaatt ggaccttgtc ttgttaatga caccgttgtc    5280
acagacaaca aacctgttgt tgctgatgtt gtagctaagg ttgtaccaag tgctaattgg    5340
gattcacatt atggttttga taaggctggt gagttccaca tgctagacca tactgggttt    5400
gcctttccta gtgaagttgt taacggtagg cgtgtgctta aaaccacaga taataactgt    5460
tgggttaatg ttacatgttt acaattacag tttgctagat ttaggttcaa gtcagcaggt    5520
ctacaggcta gtgggagtc ctattgtact ggtgatgttg ctatgtttgt gcattggttg    5580
tactggctta ctggtgttga caaaggtcag cctagtgatt cagaaaatgc acttaacatg    5640
ttgtctaagt acattgttcc tgctggttct gtcactattg aacgtgtcac gcatgacggt    5700
tgttgttgta gtaagcgtgt tgtcactgca ccagttgtga atgctagcgt gttgaagctt    5760
ggcgtcgagg atggtctttg tccacatggt cttaactaca ttgacaaagt tgttgtagtt    5820
```

```
aaaggtacta caattgttgt caatgttgga aaacctgtag tggcaccatc gcacctcttt    5880
cttaagggtg tttcctacac aacattccta gataatggta acggtgttgc cggccattat    5940
actgtttttg atcatgacac tggtatggtg catgatggag atgtttttgt accaggtgat    6000
ctcaatgtgt ctcctgttac aaatgttgtc gtctcagagc agacggctgt tgtgattaaa    6060
gaccctgtga agaaagtaga gttagacgct acaaagctgt tagacactat gaattatgca    6120
tcggaaagat tcttttcctt tggtgatttt atgtcacgta atttaattac agtgttttg     6180 tacatcctta gtattttggg tctctgtttt agggcctttc gtaagaggga tgttaaagtt    6240
ctagctggtg tacccaacg tactggtatt atattgcgta aaagtgtgcg ctataatgca     6300
aaggctttgg gtgtcttctt caagctaaaa ctttattggt tcaaagttct tggtaagttt    6360
agtttgggta tttatgcatt gtatgcatta ctattcatga caatacgctt tacacctata    6420
ggtggccctg tttgtgatga tgttgttgct ggttatgcta attctagttt tgacaagaat    6480
gagtattgca acagtgttat tgtaaggtc tgtctctatg gtaccagga actttcggac      6540 ttctctcaca cacaggtagt atggcaacac cttagagacc cattaattgg taatgtgatg    6600 ccttctttt atttggcatt tctggcaatt ttggggggtg tttatgtaaa ggctattact     6660
ctctatttta ttttccagta tcttaacata cttggtgtgt ttttgggcct acaacagtcc    6720
atttggtttt tgcagcttgt gccttttgat gtctttggtg acgagatcgt cgtctttttc    6780
atcgttacac gcgtattgat gttccttaag catgttttcc ttggctgcga taaggcatct    6840
tgtgtggctt gctctaagag tgctcgcctt aagcgcgttc ctgtccagac tattttcag    6900 ggtactagca aatccttcta cgtacatgcc aatggtggtt ctaagttctg taagaagcac    6960
aatttctttt gttaaattg tgattcttat ggtccaggct gcacttttat taatgacgtc     7020
attgcaactg aagttggtaa tgttgtcaaa cttaatgtgc aaccgacagg tcctgccact    7080
attcttattg acaaggttga attcagtaat ggttttttact atctttatag tggtgacaca   7140
ttttggaagt acaactttga cataacagat aacaaataca cttgcaaaga gtcacttaaa    7200
aattgtagca taatcacaga ctttattgtt tttaacaata atggttccaa tgtaaatcag    7260
gttaagaatg catgtgtgta ttttttcacag atgctttgta aacctgttaa gttagtggac    7320
tcagcgttgt tggccagttt gtctgttgat tttggtgcaa gcttacatag tgcttttgtt    7380
agtgtgttgt cgaatagttt tggcaaagac ctgtcaagtt gtaatgacat gcaggattgc    7440
aagagcacat tgggttttga tgatgtacca ttggatacct ttaatgctgc tgttgctgag    7500
gctcatcgtt acgatgtcct cttgactgac atgtcgttca acaattttac caccagttat    7560
gcaaaaccag aggaaaaact tccgtccat gacattgcca cgtgtatgcg tgtaggtgcc     7620
aagattgtta atcataacgt tcttgtcaag gatagtatac ctgtggtgtg gcttgtacgt    7680
gatttcattg ccctttctga agaaactagg aagtacatta ttcgtacgac taaagttaag    7740
ggtataacct tcatgttgac ctttaatgat tgtcgtatgc atactaccat acctactgtt    7800
tgcattgcaa ataagaaggg tgcaggtctt cctagttttt caaaggttaa gaaattcttc    7860
tggtttttgt gtctgttcat agttgctgtt ttctttgcac taagcttttt tgattttagt    7920
actcaggtta gcagtgatag tgattatgac ttcaagtata ttgagagtgg ccagttgaag    7980
acttttgaca atccacttag ttgtgtgcat aatgtcttta gtaacttcga ccagtggcat    8040
gatgccaagt ttggtttcac ccccgtcaac aatcctagtt gtcctatagt cgttggtgta    8100
tcagacgaag cgcgcactgt tccaggtatc ccagcaggtg tttatttagc tggtaaaaca   8160
```

```
cttgttttg   ctattaacac   cattttggt    acatctggtt   tgtgctttga   tgctagtggc   8220
gttgctgata  agggcgcttg   catttttaat   tcggcttgca   ccacattatc   tggtttgggt   8280
ggaactgctg  tctactgtta   taagaatggt   ctagttgaag   gtgctaaact   ttatagtgag   8340
ttggcacctc  atagctacta   taaaatggta   gatggtaatg   ctgtgtcttt   acctgaaatt   8400
atctcgcgcg  gctttggcat   ccgtactatc   cgtacaaagg   ctatgaccta   ctgtcgcgtt   8460
ggccagtgtg  tgcaatctgc   agaaggtgtt   tgttttggcg   ccgatagatt   ctttgtctat   8520
aatgcagaat  ctggttctga   ctttgtttgt   ggcacagggc   tctttacatt   gttgatgaac   8580
gttattagtg  tttttttccaa  gacagtacca   gtaactgtgt   tgtctggtca   aatactttt   8640 aattgcatta  ttgcttttgc   tgctgttgcg   gtgtgtttct   tatttacaaa   gtttaagcgc   8700
atgttcggtg  atatgtctgt   tggcgttttc   actgtcggtg   cttgtacttt   gttgaacaat   8760
gtttcctaca  ttgtaacaca   gaacacactt   ggcatgttgg   gctatgcaac   tttgtacttt   8820
ttgtgcacta  aaggtgttag   atatatgtgg   atttggcatt   tgggattttt   gatctcatat   8880
atacttattg  caccatggtg   ggttttgatg   gtttatgcct   tttcagccat   ttttgagttt   8940
atgcctaacc  ttttaagct    taaggtttca   acacaacttt   tgagggtga    caagttcgta   9000 ggctcttttg  aaaatgctgc   agcaggtaca   tttgtgcttg   atatgcatgc   ctatgagaga   9060
cttgccaact  ctatctcaac   tgaaaaactg   cgtcagtatg   ctagtactta   caataagtac   9120
aagtattatt  caggcagtgc   ttcagaggct   gattacaggc   ttgcttgttt   tgcccatttg   9180
gccaaggcta  tgatggatta   tgcttctaat   cacaacgaca   cgttatacac   accacccact   9240
gtgagttaca  attcaactct   acaggctggc   ttgcgtaaga   tggcacaacc   atctggtgtt   9300
gttgagaagt  gcatagttcg   tgtttgctat   ggtaatatgg   ctcttaatgg   cctatggctt   9360
ggtgatactg  ttatctgccc   acgccatgtt   atagcgtcta   gtactactag   cactatagat   9420
tatgactatg  ccctttctgt   tttacgcctc   cacaacttct   ccatttcatc   tggtaatgtt   9480
ttcctaggtg  ttgtgggtgt   aaccatgcga   ggtgctttgt   tgcagataaa   ggttaatcaa   9540
aacaatgtcc  acacgcctaa   gtacacctat   cgcacagtta   gaccgggtga   atcttttaat   9600
atcttggcgt  gctatgatgg   ttctgcagct   ggtgtttacg   gcgttaacat   gcgctctaat   9660
tacactatta  gaggctcgtt   cattaatggc   gcttgtggtt   cacctggtta   taatattaac   9720
aatggtaccg  ttgagttttg   ctatttacac   cagcttgaac   ttggtcagg    ctgtcatgtt   9780 ggtagcgact  tagatggtgt   tatgtatggt   ggttatgagg   accaacctac   tttgcaagtt   9840
gaaggcgcta  gtagtctgtt   tacagagaat   gtgttggcat   ttcttatgc    agcactcatt   9900 aatggttcta  cctggtggct   tagttcttct   aggattgctg   tagacaggtt   taatgagtgg   9960
gctgttcata  atggtatgac   aacagtagtt   aatactgatt   gcttttctat   tcttgctgct  10020
aagactggtg  ttgatgtaca   acgtttgttg   gcctcaatcc   agtctctgca   taagaatttt  10080
ggtggaaagc  aaattcttgg   ctataccctcg  ttgacagatg   agtttactac   aggtgaagtt  10140
atacgtcaaa  tgtatggcgt   taatcttcag   agtggttatg   tttcacgcgc   ctgtagaaat  10200
gtcttgctgg  ttggttcttt   tctgactttc   ttttggtcag   aattagtttc   ctacactaag  10260
ttcttttggg  taaatcctgg   ttatgtcaca   cctatgtttg   cgtgtttgtc   attgctgtcc  10320 tcactttga   tgttcacact   caagcataag   acattgtttt   tccaggtctt   tctaatacct  10380
gctctgattg  ttacatcttg   cattaatttg   gcatttgatg   ttgaagtcta   caactatttg  10440
gcagagcatt  ttgattacca   tgtttctctc   atgggtttta   atgcacaagg   tcttgttaac  10500
atctttgtct  gctttgttgt   taccattttta  cacggcacat   acacatggcg   ctttttaac  10560
```

```
acacctgtga gttctgtcac ttatgtggta gctttgctga ctgcggcata taactatttt    10620
tacgctagtg acattcttag ttgtgctatg acactatttg ctagtgtgac tggcaactgg    10680
ttcgttggtg ctgtttgtta taaagctgct gtttatatgg ccttgagatt tcctactttt    10740
gtggctattt ttggtgatat taagagtgtt atgttctgtt accttgtgtt gggttatttt    10800
acctgttgct tctacggtat tctctactgg ttcaacaggt tttttaaggt tagtgtaggt    10860
gtctatgact atactgttag tgctgctgag tttaagtata tggttgctaa cggcctacgt    10920
gcaccaactg gaacacttga ttcactactt ctgtctgcca aattgattgg tattggtggt    10980
gagcggaata ttaagatttc ttccgttcag tctaaactga ctgatattaa gtgtagtaac    11040
gttgtgcttt taggctgtct ctctagcatg aatgtctcag caaattcaac agaatgggcc    11100
tattgtgttg acttgcataa caagatcaac ttgtgtaatg acccagaaaa agcgcaggaa    11160
atgctacttg ctttgttggc attttttcctt agtaagaata gtgcttttgg tttagatgac    11220
ttattggaat cctattttaa tgacaatagt atgttgcaga gtgttgcatc tacttatgtc    11280
ggtttgcctt cttatgtcat ttatgaaaat gcacgccaac agtatgaaga tgctgttaat    11340
aatggttctc cacctcagtt ggttaagcaa ttgcgccatg ccatgaatgt agcaaagagc    11400
gaatttgacc gtgaggcttc tactcagcgt aagcttgata gaatggcgga acaggctgca    11460
gcacagatgt acaaagaggc acgagcagtt aataggaagt ccaaagttgt aagtgctatg    11520
cattcactgc tttttggtat gttgagacgt ttggacatgt cttctgtaga caccattctc    11580
aacttggcaa aggatggggt tgtacctctg tctgtcatac cggcagtcag tgctactaag    11640
cttaacattg ttacttctga tatcgattct tataatcgta tccagcgtga gggatgtgtc    11700
cactacgctg gtaccatttg gaatataatt gatatcaagg acaatgatgg caaggtggta    11760
cacgttaagg aggtaaccgc acagaatgct gagtccctgt catggcccct ggtccttggg    11820
tgtgagcgta ttgtcaagct ccagaataat gaaattattc ctggtaagct gaagcagcgc    11880
tccattaagg cagaaggaga tggcatagtt ggagaaggta aggcactttta caataatgag    11940 ggtggacgta cttttatgta tgctttcatc tcggacaaac cggacctgcg tgtagtcaag    12000
tgggagttcg atggtggttg taacactatt gagctagaac caccacgtaa gttcttggtg    12060
gattctccta atggtgcaca gatcaagtat ctctactttg ttcgtaacct aacacgttat    12120 cgtagggtg ctgttctcgg ctacataggt gccactgtac gcttgcaggc tggtaaacaa    12180
acagaacagg ctattaactc ttcattgttg acactttgcg ctttcgctgt ggatcctgct    12240
aagacctaca tcgatgctgt caaaagtggt cacaaaccag taggtaactg tgttaagatg    12300
ttggccaatg gttctggtaa tggacaagct gttactaatg gtgtggaggc tagtactaac    12360
caggattcat acggtggtgc gtccgtgtgt ctatattgta gagcacatgt tgagcatcca    12420
tctatggatg gttttttgcag actgaaaggc aagtacgtac aggttccact aggtacagtg    12480
gatcctatac gttttgtact tgagaatgac gtttgcaagg tttgtggttg ttggctggct    12540
aatggctgca cttgtgacag atccattatg caaagcactg atatggctta tttaaacgag    12600
tacggggctc tagtgcagct cgactagagc cctgtaacgg tactgataca caacatgtgt    12660
atcgtgcttt tgacatctac aacaaggatg ttgcttgtct aggtaaattc ctcaaggtga    12720
actgtgttcg cctgaagaat ttggataagc atgatgcatt ctatgttgtc aaaagatgta    12780
ccaagtctgc gatggaacac gagcaatcca tctatagcag acttgaaaag tgtggagccg    12840
tagccgaaca cgatttcttc acttggaagg atggtcgtgc catctatggt aacgtttgta    12900
```

-continued

```
gaaaggatct taccgagtat actatgatgg atttgtgtta cgctttacgt aactttgatg    12960
aaaacaattg cgatgttctt aagagcattt taattaaggt aggcgcttgt gaggagtcct    13020
acttcaataa taaagtctgg tttgaccctg ttgaaaatga agacattcat cgtgtctatg    13080
cattgttagg taccattgtt tcacgtgcta tgcttaaatg cgttaagttc tgtgatgcaa    13140
tggttgaaca aggtatagtt ggtgttgtca cattagataa tcaggatctt aatggtgatt    13200
tttatgattt tggtgatttt acttgtagca tcaagggaat gggtataccc atttgcacat    13260
catattactc ttatatgatg cctgttatgg gtatgactaa ttgccttgct agtgagtgtt    13320
ttgttaagag tgatatattt ggtgaggatt tcaagtcata tgacctgctg gaatatgatt    13380
tcacggagca taagacagca ctcttcaaca agtatttcaa gtattgggga ctgcaatacc    13440
accctaactg tgtggactgc agtgatgagc agtgcatagt tcactgtgcc aacttcaata    13500
cgttgttttc cactactata cctattacgg catttggacc tttgtgtcgc aagtgttgga    13560
ttgatggtgt tccactggta actacagctg gttatcattt taaacagtta ggtatagttt    13620
ggaacaatga cctcaactta cactctagca ggctctctat taacgaatta ctccagtttt    13680
gtagtgatcc tgcattgctt atagcatcat caccagccct tgttgatcag cgtactgttt    13740
gcttttcagt tgcagcgcta ggtacaggta tgactaacca gactgttaaa cctggccatt    13800
tcaataagga gttttatgac ttcttacttg agcaaggttt cttttctgag ggctctgagc    13860 ttacttaaa gcacttcttc tttgcacaga agggtgatgc agctgttaag gattttgact    13920
actataggta taatagacct actgttctgg acatttgcca agctcgcgtc gtgtatcaaa    13980
tagtgcaacg ctattttgat atttacgaag gtggttgtat cactgctaaa gaggtggttg    14040
ttacaaacct taacaagagc gcaggttatc ctttgaacaa gtttggtaaa gctggtcttt    14100
actatgagtc tttatcctat gaggaacagg atgaacttta tgcttatact aagcgtaaca    14160
tcctgcccac tatgacacag ctcaacctta aatatgctat aagtggcaaa gaacgtgcac    14220
gcacagtggg tggtgtttcg cttttgtcaa ccatgactac tcggcagtat catcagaaac    14280
acctcaagtc catagttaat actaggggcg cttcggttgt tattggtact actaagtttt    14340
atggtggttg ggacaatatg cttaagaacc ttattgatgg tgttgaaaat ccgtgtctta    14400
tgggttggga ctacccaaag tgcgacagag cactgcccaa tatgatacgt atgatttcag    14460
ccatgatttt aggctctaag cacaccacat gctgcagttc cactgaccgc tttttcaggt    14520
tgtgcaatga attggctcaa gtccttactg aggttgttta ttctaatgga ggttttatt    14580 tgaagccagg tggtactacc tctggtgatg caaccaccgc atatgcaaac tcagtttta    14640 atatcttcca agcagtaagt gccaatgtta acaaacttct tagtgttgac agcaatgtct    14700
gtcataattt agaagttaag caattgcagc gtaagcttta tgagtgctgt tatagatcaa    14760
ctaccgtcga tgaccagttc gtcgttgagt attatggtta cttgcgtaaa catttttcaa    14820
tgatgattct ttctgatgat ggcgttgttt gttataacaa tgactatgca tcacttggtt    14880
atgtcgctga tcttaacgca ttcaaggctg ttttgtatta ccagaacaat gtcttcatga    14940
gcgcctctaa atgttggatc gagcctgaca ttaataaagg tcctcatgaa ttttgctcgc    15000
agcatactat gcagattgtc gataaagatg gtacttatta ccttcttac cctgatcctt    15060 caagaattct ctctgcaggt gtgtttgttg atgacgttgt taaaactgat gcagttgtat    15120
tgcttgaacg ttatgtgtca ttggctatag atgcctaccc gttatctaag catgaaaatc    15180
ctgaatataa gaaggtgttt tatgtgcttt tggattgggt taagcatctg tacaaaactc    15240
ttaatgctgg tgtgttagag tcttttttctg tcacactttt ggaagattct actgctaaat    15300
```

```
tctgggatga gagcttttat gccaacatgt atgagaaatc tgcagtttta caatctgcag   15360
ggctttgtgt tgtttgtggc tctcaaactg ttttacgttg tggtgattgt ctacggcgtc   15420
ctatgctttg tactaagtgt gcttatgatc atgtcattgg aacaactcac aagttcattt   15480
tggccatcac tccatatgtg tgttgtgctt cagattgtgg tgtcaatgat gtaactaagc   15540
tctacttagg tggtcttagt tattggtgtc atgaccacaa gccacgtctt gcattcccgt   15600
tgtgctctgc tggtaatgtt tttggcttgt acaaaaattc tgctaccggc tcacccgatg   15660
ttgaagactt taatcgcatt gctacatccg attggactga tgtttctgac tacaggttgg   15720
caaatgatgt caaggactca ttgcgtctgt tgcagcggaa aactatcaag gccaaggagg   15780
agagcgttaa gtcatcctat gcttgtgcaa cactacatga ggttgtagga cctaaagagt   15840
tgttgctcaa atgggaagtc ggcagaccca aaccacccct aatagaaat tcggttttca   15900 cttgttatca taacgaag aacaccaaat ttcaaatcgg tgagtttgtg tttgagaagg   15960
cagaatatga taatgatgct gtaacatata aaactaccgc cacaacaaaa cttgttcctg   16020
gcatggtttt tgtgcttacc tcacataatg ttcagccatt gcgcgcaccg accattgcta   16080
atcaagaacg ttattccact atacataagt tgcatcctgc ttttaacata cctgaagctt   16140
attctagctt agtgccctat taccaattga ttggtaagca gaagattaca actattcagg   16200
gacctcccgg tagtggtaaa tctcactgtg ttatagggct aggtttgtac tatccaggtg   16260
cacgtatagt gtttacagct tgttctcatg cagcggtcga ttcactttgt gtgaaagctt   16320
ccactgctta tagcaatgac aaatgttcac gcatcatacc acagcgcgct cgtgttgagt   16380
gttatgatgg tttcaagtct aataatacta gtgctcagta ccttttctct actgtcaatg   16440
ctttgccaga gtgcaatgcg gacattgttg tggtggatga ggtctctatg tgcactaatt   16500
atgacttgtc tgtcataaat cagcgcatca gctataggca tgtagtctat gttggtgacc   16560
ctcaacagct gcctgcacca cgtgttatga tttcacgtgg tacttttgaa ccaaaggact   16620
acaacgttgt cactcaacgc atgtgtgccc ttaagcctga tgtttttcttg cacaagtgtt   16680 atcgctgtcc tgctgagata gtgcgtactg tgtctgagat ggtctatgaa accaattca   16740 ttcctgtgca cccagatagc aagcagtgtt ttaaaatctt ttgcaagggt aatgttcagg   16800
ttgataatgg ttcaagcatt aatcgcaggc aattggatgt tgtgcgtatg tttttggcta   16860
aaaatcctag gtggtcaaag ctgtttttta tttctcctta taacagccag aattatgttg   16920
ccagccgcat gctaggtcta caaattcaga cagttgactc atcccagggt agtgagtatg   16980
actatgtcat ttacacacaa acttcagata ctgcccatgc ctgtaatgtt aacaggttta   17040
atgttgccat cacaagggcc aagaaaggca tattatgtat aatgtgcgat aggtcccttt   17100
ttgatgtgct taaattcttt gagcttaaat tgtctgattt gcaggctaat gagggttgtg   17160
gtctttttaa agactgtagc agaggtgatg atctgttgcc accatctcac gctaacacct   17220
tcatgtcttt agcggacaat tttaagactg atcaagatct tgctgttcaa ataggtgtta   17280
atggacccat taaatatgag catgttatct cgtttatggg cttccgtttt gatatcaaca   17340
tacccaacca tcacactctc ttttgcacac gcgactttgc catgcgcaat gttagaggtt   17400
ggttgggttt tgacgttgaa ggagcacatg ttgttggctc taacgtcggt acaaatgtcc   17460
cattgcaatt agggttttct aacggtgttg attttgttgt cagacctgaa ggttgcgttg   17520
taactgagtc tggtgactac attaaacccg tcagagctcg tgctccacca ggggaacaat   17580
ttgcacacct tttgcctcta cttaaacgcg gccaaccatg ggatgtggtt cgtaagcgta   17640
```

```
tagtgcaaat gtgtagtgac tacctggcta acctatcaga catactaatt tttgtgttgt    17700
gggctggtgg tttggagttg acaactatgc gttactttgt caagattgga ccaagcaaga    17760
gttgtgattg tggtaaggtt gctacttgtt acaatagtgc gctgcatacg tactgttgtt    17820
tcaaacatgc ccttggttgt gattacctgt acaatcccata ctgtattgat atacagcagt   17880
ggggatacaa gggatcactt agccttaacc accatgagca ttgtaatgta catagaaacg    17940
agcatgtggc ttctggtgat gccataatga ctcgctgtct agccatacat gattgctttg    18000
tcaagaacgt tgactggtcc atcacatacc catttattgg taatgaggct gttattaata    18060
agagcggccg aattgtgcaa tcacacacta tgcggtcagt tcttaagtta tacaatccaa    18120
aagccatata tgatattggc aaccctaagg gcattagatg tgccgtaacg gatgctaagt    18180
ggttctgctt tgacaagaat cctactaatt ctaatgtcaa gacattggag tatgactata    18240
taacacacgg ccaatttgat gggttgtgct tgttttggaa ttgcaatgtg gacatgtatc    18300
cagaattctc tgtggtctgt cggttttgaca ctcgctgtag gtcaccactc aacttggagg   18360
gttgtaatgg tggttcactg tatgttaata atcatgcatt ccatacaccg gcttttgaca    18420
agcgtgcttt tgccaagttg aagccaatgc cattttctt ctatgatgat actgagtgtg     18480
acaagttaca ggactctata aactacgttc ctcttagggc tagtaattgc attactaaat    18540
gtaatgttgg tggagctgtc tgtagtaagc attgtgctat gtaccatagc tatgttaatg    18600
cttacaacac ctttacgtcg gcgggcttta cgatttgggt gcccacttcg tttgacacct    18660
acaatctgtg gcagacattt agtaacaact gcaaggtct tgagaacatt gctttcaatg     18720
tcgtaaagaa aggatctttt gttggtgctg aaggtgagct tcctgtagct gtggttaatg    18780
acaaagtgct cgttagagat ggtactgttg atactcttgt tttcacaaac aagacatcac    18840
tacccactaa cgtagctttt gagttgtatg ccaagcgtaa ggtaggactc accccaccca    18900
ttacgatcct acgtaacttg ggtgttgttt gcacatctaa gtgtgtcatt tgggactatg    18960
aagccgaacg tccacttact acttttacaa aggatgtctg taaatatacc gactttgagg    19020
gtgacgtttg cacactcttt gataacagca ttgttggttc attagagcga ttctctatga    19080
cccaaaatgc tgtgcttatg tcacttacag ctgttaaaaa gcttactggc ataaagttaa    19140
cttatggtta tcttaatggt gtcccagtta acacacatga agataaacct tttacttggt    19200
acatttacac taggaagaac ggcaagttcg aggactatcc tgatggctat tttacccaag    19260
gtagaacaac cgctgatttt agccctcgta gtgacatgga aaaggacttc ctaagtatgg    19320
atatgggtct gtttattaac aagtacggac tcgaagatta cggcttttgag cacgttgtgt   19380 atggtgatgt ttctaaaacc acccttggtg gtttacatct actaatttcg caggtgcgtc    19440
tggcctgtat gggtgtgctt aaaatagacg agtttgtgtc tagtaatgat agcacgttaa    19500
agtcttgtac tgttacatat gctgataacc ctagtagtaa gatggtttgc acgtatatgg    19560
atctccttct tgacgatttt gtcagcattc ttaaatcgtt ggatttgagt gttgtatcta    19620
aagttcatga agtatggtc gattgtaaaa tgtggaggtg gatgttgtgg tgtaaggatc     19680
ataaactcca gacattttat ccgcaacttc aggccagtga atggaaatgt ggttattcca    19740
tgccttctat ttacaagata caacgtatgt gtttagaacc ttgcaatctc tataactatg    19800
gtgctggtat taagttacct gatggcatta tgtttaacgt agttaaatat acacagcttt    19860
gtcaatatct taatagcacc acaatgtgtg tacccatca catgcgcgtg ctacatcttg     19920
gtgctggctc cgacaagggt gttgcacctg gcacggctgt cttacgacgt tggttgccac    19980
tggatgccat tatagttgac aatgatagtg tggattacgt tagcgatgct gattatagtg    20040
```

```
ttacgggaga ttgctctacc ttatacctgt cagataagtt tgacttagtt atatctgata   20100
tgtatgatgg taagattaaa agttgtgatg gggagaacgt gtctaaagaa ggcttctttc   20160
cctatattaa tggtgtcatc actgaaaagt tggcacttgg tggtactgta gctattaagg   20220
tgacggagtt tagttggaat aagaagttgt atgaactcat tcagaggttt gagtattgga   20280
caatgttctg taccagtgtt aacacgtcat cgtcagaggc attcttaatt ggtgttcact   20340
atttaggtga ttttgcaagt ggcgctgtga ttgacggcaa cactatgcat gccaattata   20400
tcttctggcg taattccaca attatgacta tgtcttacaa tagtgtactt gatttaagca   20460
agttcaattg taagcataag gctacagttg tcattaattt aaaagattca tccattagtg   20520
atgttgtgtt aggtttgttg aagaatggta agttgctagt gcgtaataat gacgccattt   20580 gtggttttc taatcatttg gtcaacgtaa acaaatgaag tctttaacct acttctggtt    20640
gttcttacca gtactttcaa cactcagcct accacaagat gtcactaggt gccagtccac   20700
tattaacttc aggcggttct tttcaaaatt taatgtgcag gcacctgctg tcgttgtgtt   20760
gggtggttat ctacctagta tgaactcctc tagctggtac tgtggcacag gtcttgaaac   20820
tgctagtggc gtgcatggta ttttcctcag ttacatcgat tctggtcagg ctttgagat    20880 tggcatttca caggagccgt tgatcctag tggttaccag ctttatttac ataaggccac    20940
taatggtaac cataatgcta ttgcacgact gcgcatttgc cagtttccag ataataaaac   21000
attgggccct actgttaatg atgttacaac aggtcgtaac tgcctattca caaagccat    21060 tccagcttat atgcaggatg aaaaaatat cgttgtcggc ataacatggg acaatgatcg    21120
tgtcactgtt tttgctgaca agatctatca tttttatctt aaaaatgatt ggtcccgtgt   21180
tgcgacaaga tgttacaata aaagaagttg tgctatgcaa tatgtttata cacctaccta   21240
ctacatgctt aatgttacta gtgcaggtga ggatggcatt tattatgaac catgtacagc   21300
taattgcagt ggttacgctg ccaatgtgtt tgccactgat tctaatggcc acataccaga   21360
aggttttagt tttaataatt ggtttctttt gtccaatgat tccactttgt tgcatggtaa   21420 ggtggttttcc aaccaacctt tgttggtcaa ttgtcttttg gccattccta agatttatgg   21480
actaggccaa ttttttctcat tcaatcaaac gatggatggc gtttgtaatg gagctgctgc   21540
gcagcgtgca ccagaggctc tgaggtttaa tattaatgac acctctgtca ttcttgctga   21600
aggctcaatt gtacttcata ctgctttagg aacaaatctt tcttttgttt gcagtaattc   21660
ttcagatcct catctagcta ccttcgccat acctctgggt gctacccaag taccttatta   21720 ttgtttttctt aaagtggata cttacaactc cactgtttat aaattttggg ctgttttacc   21780
tcctactgtc agggaaattg tcatcaccaa gtatggtgat gtttatgtca atgggtttgg   21840
atacttgcat ctcggttgt tggatgctgt cacaattaat ttcactggtc atggcactga   21900
cgatgatgtt tctggttttt ggaccatagc atcgactaat tttgttgatg cactcatcga   21960
agttcaagga accgccattc agcgtattct ttattgtgat gatcctgtta gccaactcaa   22020
gtgttctcag gttgcttttg accttgacga tggttttac cctatttctt ctagaaacct    22080
tctgagtcat gaacagccaa tttctttttgt tactctgcca tcatttaatg atcattcttt   22140
tgttaacatt actgtatctg cttcctttgg tggtcatagt ggtgccaacc ttattgcatc   22200
tgacactact atcaatgggt ttagttcttt ctgtgttgac actagacaat ttaccatttc   22260
actgttttat aacgttacaa acagttatgg ttatgtgtct aaatcacagg acagtaattg   22320 cccctttcacc ttgcaatctg ttaatgatta cctgtctttt agcaaatttt gtgtttccac   22380
```

```
cagccttttg gctagtgmct gtaccataga tcttttggt taccctgagt ttggtagtgg   22440
tgttaagttt acgtcccttt actttcaatt cacaaagggt gagttgatta ctggcacgcc   22500
taaaccactt gaaggtgtca cggacgtttc ttttatgact ctggatgtgt gtaccaagta   22560
tactatctat ggcttaaaag gtgagggtat cattacccct acaaattcta gcttttggc    22620 aggtgtttat tacacatctg attctggaca gttgttagcc tttaagaatg tcactagtgg   22680
tgctgtttat tctgttacgc catgttcttt ttcagagcag gctgcatatg ttgatgatga   22740
tatagtgggt gttatttcta gtttgtctag ctccactttt aacagcacta gggagttgcc   22800
tggtttcttc taccattcta atgatggctc taattgtaca gagcctgtgt tggtgtatag   22860
taacataggt gtttgtaaat ctggcagtat tggctacgtc ccatctcagt ctggccaagt   22920
caagattgca cccacggtta ctgggaatat tagtattccc accaacttta gtatgagtat   22980
taggacagaa tatttacagc tttacaacac gcctgttagt gttgattgtg ccacatatgt   23040
ttgtaatggt aactctcgtt gtaaacaatt actcacccag tacactcag catgtaagac    23100 catagagtca gcattacaac tcagcgctag gcttgagtct gttgaagtta actctatgct   23160
tactatttct gaagaggctc tacagttagc taccattagt tcgtttaatg gtgatggata   23220
taattttact aatgtgctgg gtgtttctgt gtatgatcct gcaagtggca gggtggtaca   23280
aaaaaggtct tttattgaag acctgctttt taataaagtg gttactaatg gccttggtac   23340
tgttgatgaa gactataagc gctgttcaa tggtcgctct gtggcagatc tagtctgtgc    23400
acagtattac tctggtgtca tggtactacc tggtgttgtt gacgctgaga agcttcacat   23460
gtatagtgcg tctctcatcg gtggtatggt gctaggaggt tttacttctg cagcggcatt   23520 gcctttagc tatgctgttc aagctagact caattatctt gctctacaga cggatgttct    23580
acagcggaac cagcaattgc ttgctgagtc ttttaactct gctattggta atataacttc   23640
agcctttgag agtgttaaag aggctattag tcaaacttcc aagggtttga acactgtggc   23700
tcatgcgctt actaaggttc aagaggttgt taactcgcag ggtgcagctt tgactcaact   23760
taccgtacag ctgcaacaca acttccaagc catttctagt tctattgatg acatttactc   23820
tcgactggac attctttcag ccgatgttca ggttgaccgt ctcatcaccg gcagattatc   23880
agcacttaat gcttttgttg ctcaaacct cactaagtat actgaggttc aggctagcag   23940
gaagttagca cagcaaaagg ttaatgagtg cgttaaatcg caatctcagc gttatggttt   24000
ttgtggtggt gatggcgagc acatttctc tctggtacag gcagcacctc agggcctgct   24060 gttttttacat acagtacttg taccgagtga ttttgtagat gttattgcca tcgctggctt   24120
atgcgttaac gatgaaattg ccttgactct acgtgagcct ggcttagtct tgtttacgca   24180
tgaacttcaa aatcatactg cgacggaata ttttgtttca tcgcgacgta tgtttgaacc   24240
tagaaaacct accgttagtg attttgttca aattgagagt tgtgtggtca cctatgtcaa   24300
tttgactaga gaccaactac cagatgtaat cccagattac atcgatgtta acaaaacact   24360
tgatgagatt ttagcttctc tgcccaatag aactggtcca agtcttcctt tagatgtttt   24420
taatgccact tatcttaatc tcactggtga aattgcagat ttagagcagc gttcagagtc   24480
tctccgtaat actacagagg agctccaaag tcttatatat aatatcaaca acacactagt   24540
tgaccttgag tggctcaacc gagttgagac atatatcaag tggccgtggt gggtttggtt   24600
gattattttc attgttctca tcttttgttgt gtcattacta gtgttctgct gcattccac    24660 gggttgttgt ggatgctgcg gctgctgctg tgcttgtttc tcaggttgtt gtaggggtcc   24720
tagacttcaa ccttacgaag ttttgaaaa ggtccacgtg cagtgatgtt tcttggactt    24780
```

```
tttcaataca cgattgacac agttgtcaaa gatgtctcaa agtctgctaa cttgtctttg   24840
gatgctgtcc aagagttgga gctcaatgta gttccaatta gacaagcttc aaatgtgacg   24900
ggttttcttt tcaccagtgt ttttatctac ttctttgcac tgtttaaagc gtcttctttg   24960
aggcgcaatt atattatgtt ggcagcgcgt tttgctgtca ttgttcttta ttgcccactt   25020
ttatattatt gtggtgcatt tttagatgca actattattt gttgcacact tattggcagg   25080
cttttgtttag tctgctttta ctcctggcgc tataaaaatg cgctctttat tatttttaat   25140
actacgacac tttctttcct caatggtaaa gcagcttatt atgacggcaa atccattgtg   25200
attttagaag gtggtgacca ttacatcact tttggcaact cttttgttgc ttttgttagt   25260
agcatcgact tgtatctagc tatacgtggg cggcaagaag ctgacctaca gctgttgcga   25320
actgttgagc ttcttgatgg caagaagctt tatgtctttt cgcaacatca aattgttggc   25380
attactaatg ctgcatttga ctcaattcaa ctagacgagt atgctacaat tagtgaatga   25440
taatggtcta gtagttaatg ttatactttg gcttttcgta ctcttttttcc tgcttattat   25500
aagcattact ttcgtccaat tggttaatct gtgcttcact tgtcaccggt tgtgtaatag   25560
cgcagtttac acacctatag ggcgtttgta tagagtttat aagtcttaca tgcaaataga   25620
ccccctacct agtactgtta ttgacgtata aacgaaatat gtctaacggt tctattcccg   25680
ttgatgaggt gattcaacac cttagaaact ggaatttcac atggaatatc atactgacga   25740
tactacttgt agtgcttcag tatggccatt acaagtactc tgcgttcttg tatggtgtca   25800
agatggctat tctatggata ctttggcctc ttgtgttagc actgtcactt tttgatgcat   25860
gggctagctt tcaggtcaat tgggtctttt ttgctttcag catccttatg gcttgcatca   25920
ctcttatgct gtggataatg tactttgtca atagcattcg gttgtggcgc aggacacatt   25980
cttggtggtc tttcaatcct gaaacagacg cgcttctcac tacttctgtg atgggccgac   26040
aggtctgcat tccagtgctt ggagcaccaa ctggtgtaac gctaacactc cttagtggta   26100
cattgcttgt agagggctat aaggttgcta ctggcgtaca ggtaagtcaa ttacctaatt   26160
tcgtcacagt cgccaaggcc actacaacaa ttgtctacgg acgtgttggt cgttcagtca   26220
atgcttcatc tggcactggt tgggctttct atgtccggtc caaacacggc gactactcag   26280
ctgtgagtaa tccgagttcg gttctcacag atagtgagaa agtgcttcat ttagtctaaa   26340
cagaaacttt atggcttctg tcagttttca ggatcgtggc cgcaaacggg tgccattatc   26400
cctctatgcc cctcttaggg ttactaatga caaaccccctt tctaaggtac ttgcaaataa   26460
tgctgtaccc actaataaag gaaataagga ccagcaaatt ggatactgga atgagcaaat   26520
tcgctggcgc atgcgccgtg gtgagcgaat tgaacaacct tccaattggc atttctacta   26580
cctcggaaca ggacctcacg ccgacctccg ctataggact cgtactgagg gtgttttctg   26640
ggttgctaaa gaaggcgcaa agactgaacc cactaacctg ggtgtcagaa aggcgtctga   26700
aaagccaatt attccaaatt tctctcaaca gcttcccagc gtagttgaga ttgttgaacc   26760
taacacacct cctacttcac gtgcaaattc acgtagcagg agtcgtggta atggcaacta   26820
caggtccaga tctccaagta acaacagagg caataaccag tcccgcggta attcacagaa   26880
tcgtggaaat aaccagggtc gtggagcttc tcagaacaga ggaggcaata ataataacaa   26940
taacaagtct cgtaaccagt ccaagaacag aaaccagtca aatgaccgtg tggtgtaac    27000
atcacgcgat gatctggtgg ctgctgtcaa ggatgccctt aaatctttgg gtattggcga   27060
aaaccctgac aagcttaagc aacagcagaa gcccaaacag gaaaggtctg acagcagcgg   27120
```

-continued

| | |
|---|---|
| caaaaataca cctaagaaga acaaatccag agccacttcg aaagaacgtg acctcaaaga | 27180 |
| catcccagag tggaggagaa ttcccaaggg cgaaaatagc gtagcagctt gcttcggacc | 27240 |
| caggggaggc ttcaaaaatt ttggagatgc ggaatttgtc gaaaaaggtg ttgatgcctc | 27300 |
| aggctatgct cagatcgcca gtttagcacc aaatgttgca gcattgctct ttggtggtaa | 27360 |
| tgtggctgtt cgtgagctag cggactctta cgagattaca tataattata aaatgactgt | 27420 |
| gccaaagtct gatccaaatg tagagcttct tgtttcacag gtggatgcat ttaaaactgg | 27480 |
| gaatgcaaaa ccccagagaa agaaggaaaa gaagaacaag cgtgaaacca cgcagcagct | 27540 |
| gaatgaagag gccatctacg atgatgtggg tgtgccatct gatgtgactc atgccaattt | 27600 |
| ggaatgggac acagctgttg atggtggtga cacggccgtt gaaattatca cgagatcttc | 27660 |
| cgacacagga aattaaacaa tgtttgactg gcttatcctg gctatgtccc agggtagtgc | 27720 |
| cattacactg ttattactga gtgttttctc agcgacttgg ctgctgggct atggctttgc | 27780 |
| cctctaacta gcggtcttgg tcttgcacac aacggtaagc cagtggtaat gtcagtgcaa | 27840 |
| gaaggatatt accatagcac tgtcatgagg ggaacgcagt accttttcat ctaaaccttt | 27900 |
| gcacgagtaa tcaaagatcc gcttgacgag cctatatgga agagcgtgcc aggtatttga | 27960 |
| ctcaaggact gttagtaact gaagacctga cggtgttgat atgga | 28005 |

<210> SEQ ID NO 3
<211> LENGTH: 1170
<212> TYPE: DNA
<213> ORGANISM: Porcine epidemic diarrhea virus

<400> SEQUENCE: 3

| | |
|---|---|
| atgaagtctt taaattactt ctggttgttc ttaccagtac tttcaacact cagcctacca | 60 |
| caagatgtca ctaggtgcca gtccactatt aacttcaggc ggttcttttc aaaatttaat | 120 |
| gtgcaggcac ctgctgtcgt tgtgttgggt ggttatctac ctagtatgaa ctccctctagc | 180 |
| tggtactgtg gcacaggtct tgaaactgct agtggcgtgc atggtatttt cctcagttac | 240 |
| atcgatgctg gtcagggctt tgagattggc atttcacagg agccgtttga tcctagtggt | 300 |
| taccagcttt atttacataa ggccactaat ggtaaccata atgctattgc acgactgcgc | 360 |
| atttgccagt ttcagataa taaaacattg ggccctactg ttaatgatgt tacaacaggt | 420 |
| cgtaactgcc tattcaacaa agccattcca gcttatatgc aggatggaaa aaatatcgtt | 480 |
| gtcggcataa catgggacaa tgatcgtgtc actgttttttg ctgacaagat ctatcatttt | 540 |
| tatcttaaaa atgattggtc ccgtgttgcg acaagatgtt acaataaaag aagttgtgct | 600 |
| atgcaatatg tttatacacc tacctactac atgcttaatg ttactagtgc aggtgaggat | 660 |
| ggcatttatt atgaaccatg tacagctaat tgcagtggtt acgctgccaa tgtgtttgcc | 720 |
| actgattcta atggccacat accagaaggt tttagtttta ataattggtt tcttttgtcc | 780 |
| aatgattcca ctttgttgca tggtaaggtg gtttccaacc aacctttgtt ggtcaattgt | 840 |
| cttttggcca ttcctaagat ttatggacta ggccaatttt tctcattcaa tcaaacgatg | 900 |
| gatggcgttt gtaatggagc tgctgcgcag cgtgcaccag aggctctgag gtttaatatt | 960 |
| aatgacacct ctgtcattct tgctgaaggc tcaattgtac ttcatactgc tttaggaaca | 1020 |
| aatctttctt ttgtttgcag taattcttca gatcctcatc tagctacctt cgccatacct | 1080 |
| ctgggtgcta cccaagtacc ttattattgt tttcttaaag tggatactta caactccact | 1140 |
| gtttataaat ttttggctgt tttacctcct | 1170 |

<210> SEQ ID NO 4
<211> LENGTH: 1170
<212> TYPE: DNA
<213> ORGANISM: Porcine epidemic diarrhea virus

<400> SEQUENCE: 4

```
atgaagtctt taacctactt ctggttgttc ttaccagtac tttcaacact cagcctacca        60
caagatgtca ctaggtgcca gtccactatt aacttcaggc ggttcttttc aaaatttaat       120
gtgcaggcac ctgctgtcgt tgtgttgggt ggttatctac ctagtatgaa ctcctctagc       180
tggtactgtg gcacaggtct tgaaactgct agtggcgtgc atggtatttt cctcagttac       240
atcgattctg gtcagggctt tgagattggc atttcacagg agccgtttga tcctagtggt       300
taccagcttt atttacataa ggccactaat ggtaaccata atgctattgc acgactgcgc       360
atttgccagt ttccagataa taaaacattg ggccctactg ttaatgatgt tacaacaggt       420
cgtaactgcc tattcaacaa agccattcca gcttatatgc aggatggaaa aaatatcgtt       480
gtcggcataa catgggacaa tgatcgtgtc actgttttg ctgacaagat ctatcatttt       540
tatcttaaaa atgattggtc ccgtgttgcg acaagatgtt acaataaaag aagttgtgct       600
atgcaatatg tttatacacc tacctactac atgcttaatg ttactagtgc aggtgaggat       660
ggcatttatt atgaaccatg tacagctaat tgcagtggtt acgctgccaa tgtgtttgcc       720
actgattcta atgccacat accagaaggt tttagtttta ataattggtt tcttttgtcc       780
aatgattcca ctttgttgca tggtaaggtg gtttccaacc aacctttgtt ggtcaattgt       840
cttttggcca ttcctaagat ttatggacta ggccaatttt tctcattcaa tcaaacgatg       900
gatggcgttt gtaatggagc tgctgcgcag cgtgcaccag aggctctgag gtttaatatt       960
aatgacacct ctgtcattct tgctgaaggc tcaattgtac ttcatactgc tttaggaaca      1020
aatctttctt ttgtttgcag taattcttca gatcctcatc tagctacctt cgccatacct      1080
ctgggtgcta cccaagtacc ttattattgt tttcttaaag tggatactta caactccact      1140
gtttataaat ttttggctgt tttacctcct                                        1170
```